US008785396B2

(12) United States Patent
Leone-Bay et al.

(10) Patent No.: US 8,785,396 B2
(45) Date of Patent: Jul. 22, 2014

(54) METHOD AND COMPOSITION FOR TREATING MIGRAINES

(75) Inventors: Andrea Leone-Bay, Ridgefield, CT (US); Grayson W. Stowell, Gaylordsville, CT (US); Joseph J. Guarneri, Stamford, CT (US); Dawn M. Carlson, New Milford, CT (US); Marshall Grant, Newtown, CT (US); Chad C. Smutney, Watertown, CT (US)

(73) Assignee: Mannkind Corporation, Valencia, CA (US)

( * ) Notice: Subject to any disclaimer, the term of this patent is extended or adjusted under 35 U.S.C. 154(b) by 247 days.

(21) Appl. No.: 13/293,017

(22) Filed: Nov. 9, 2011

(65) Prior Publication Data

US 2012/0071510 A1 Mar. 22, 2012

Related U.S. Application Data

(63) Continuation-in-part of application No. 12/258,341, filed on Oct. 24, 2008, now Pat. No. 8,372,804, which is a continuation-in-part of application No. PCT/US2011/041303, filed on Jun. 21, 2011.

(60) Provisional application No. 60/982,368, filed on Oct. 24, 2007, provisional application No. 60/985,620, filed on Nov. 5, 2007, provisional application No. 61/022,274, filed on Jan. 18, 2008, provisional application No. 61/033,740, filed on Mar. 4, 2008, provisional application No. 61/052,127, filed on May 9, 2008, provisional application No. 61/094,823, filed on Sep. 5, 2008, provisional application No. 61/412,339, filed on Nov. 10, 2010, provisional application No. 61/411,775, filed on Nov. 9, 2010, provisional application No. 61/357,039, filed on Jun. 21, 2010.

(51) Int. Cl.
*A61K 47/06* (2006.01)
*A61K 38/12* (2006.01)
*A61K 38/05* (2006.01)

(52) U.S. Cl.
USPC ....... 514/21.1; 424/489; 424/181.1; 424/9.44

(58) Field of Classification Search
None
See application file for complete search history.

(56) References Cited

U.S. PATENT DOCUMENTS

| | | |
|---|---|---|
| 3,906,950 A | 9/1975 | Cocozza |
| 3,921,637 A | 11/1975 | Bennie et al. |
| 4,272,398 A | 6/1981 | Jaffe |
| 4,356,167 A | 10/1982 | Kelly |
| 4,581,020 A | 4/1986 | Mittleman |
| 4,849,227 A | 7/1989 | Cho |
| 4,861,627 A | 8/1989 | Mathiowitz |
| 4,866,051 A | 9/1989 | Hunt et al. |
| 5,118,666 A | 6/1992 | Habener |
| 5,120,712 A | 6/1992 | Habener |
| 5,145,684 A | 9/1992 | Liversidge et al. |
| 5,188,837 A | 2/1993 | Domb |
| 5,260,306 A | 11/1993 | Boardman et al. |
| 5,320,094 A | 6/1994 | Laube et al. |
| 5,352,461 A | 10/1994 | Feldstein et al. |
| 5,424,286 A | 6/1995 | Eng |
| 5,458,135 A | 10/1995 | Patton et al. |
| 5,492,112 A | 2/1996 | Mecikalski et al. |
| 5,503,852 A | 4/1996 | Steiner et al. |
| 5,506,203 A | 4/1996 | Backstrom et al. |
| 5,547,929 A | 8/1996 | Anderson, Jr. et al. |
| 5,574,008 A | 11/1996 | Johnson et al. |
| 5,577,497 A | 11/1996 | Mecikalski et al. |
| 5,631,224 A | 5/1997 | Efendic et al. |
| 5,653,961 A | 8/1997 | McNally et al. |
| 5,658,878 A | 8/1997 | Backstrom et al. |
| 5,672,581 A | 9/1997 | Rubsamen et al. |
| 5,693,338 A | 12/1997 | Milstein |
| 5,740,794 A | 4/1998 | Smith et al. |
| 5,747,445 A | 5/1998 | Backstrom et al. |
| 5,785,049 A | 7/1998 | Smith et al. |
| 5,874,064 A | 2/1999 | Edwards et al. |
| 5,877,174 A | 3/1999 | Ono et al. |
| 5,888,477 A | 3/1999 | Gonda et al. |
| 5,901,703 A | 5/1999 | Ohki et al. |
| 5,952,008 A | 9/1999 | Backstrom et al. |
| 5,976,569 A | 11/1999 | Milstein |
| 5,997,848 A | 12/1999 | Patton et al. |
| 6,006,753 A | 12/1999 | Efendic |

(Continued)

FOREIGN PATENT DOCUMENTS

| | | |
|---|---|---|
| EP | 220958 | 5/1987 |
| EP | 257915 | 2/1988 |

(Continued)

OTHER PUBLICATIONS

ONdrug Delivery (2006) "Pulmonary Delivery", pp. 1-22.*
Tornusciolo et al., Biotechniques 19(5):800-805, 1995. Simultaneous detection of TDT-mediated dUTP-biotin nick end-labeling (TUNEL)-positive cells and multiple immunohistochemical markers in single tissue sections.
Vahl et al. "Effects of GLP-1-7 36)NH2, GLP-1-(7-37), and GLP-1-(9-36)NH2 on intravenous glucose tolerance and glucose-induced insulin secretion in healthy humans." J Clin Endocrinol Metab 88:1772, 2003.

(Continued)

*Primary Examiner* — Karen Cochrane Carlson
*Assistant Examiner* — Samuel Liu
(74) *Attorney, Agent, or Firm* — K&L Gates LLP; Louis C. Cullman; Hal Gibson

(57) ABSTRACT

A method for treating migraines is disclosed. The method utilizes a rapid drug delivery system which prevents deactivation or degradation of the active agent, including small molecules and peptides being administered to a patient in need of treatment. In particular, the drug delivery system is designed for inhalation for delivery of drugs to the pulmonary circulation in a rapid and therapeutically effective manner.

13 Claims, 23 Drawing Sheets

(56) References Cited

U.S. PATENT DOCUMENTS

| | | | |
|---|---|---|---|
| 6,063,910 A | 5/2000 | Debenedetti et al. |
| 6,071,497 A | 6/2000 | Steiner et al. |
| 6,132,766 A | 10/2000 | Sankaram et al. |
| 6,153,613 A | 11/2000 | Ono et al. |
| 6,187,291 B1 | 2/2001 | Weinstein et al. |
| 6,191,102 B1 | 2/2001 | DiMarchi et al. |
| 6,277,819 B1 | 8/2001 | Efendic |
| 6,331,318 B1 | 12/2001 | Milstein |
| 6,335,316 B1 | 1/2002 | Hughes et al. |
| 6,348,447 B1 | 2/2002 | Hellstrom et al. |
| 6,358,924 B1 | 3/2002 | Hoffmann |
| 6,380,357 B2 | 4/2002 | Hermeling et al. |
| 6,388,053 B1 | 5/2002 | Galloway et al. |
| 6,395,774 B1 | 5/2002 | Milstein |
| 6,410,513 B1 | 6/2002 | Galloway et al. |
| 6,428,771 B1 | 8/2002 | Steiner et al. |
| 6,440,463 B1 | 8/2002 | Feldstein et al. |
| 6,444,226 B1 | 9/2002 | Steiner et al. |
| 6,447,751 B1 | 9/2002 | Weinstein et al. |
| 6,555,521 B2 | 4/2003 | Hermeling et al. |
| 6,583,111 B1 | 6/2003 | DiMarchi et al. |
| 6,652,838 B2 | 11/2003 | Weinstein et al. |
| 6,652,885 B2 | 11/2003 | Steiner et al. |
| 6,660,716 B1 | 12/2003 | Yakubu-Madus et al. |
| 6,720,407 B1 | 4/2004 | Hughes et al. |
| 6,747,006 B2 | 6/2004 | Efendic |
| 6,923,175 B2 | 8/2005 | Poole et al. |
| 6,989,155 B1 | 1/2006 | Ganderton et al. |
| 7,022,674 B2 | 4/2006 | DeFelippis et al. |
| 7,084,243 B2 | 8/2006 | Glaesner et al. |
| 7,101,843 B2 | 9/2006 | Glaesner et al. |
| 7,144,863 B2 | 12/2006 | DeFelippis et al. |
| 7,179,788 B2 | 2/2007 | DeFelippis et al. |
| 7,211,557 B2 | 5/2007 | DiMarchi et al. |
| 7,223,728 B2 | 5/2007 | Yabuku-Madus et al. |
| 7,232,897 B2 | 6/2007 | Hotamisligil et al. |
| 7,238,663 B2 | 7/2007 | DeFelippis et al. |
| 7,259,233 B2 | 8/2007 | Dodd et al. |
| 7,278,419 B2 | 10/2007 | Gonda et al. |
| 7,279,457 B2 | 10/2007 | Pohl et al. |
| 7,305,986 B1 | 12/2007 | Steiner et al. |
| 7,314,859 B2 | 1/2008 | Green et al. |
| 7,464,706 B2 | 12/2008 | Steiner et al. |
| 7,625,865 B2 | 12/2009 | Colombo et al. |
| 7,648,960 B2 | 1/2010 | Steiner et al. |
| 7,943,178 B2 | 5/2011 | Steiner et al. |
| 8,119,593 B2 | 2/2012 | Richardson |
| 8,389,470 B2 | 3/2013 | Steiner |
| 2002/0052381 A1 | 5/2002 | Bar-Or et al. |
| 2002/0065239 A1 | 5/2002 | Caplan et al. |
| 2003/0017211 A1 | 1/2003 | Steiner |
| 2004/0038865 A1 | 2/2004 | Gelber et al. |
| 2004/0053819 A1 | 3/2004 | Dodd |
| 2004/0062722 A1 | 4/2004 | Gonda et al. |
| 2004/0096403 A1 | 5/2004 | Steiner |
| 2004/0121964 A1 | 6/2004 | Madar et al. |
| 2004/0182387 A1 | 9/2004 | Steiner et al. |
| 2005/0043228 A1 | 2/2005 | DeFelippis et al. |
| 2005/0153874 A1 | 7/2005 | Cheatham et al. |
| 2006/0040953 A1 | 2/2006 | Leone-Bay et al. |
| 2006/0041133 A1 | 2/2006 | Stevenson et al. |
| 2006/0099269 A1 | 5/2006 | Cheatham et al. |
| 2006/0120969 A1 | 6/2006 | Nilsson et al. |
| 2006/0153778 A1 | 7/2006 | Gelber et al. |
| 2006/0239934 A1 | 10/2006 | Cheatham et al. |
| 2007/0020191 A1 | 1/2007 | Boss et al. |
| 2007/0027063 A1 | 2/2007 | Boss et al. |
| 2007/0059373 A1 | 3/2007 | Oberg |
| 2007/0059374 A1 | 3/2007 | Hokenson et al. |
| 2007/0191462 A1* | 8/2007 | Hettiarachchi et al. ........ 514/416 |
| 2007/0196503 A1 | 8/2007 | Wilson et al. |
| 2007/0207958 A1 | 9/2007 | Bridon et al. |
| 2008/0260838 A1 | 10/2008 | Hokenson et al. |
| 2008/0260840 A1* | 10/2008 | Alessi et al. .................. 424/489 |
| 2009/0110647 A1 | 4/2009 | Richarson |
| 2009/0111749 A1 | 4/2009 | Richardson et al. |
| 2009/0258818 A1 | 10/2009 | Surolia et al. |
| 2009/0308390 A1 | 12/2009 | Smutney et al. |
| 2010/0086609 A1 | 4/2010 | Steiner et al. |
| 2010/0113363 A1 | 5/2010 | Holst et al. |
| 2011/0183901 A1 | 7/2011 | Cheatham |
| 2012/0040899 A1 | 2/2012 | Costello |
| 2012/0094905 A1 | 4/2012 | Costello |
| 2012/0115777 A1 | 5/2012 | Richardson |
| 2013/0125886 A1 | 5/2013 | Richardson |

FOREIGN PATENT DOCUMENTS

| | | |
|---|---|---|
| EP | 1364967 | 11/2003 |
| EP | 1 598 066 A1 | 11/2005 |
| EP | 2060268 | 5/2006 |
| GB | 2240337 | 7/1991 |
| JP | 363020301 | 1/1988 |
| JP | 2-149545 | 2/1992 |
| JP | 09-208485 | 8/1997 |
| JP | 2003-503420 | 1/2003 |
| WO | 91/04011 | 4/1991 |
| WO | 92/08509 | 5/1992 |
| WO | 93/02712 | 2/1993 |
| WO | 94/08552 | 4/1994 |
| WO | 95/00127 | 1/1995 |
| WO | 96/36314 | 11/1996 |
| WO | 97/46206 | 12/1997 |
| WO | 99/52506 | 10/1999 |
| WO | 01/00654 | 1/2001 |
| WO | 02/098348 | 12/2002 |
| WO | 2004/103304 A2 | 12/2004 |
| WO | 2005/067964 | 7/2005 |
| WO | 2006/023943 | 3/2006 |
| WO | 2007/030706 | 3/2007 |
| WO | 2007/033316 | 3/2007 |
| WO | 2007/100535 | 9/2007 |
| WO | 2007/121411 | 10/2007 |
| WO | 2009/055742 | 4/2009 |
| WO | 2011/163272 | 12/2011 |

OTHER PUBLICATIONS

Vara et al. "Glucagon-like peptide-1 (7-36) amide stimulates surfactant secretion in human type II pneumocytes." Am J Resp Crit Care Med 163:841, 2001.

Vella et al. "Effect of glucagon-like peptide 1(7-36) amide on glucose effectiveness and insulin action in people with type 2 diabetes." Diabetes 49:611, 2000.

Vella et al. "The gastrointestinal tract and glucose tolerance." Curr Opin Clin Nutr Metab Care 7:479, 2004.

Verdich et al., A meta-analysis of the effect of glucagon-like peptide-1 (7-36) amide on ad libitum energy intake in humans. J Clin Endocrinol Metab., 86:4382-4389, 2001.

Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.

Vilsboll et al., "Evaluation of β-Cell Secretary Capacity Using Glucagon-Like Peptide 1", Diabetes Care, vol. 23, No. 6, pp. 807-812, Jun. 2000.

Vilsboll et al. "Reduced postprandial concentrations of intact biologically active glucagon-like peptide-1 in type 2 diabetic patients." Diabetes 50:609, 2001.

Vilsboll et al. "Similar elimination rates of glucagon-like peptide-1 in obese type 2 diabetic patients and healthy subjects." J Clin Endocrinol Metab 88:220, 2003.

Wachters-Hagedoorn et al. "The rate of intestinal glucose absorption is correlated with plasma glucose-dependent insulinotropic polypeptide concentrations in healthy men." J Nutr 136:1511, 2006.

Wang et al. J. Clin. Invest., 95:417-21, 1995.

Wang et al., Glucagon-like peptide-1 regulates proliferation and apoptosis via activation of protein kinase B in pancreatic INS-1 beta cells. Diabetologia, 47:478-487, 2004.

Wei et al. "Tissue-specific expression of the human receptor for glucagon-like peptide-1: brain and pancreatic forms have the same deduced amino acid sequence." FEBS Letters 358:219, 1995.

(56) References Cited

OTHER PUBLICATIONS

Weir et al. "Glucagonlike peptide 1 (7-37) actions on endocrine pancreas." Diabetes 38:338, 1989.
Wettergren et al. "Truncated GLP-1 (proglucagon 78-107-Amide) inhibits gastric and pancreatic functions in man." Digestive Diseases and Sciences 38:665, 1993.
Willms et al. "Gastric emptying, glucose responses, and insulin secretion after a liquid test meal: effects of exogenous glucagon-like peptide-1 (GLP-1) (7-36) amide in type 2 (noninsulin-dependent) diabetic patients." J. Clin Endocrinol Metab 81:327, 1996.
Wilson et al. "Technospheres(TM) for pulmonary and nasal applications." Respiratory Drug Delivery VIII, 2002, p. 545.
Wong et al. "From cradle to grave: pancreatic b-cell mass and glucagon-like peptide-1." Minerva Endocrinologica 31:107, 2006.
Yusta et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Ahren et al. "Characterization of GLP-1 effects on b-cell function after meal ingestion in humans." Diabetes Care 26:2860, 2003.
Ahren "GLP-1 and extra-islet effects." Horm Med Res 36:842, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon0like peptide-1." Treat Endocrinol 1:117, 2002.
Baggio et al. "A recombinant human glucagon-like peptide (GLP)-1-albumin protein (Albugon) mimics peptidergic activation of GLP-1 receptor-dependent pathways coupled with satiety, gastrointestinal motility, and glucose homeostatsis." Diabetes 53:2492, 2004.
Balkan et al. "Portal GLP-1 administration in rats augments the insulin response to glucose via neuronal mechanisms." Am J. Physiol Regulatory Integrative Comp Physiol 279:R1449, 2000.
Barnett et al. "An open, randomized, parallel-group study to compare the efficacy and safety profile of inhaled human insulin (Exubera) with glibenclamide as adjuvant therapy in patients with Type 2 diabetes poorly controlled on metformin." Diabetes Care 29:1818, 2006.
Barnett et al. "An open, randomized, parallel-group study to compare the efficacy and safety profile of inhaled human insulin (Exubera) with metformin as adjuvant therapy in patients with Type 2 diabetes poorly controlled on a sulfonylurea." Diabetes Care 29:1282, 2006.
Barragan et al. "Changes in arterial blood pressure and heart rate induced by glucagon-like peptide-1-(7-36) amide in rates." Am J. Physiol 266 (Endocrinol Metab 29):E459, 1994.
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Benito et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Blazquez et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Bray "Exanatide" Am J Health-Sys Pharm 63:411, 2006.
Bullock et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.

Campos et al. "Divergent tissue-specific and developmental expression of receptors for glucagon and glucagon0like peptide-1 in the mouse." Endocrinology 134:2156, 1994.
Ceglia et al. "Meta-analysis: efficacy and safety of inhaled insulin therapy in adults with diabetes mellitus." Ann Intern Med 145:665, 2006.
Cernea et al. "Noninjectable methods of insulin administration." Drugs of Today 42:405, 2006.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Coffey et al. "Valuing heath-related quality of life in diabetes." Diabetes Care 25:2238, 2002.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., J. Clin. Invest., 97:133-38, 1996.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
De Heer et al. "Sulfonylurea compounds uncouple the glucose dependence of the insulinotropic effect of glucagon-like peptide-1." Diabetes 56:438, 2007.
Delgado-Aros et al. "Effect of GLP-1 on gastric volume, emptying, maximum volume ingested and postprandial symptoms in humans." Am J Physiol Gastrointest Liver Physiol 282:G424, 2002.
Doyle et al. "Glucagon-like peptide-1." Recent Prog Horm Res. 2001;56:377-99.
Drucker "Development of glucagon-like peptide-1-based pharmaceuticals as therapeutic agents for the treatment of diabetes." Curr Pharma Design 7:1399, 2001.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Edwards et al. "Cardiovascular and pancreatic endocrine response to glucagon-like peptide-1(7-36) amide in the conscious calf." Exp Physiol 82:709, 1997.
Edwards et al. "Subcutaneous glucagon-like peptide-1(7-36) amide is insulinotropic and can cause hypoglycaemia in fasted healthy subjects." Clinical Science 96:719, 1998.
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Life Sci., 55:629-34, 1994.
Elrick et al. "Plasma insulin response to oral and intravenous glucose administration." J Clin Endocr 24:1076, 1964.
Fehmann et al. "Cell and molecular biology of the incretin hormones glucagon-like peptide-1 and glucose-dependent insulin releasing polypeptide." Endocrine Reviews 16:390, 1995.
Goke et al., J. Biol. Chem. 268:19650-55, 1993.
Golpon et al. "Vasorelaxant effect of glucagon-like peptide-(7-36) amide and amylin on the pulmonary circulation of the rat." Regulatory Peptides 102:81, 2001.
Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Gutniak et al. "Antidiabetogenic effect of glucagon-like peptide-1 (7-36)amide in normal subjects nad patients with diabetes mellitus." NEJM 326:1316, 1992.
Gutniak et al. "Subcutaneious injection of the incretin hormone glucagon-like peptide 1 abolishes postprandial glycemia in NIDDM." Diabetes Care 17:1039, 1994.
Gutniak et al. "Potential therapeutic levels of glucagon-like peptide I achieved in humans by a buccal tablet." Diabetes Care 19:843, 1996.
Gutniak et al. "GLP-1 tablet in type 2 diabetes in fasting and postprandial conditions." Diabetes Care 20:1874, 1997.
Gutniak et al. "Antidiabetogenic action of glucagon-like peptide-1 related to administration relative to meal intake in subjects with type 2 diabetes." J Int Med 250:81, 2001.

(56) References Cited

OTHER PUBLICATIONS

Guyton et al., "Acute Control of Llocal Blood Flow", Textbook of Medical Physiology, Chapter 17, 10th Edition, W.B. Saunders Company, pp. 176-177, 2000.
Haak "New developments in the treatment of type 1 diabetes mellitus." Exp Clin Endocrinol Diabetes 107:Suppl 3: S108, 1999.
Hassan et al. "In vivo dynamic distribution of 131I-glucagon0like peptide-1 (7-36) amide in the rat studied by gamma camera." Nucl Med Biot 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
M. Combettes, and Kargar, C., "Newly Approved and Promising Antidiabetic Agents," Therapie, Jul.-Aug. 2007; 62 (4): 293-310.
Office Action issued in connection with Russian Application No. 2010120666 mailed on Apr. 27, 2012.
Hayasaka et al. "Proliferation of type II pneumocytes and alteration in their apical surface membrane antigenicity in pulmonary sarcoidosis." Chest 116:477, 1999.
Heine "Unlocking the opportunity of tight glycaemic control. Promise ahead: the role of inhaled insulin in clinical practice." Diabetes, Obesity and Metabolism 7:S19, 2005.
Heinemann et al. "Time-action profile of inhaled insulin." Diabetic Med 14:63, 1996.
Heinemann et al. "Current status of the development of inhaled insulin." Br J Diabetes Vasc Dis 4:, 2004.
Heise et al. "The effect of insulin antibodies on the metabolic action of inhaled and subcutaneous insulin." Diabetes Care 28:2161, 2005.
Hite et al. "Exhuberance over Exubera." Clinical Diabetes 24:110, 2006.
Hollander et al. "Efficacy and safety of inhaled insulin (Exubera) compared with subcutaneous insulin therapy in patients with type 2 diabetes." Diabetes Care 27:2356, 2004.
Holst et al. "On the effects of glucagon-like peptide-1 on blood glucose regulation in normal and diabetic subjects." Ann N Y Acad Sci. Dec. 26, 1996;805:729-36.
Holst "Therapy of type 2 diabetes mellitus based on the actions of glucagon-like peptide-1." Diabetes Metab Res Rev 18:430, 2002.
Huda et al. "Gut peptides and the regulation of appetite." Obesity Reviews 7:163, 2006.
Imeryuz et al. "Glucagon-like peptide-1 inhibits gastric emptying via vagal afferent-mediated central mechanisms." Am J Physiol 273 (Gastrointest Liver Physiol 36):G920, 1997.
Johnson et al: RyR2 and calpain-10 delineate a novel apoptosis pathway in pancreatic islets. J Biol Chem., 279 (23):24794-802, 2004.
Johnson et al. "Peptide turn mimetics." in Biotechnology and Pharmacy, Ed JM Pezzuto et al. Chapman & Hall, New York, pp. 366, (1993).
Joseph et al. "Oral delivery of glucagon-like peptide-1 in a modified polymer preparation normalizes basal glycaemia in diabetic db/db mice." Diabetologia 43:1319, 2000.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200, 1996.
Kanse et al. "Identification and characterization of glucagon-like peptide-1 7-36 amide-binding sites in the rat brain and lung." FEBS Letters 241:209, 1988.
Kapitza et al. "Impact of particle size and aerosolization time on the metabolic effect of an inhaled insulin aerosol." Diabetes Tech Ther 6:119, 2004.
Katchalski et al. "Synthesis of lysine anhydride." 879, 1946.
Kawai et al. "Evidence that glucagon stimulates insulin secretion through its own receptor in rats." Diabetologia 38:274, 1995.
Kenny et al. "Dipeptidyl peptidase IV, a kidney brush-border serin peptidase." Biochem J. 155:169, 1976.
Kieffer et al. "The glucagon-like peptides." Endocrine Reviews 20:876, 1999.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between african-american and non-hispanic white adults with diabetes." Diabetes Care 29:2130, 2006.
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Komatsu et al. "Glucagonostatic and insulinotropic action of glucagon-like peptide-1 (7-36)-amide." Diabetes 38:902, 1989.
Kopple et al. "A convenient synthesis of 2,5-piperazinediones." J Org Chem p. 962, 1967.
Kreymann et al. "Glucagon-like peptide-1 7-36: a physiological incretin in man." The Lancet, Dec. 5, 1987, p. 1300.
Kwon et al. "Signaling elements involved in the metabolic regulation of mTOR by nutrients, incretins, and growth factors in islets." Diabetes 53:S225, 2004.
Lankat-Buttgereit et al. "Molecular cloning of a cDNA encoding for the GLP-1 receptor expressed in rat lung." Exp Clin Endocrinol 102:241, 1994.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Leone-Bay et al. "Evaluation of novel particles as an inhalation system for GLP-1." Diabetes, Obesity and Metabolism. 11:1050-1059, 2009.
Li et al. "GLP-1; a novel zinc finger protein required in somatic cells of the gonad for germ cell development." Dev Biol 301:106, 2007.
Luque et al. "Glucagon-like peptide-1 (GLP-1) and glucose metabolism in human myocytes." J. Endocrinol 173:465, 2002.
Malhotra et al., Regulatory Peptides, 41:149-56, 1992.
Marshall "Preventing and detecting complications of diabetes." BMJ 333:455, 2006.
Matsui et al. "Hyperplasia of type II pneumocytes in pulmonary lymphangioleiomyomatosis. Immunohistochemical and electron microscope study." Arch Pathol Lab Med 124:1642, 2000.
McElduff et al. "Influence of acute upper respiratory tract infection on the absorption of inhaled insulin using the AERx(R) insulin diabetes management system." Br J Clin Pharmacol 59:546, 2005.
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Montrose-Rafizadeh et al., Diabetes, 45(Suppl. 2):152A, 1996.
Narayan et al. "Impact of recent increase in incidence on future diabetes burden." Diabetes Care 29:2114, 2006.
Naslund et al. "GLP-1 slows solid gastric emptying and inhibits insulin, glucagon, and PYY release in humans." Am J Physiol (Regulatory Integrative Comp Physiol 46):R910, 1999.

(56) References Cited

OTHER PUBLICATIONS

Naslund et al. "Prandial subcutaneous injections of glucagon-like petide-1 cause weight loss in obese human subjects." Br J Nutrition 91:439, 2004.
Nauck et al. "Reduced incretin effect in type 2 (non-insulin-dependent) diabetes." Diabetologia 29:46, 1986.
International Search Report for PCT/US2011/060057 mailed on Jan. 20, 2012.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Moren, Aerosols in Medicine (2nd Ed.), Elsevier, pp. 321-350, (1993).
Nathan et al. "Intensive diabetes treatment and cardiovascular disease in patients with Type 1 diabetes." New Eng. J. Med. 353:2643-2653, 2005.
Nathan et al. "Management of hyperglycemia in Type 2 diabetes: a consensus algorithm for the initiation and adjustment of therapy." Diabetes Care 29:1963, 2006.
Nathan et al. "Management of hyperglycemia in Type 2 diabetes: a consensus algorithm for the initiation and adjustment of therapy." Diabetes Care 31:173, 2008.
Nathan et al. "Management of hyperglycemia in Type 2 diabetes: a consensus algorithm for the initiation and adjustment of therapy." Diabetes Care 32:193, 2009.
Okumura et al., Intratracheal delivery of insulin: absorption from solution and aerosol by rat lung. Int. J. Pharmaceuticals 88: 63-73 (1992).
Owens et al. "Inhaled human insulin." Nature Reviews, Drug Discovery, vol. 5, No. 5, pp. 371-372, May 2006.
Patton & Platz, Routes of Delivery: Case studies: pulmonary delivery of peptides and proteins for systemic action. Adv. Drug. Del. Rev. 8: 179-196 (1992).
Perera et al., Absorption and Metabolic Effect of Inhaled Insulin. Diabetes Care, vol. 25, No. 12, Dec. 2002, p. 2276-2281.
Pfeiffer Ma et al. Insulin secretion in diabetes mellitus. Am J Med 70:579-88, 1981.
Pfutzner et al "Technosphere/Insulin—A New Approach for Effective Delivery of Human Insulin Via the Pulmonary Route." Dibetes Technology & Therapeutics, vol. 4, No. 5, 2002, pp. 589-594.
Polonsky et al. Abnormal patterns of insulin secretion in non-insulin-dependent diabetes mellitus. N Eng J Med 318:1231-39, 1988.
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.
Raz I et al. "Pharmacodynamics and pharmacokinetics of dose ranging effects of Oralin versus s.c. regular insulin in Type 1 diabetic patients." Fourth Annual Diabetes Technology Meeting, Philadelphia, PA, 2004.
Richardson et al. "Technosphere Insulin Technology." Diabetes Technology & Therapeutics, vol. 9, Supplement 1, pp. S-65, 2007.
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, Aug. 2008.
Sajeesh et al., Cyclodextrin-insulin complex encapsulated polymethacrylic acid based nanoparticles for oral insulin delivery. International Journal of Pharmaceuticals, 2006, 325, pp. 147-154.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Sawhney, Bioerodible hydrogels based on photopolymerized poly-(ethylene glycol)-co-poly(a-hydroxy acid) diacrylate macromere. Macromolecules, 26: 581-587 (1993).
Skyler "Pulmonary Insulin Delivery—State of the Art 2007." Diabetes Tecnology & Therapeutics, vol. 9, Supplement 1, pp. S1-S3. 2007.
Steiner S et al. Technosphere(TM)/Insulin—proof of concept study with a new insulin formulation for pulmonary delivery. Exp Clin Endocrinol Diabetes 110:17-21, 2002.
Strack "Inhaled Human Insulin." Drugs of Today 2006, 42 (4): 207-221.
Tack Cees J. et al., Forced Titration to Different Doses of Technosphere Insulin Demonstrates Reduction in Postprandial Glucose Excursions and Hemoglobin A1c in Patients with Type 2 Diabetes. Journal of Diabetes Science and Technology, vol. 2, Issue 1, pp. 47-57, Jan. 2008.
US Office Action cited in Appl. No. 12/985,197 mailed on Jan. 20, 2012.
Volund "Conversion of insulin units to SI units." American Journal of Clinical Nutrition, Nov. 1993, 58(5), pp. 714-715.
Warren et al. "Postprandial versus preprandial dosing of biphasic insulin apart in elderly type 2 diabetes patients." Diabetes Research and Clinical Practive, vol. 66, pp. 23-29, 2004.
Wigley et al., Insulin across respiratory mucosae by aerosol delivery. Diabetes 20(8): 552-556 (1971).
Witchert, Low molecular weight PLA: A suitable polymer for pulmonary administered microparticles. J. Microencapsulation, 10(2): 195-207 (1993).
Yoshida et al., Absorption of insulin delivered to rabbit trachea using aerosol dosage form. J. Pharm. Sci. 68(5): 670-671 (1979).
Actos Product Insert. Aug. 2008.
Alabraba et al. Diabetes Technology & Therapeutics. Jul. 2009, 11(7): 427-430.
American Diabetes Association. "Standards of medical care in diabetes—2009." Diabetes Care. Jan. 2009;32 Suppl 1: S13-61.
Avandia Product Insert, Oct. 2008.
Benita, Charaterization of Drug-Loaded Poly(d,I-lactide) Microspheres. J. Pharm. Sci., 73: 1721-1724 (1984).
Bensch et al. Absorption of intact protein molecules across the pulmonary air-tissue barrier, Science 156: 1204-1206 (1967).
Biodel's Intellecutal Property position strengthened for ultra-rapid-acting insulin programs by notice of intent to grant from European Patent Office. Newswire Fee, published May 2, 2012.
Boss et al. "Prandial Insulin: Is Inhaled Enough?" Drug Development Research 69(3):138-142 (2008).
Brownlee et al. "Glycemic variability: a hemoglobin A1c-independent risk factor for diabetic complications." JAMA 295:1707, 2006.
Cefalu et al., Concept, strategies and feasibility of noinvasive insulin delivery. Diabetes Care 27: 239-246, (2004).
Cefalu et al., Inhaled human insulin treatment in patients with type 2 diabetes mellitus. Ann. Int. Med., 2001, 134, 203-7.
Cerasi et al., Decreased sensitivity of the pancreatic beta cells to glucose in prediabetic and diabetic subjects. A glucose dose-response study. Diabetes 21 (4): 224-34, 1974.
Cernea et al. "Dose-response relationship of oral insulin spray in healthy subjects." Diabetes Care, vol. 28, No. 6, pp. 1353-1357, Jun. 2005.
Cheatham et al. "Desirable dynamics & performance of inhaled insulin compared to subcutaneous insulin given at mealtime in type 2 diabetes: A report from the technosphere/insulin study group." pp. 234-235, 2004.

(56) References Cited

OTHER PUBLICATIONS

Cheatham et al., Desirable dynamics and performance of inhaled insulin compared to subcutaneous insulin given at mealtime in type 2 diabetes: A report from the technosphere/insulin study group. Diabetes Technology and Therapeutics, vol. 6, p. 234, 2004.
Clee et al. Nature Genetics 38:688-693, 2006.
Cobble "Initiating and Intensifying Insulin Therapy for Type 2 Diabetes: Why, When, and How." Am J Ther. Jan. 8, 2009.
Davis "Postprandial Physiology and the Pathogenesis of Type 2 Diabetes Mellitus." Insulin, vol. 3, Apr. 1, 2008, pp. 132-140.
Decode study group. "Glucose tolerance and mortality: comparison of WHO and American Diabetes Association diagnostic criteria." Lancet. Aug. 21, 1999;354(9179):617-21.
Edelman SV Type II diabetes mellitus. Adv Int Med 43:449-500, 1998.
Elliot et al., Parenteral absorption of insulin from the lung in diabetic children. Austr. Paediatr. J. 23: 293-297 (1987).
Engwerda et al., Improved pharmackinetic and pharmacodynamic profile of rapid-acting insulin using needle-free jet injection technology. Diabetes Care, vol. 34, Aug. 2011, pp. 1804-1808.
EP Office Action, Application No. 10 005 945.0 mailed Dec. 28, 2011.
Farr, S.J. et al., Pulmonary insulin administration using the AERx®system:physiological and physiochemical factors influencing insulin in effectiveness in healthy fasting subjects. Diabetes Tech. Ther. 2:185-197, 2000.
Glucophage Product Insert. Jan. 2009.
Glucotrol Product Insert. Sep. 2006.
Gupta, Contemporary Approaches in Aerosolized Drug Delivery to the Lung. J. Controlled Release, 17(2): 127-147 (1991).
Halozyme Press Release. Jun. 6, 2009.
Hausmann et al. "Inhaled insulin as adjunctive therapy in subjects with type 2 diabetes failing oral agents: a controlled proof-of-concept study." Diabetes Obesity Metab 8:574-580, 2006.
Heinemann "Variability of Insulin Absorption and Insulin Action." Diabetes Technology & Therapeutics, vol. 4, No. 5, pp. 673-682. 2002.
Heyder, Alveolar deposition of inhaled particles in humans. Am. Ind. Hyg. Assoc. J. 43(11): 864-866 (1982).
Hussain et al., State of insulin self-association does not affects its absorption from the pulmonary route. Eur. J. Pharm. Sciences 25: 289-298, 2005.
Iwanij et al., Characterization of the Glucagon Receptor and its Functional Domains Using Monoclonal Antibodies. The Journal of Biological Chemistry, vol. 265, No. 34, pp. 21302-21308, 1990.
Japanese Office Action for related case 2008-504512 issued Sep. 15, 2011.
Jones et al., An investigation of the pulmonary absorption of insulin in the rat. Third European Congress of Biopharmaceutics and Pharmacokinetics, (1987).
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Nε-(Fumaroyl)diketopiperazine of L-Lys (FDKP) Interactions." Molecular Pharmaceutics, vol. 5, No. 2, 294-315, 2008.
Kohler D et al. Non-radioactive approach for measuring lung permeability: inhalation of insulin. Atemw Lungenkrkh 13:230-232, 1987. (Original German and English translation attached).
Komada et al., Intratracheal delivery of peptide and protein agents: absorption from solution and dry powder by rat lung. J. Pharm. Sci. 83(6): 863-867 (1994).
Kopple, A convenient synthesis of 2,5-piperazinediones. J. Org. Chem. 33(2): 862-864 (1968).
Leahy et al., Beta-cell dysfunction in type 2 diabetes mellitus. Curr. Opin. Endocrinol. Diabetes, 2: 300-306, 1995.

Lian et al., A self-complementary self-assembling microsphere system: application for intravenous delivery of the antiepileptic andneuroprotectant compound felbanate. J. Pharm Sci. 89: 867-875, 2000.
Lim, Microencapsulation of Living Cells and Tissues. J. Pharm. Sci., 70: 351-354 (1981).
MannKind Corporation "Postprandial hyperglycemia: clinical significance, pathogenesis and treatment." MannKind Corporation Monograph. 2009.
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matthews et al. "Homeostasis model assessment: insulin resistance and beta-cell function from fasting plasma glucose and insulin concentrations in man." Diabetologia. Jul. 1985;28(7):412-9.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck "Is glucagon-like peptide 1 an incretin hormone?" Diabetologia 42:373, 1999.
Nauck et al., Normalization of fasting hyperglycemia by exogenous GLP-1 (7-36 amide) in type 2 diabetic patients. Diabetologia, 36:741-744, 1993.
Nauck et al., Effects of subcutaneous glucagon-like peptide 1 (GLP-1 [7-36 amide]) in patients with NIDDM. Diabetologia, 39:1546-1553, 1996.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nystrom et al. "Effects of glucagon-like peptide-1 on endothelial function in type 2 diabetic patients with stable coronary artery disease." Am J Physiol Endocrinol Metab 287:E1209, 2004.
Oshima et al. "Comparison of half-disappearance times, distribution volumes and metabolic clearance rates of exogenous glucagon-like peptide 1 and glucagon in rats." Regulatory Peptides 21:85, 1988.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Patton "Mechanisms of macromolecule absorption by the lungs." Advanced Drug Delivery Reviews 19:3, 1996.
Patton et al. "The lungs as a portal of entry for systemic drug delivery." Proc Am Thorac Soc 1:338, 2004.
Patton "Unlocking the opportunity of tight glycaemic control. Innovative delivery of insulin via the lung." Diabetes Obesity and Metabolism 7:S5, 2005.
Quattrin et al. "Efficacy and safety of inhaled insulin (Exubera) compared with subcutaneous insulin therapy in patients with type 1 diabetes." Diabetes Care 27:2622, 2004.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raufman et al., J. Biol. Chem. 267:21432-37, 1992.
Raufman et al., J. Biol. Chem. 266:2897-902, 1991.
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Time-action profile of inhaled insulin in comparison with subcutaneously injected insulin lispro and regular human insulin." Diabetes Care 28:1077, 2005.

(56) References Cited

OTHER PUBLICATIONS

Razavi et al. "TRPVI+ sensory neurons control beta cell stress and islet inflammation in autoimmune disease." Cell 127:1123, 2006.
Richter et al. "Characterization of receptors for glucagon-like peptide-1 (7-36)amide on rat lung membranes." FEBS Letters 267:78, 1990.
Richter et al. "Characterization of glucagon-like peptide-1(7-36)amide receptors of rat membranes by covalent cross-linking." FEBS Letters 280:247, 1991.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosenstock et al. "Inhaled insulin improves glycemic control when substituted for or added to oral combination therapy in type 2 diabetes." Annals Int Med 143:549, 2005.
Saraceni et al. "Effects of glucagon-like peptide-1 and long-acting analogues on cardiovascular and metabolic function." Drugs R D 8:145, 2007.
Savage et al., "Effects of peptide YY (PYY) on mouth to caecum intestinal transit time and on the rate of gastric emptying healthy volunteers", Gut, vol. 28, pp. 166-170, 1987.
Schaffer et al. "Assembly of high-affinity insulin receptor agonists and antagonists from peptide building blocks." PNAS 100:4435, 2003.
Schepp et al., Eur. J. Pharmacol., 69:183-91, 1994.
Scherbaum "Unlocking the opportunity of tight glycaemic control. Inhaled insulin: clinical efficacy." Diabetes Obesity and Metabolism 7:S9, 2005.
Schirra et al. "Gastric emptying and release of incretin hormones after glucose ingestion in humans." J Clin Invest 97:92, 1996.
Scrocchi et al. "Glucose intolerance but normal satiety in mice with a null mutation in the glucagon-like peptide 1 receptor gene." Nature Medicine 2:1254, 1996.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shojania et al. "Effect of quality improvement strategies for type 2 diabetes on glycemic control." JAMA 296:427, 2006.
Singh, et al., Regul. Pept. 53:47-59, 1994.
Smith et al. "New-onset diabetes and risk of all-cause and cardiovascular mortality." Diabetes Care 29:2012, 2006.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement, Abstract 1545-PO, 2000.
Stowell et al. "Development of GLP-1 Technosphere(TM) powder: an inhaled GLP-1 product." Diabetes Technology Meeting, San Francisco, Oct. 2007.
Sturis et al., British Journal of Pharmacology, 140,123 .132, 2003.
Tang-Christensen et al. "Central administration of GLP-1-(7-36) amide inhibits food and water intake in rats." Am J Physiol 271 (Regulatory Integrative Comp Physiol 40):R848, 1996.
Teeter et al. "Dissociation of lung function changes with humoral immunity during inhaled human insulin therapy." Am J Resp Crit Care Med 173:1194, 2006.
Thorens "Expression cloning of the pancreatic b-cell receptor for the gluco-incretin hormone glucagon-like peptide-1." PNAS 89:8641, 1992.
Thorens et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in on-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide 1 (GLP-1) could cause reactive hypoglcaemia." Diabetologia 41:1180, 1998.

* cited by examiner

METHOD AND COMPOSITION FOR TREATING MIGRAINES

CROSS-REFERENCE TO RELATED APPLICATIONS

This application claims the benefit of U.S. Provisional Application No. 61/412,339, filed Nov. 10, 2010, which is incorporated by reference herein in its entirety.

This application is also a continuation-in-part of U.S. patent application Ser. No. 12/258,341, filed on Oct. 24, 2008, which claims the benefit of U.S. Provisional Application Nos. 60/982,368 filed Oct. 24, 2007; 60/985,620 filed Nov. 5, 2007; 61/022,274 filed Jan. 18, 2008; 61/033,740 filed Mar. 4, 2008; 61/052,127 filed May 9, 2008; and 61/094,823 filed Sep. 5, 2008. The entire contents of each of these applications are incorporated by reference herein.

This application is also a continuation-in-part of PCT/US11/41303, filed on Jun. 21, 2011, which claims the benefit of U.S. provisional patent application No. 61/411,775, filed on Nov. 9, 2010 and U.S. Provisional Patent Application 61/357,039, filed Jun. 21, 2010. The entire contents of each of these applications are incorporated by reference herein.

TECHNICAL FIELD

Method and composition for treating migraine are disclosed. The method comprises administering a pharmaceutical formulation comprising a small molecule, including triptans such as sumatriptan to a patient in need of treatment using a drug delivery system for pulmonary inhalation. In particular, the drug delivery system comprises a breath powered dry powder inhaler for oral inhalation.

BACKGROUND

Drug delivery systems for the treatment of disease which introduce active ingredients into the circulation for the treatment of disease are numerous and include oral, transdermal, subcutaneous and intravenous administration. While these systems have been used for quite a long time and can deliver sufficient medication for the treatment of many diseases, there are numerous challenges associated with these drug delivery mechanisms. In particular, delivery of effective amounts of proteins and peptides to treat a target disease has been problematic. Many factors are involved in introducing the right amount of the active agent, for example, preparation of the proper drug delivery formulation so that the formulation contains an amount of active agent that can reach its site(s) of action in an effective amount.

The active agent must be stable in the drug delivery formulation and the formulation should allow for absorption of the active agent into the circulation and remain active so that it can reach the target site(s) of action at effective therapeutic levels while minimizing the amount of dose to be administered. Thus, in the pharmacological arts, drug delivery systems which can deliver a stable active agent are of utmost importance.

Making drug delivery formulations therapeutically suitable for treating disease depends on the characteristics of the active ingredient or agent to be delivered to the patient. Such characteristics can include in a non-limiting manner solubility, pH, stability, toxicity, release rate, and ease of removal from the body by normal physiologic processes. For example, in oral administration, if the agent is sensitive to acid, enteric coatings have been developed using pharmaceutically acceptable materials which can prevent the active agent from being released in the low pH (acid) of the stomach. Thus, polymers that are not soluble at acidic pH are used to formulate and deliver a dose containing acid-sensitive agents to the small intestine where the pH is neutral. At neutral pH, the polymeric coating can dissolve to release the active agent which is then absorbed into the enteric systemic circulation. Orally administered active agents enter the systemic circulation and pass through the liver. In certain cases, some portion of the dose is metabolized and/or deactivated in the liver before reaching the target tissues. In some instances, the metabolites can be toxic to the patient, or can yield unwanted side effects.

Similarly, subcutaneous and intravenous administration of pharmaceutically-active agents is not devoid of degradation and inactivation. With intravenous administration of drugs, the drugs or active ingredients can also be metabolized, for example in the liver, before reaching the target tissue. With subcutaneous administration of certain active agents, including various proteins and peptides, there is additionally degradation and deactivation by peripheral and vascular tissue enzymes at the site of drug delivery and during travel through the venous blood stream. In order to deliver a dose that will yield an acceptable quantity for treating disease with subcutaneous and intravenous administration of an active agent, dosing regimes will always have to account for the inactivation of the active agent by peripheral and vascular venous tissue and ultimately the liver.

SUMMARY

A method of introducing an active agent into the circulatory system of a mammal is disclosed herein. The method comprises a rapid drug delivery system which prevents deactivation or degradation of the active agent being administered to a patient in need of treatment. In particular, the drug delivery system is designed for pulmonary drug delivery such as by inhalation, for delivery of active agents to the pulmonary circulation in a therapeutically effective manner. In one embodiment, the drug delivery system has advantages over other methods of drug delivery, for example, oral, subcutaneous and intravenous administration of drug products such as proteins and peptides that are sensitive to enzymatic deactivation, or prevents other small molecules from degradation in the local peripheral and vascular tissue prior to reaching the target site.

In one embodiment disclosed herein, a method for providing an active agent to a patient in need thereof is disclosed comprising selecting an active agent subject to degradation in the patient wherein effectiveness of the active agent is reduced by the degradation; associating the active agent with a diketopiperazine to produce a pharmaceutical composition suitable for pulmonary inhalation; and providing the pharmaceutical composition to the patient so that the active agent reaches the target site with substantially no degradation or deactivation in therapeutically effective amounts at lower doses than standard dosing with other routes of administration.

Also disclosed herein is a method of treating disease comprising selecting a patient being treated with or a patient with a condition treatable by a labile active agent; providing a composition comprising the labile active agent in association with a diketopiperazine; and administering the composition to the patient via pulmonary inhalation; thereby treating the disease or condition.

In another embodiment, the drug delivery system avoids degradation of the active agent from first pass metabolism, wherein the active agent is administered into the arterial circulation in the lungs and is delivered to the target organ in therapeutically effective levels, by avoiding degradation that occurs in venous blood circulation, in peripheral tissue, in the gastrointestinal system or in the liver. In this embodiment, active agents can be delivered at lower concentrations than is required through other routes of administration. In a particular embodiment, the active agent is a small molecule including, molecules that bind to serotonin receptors and are serotonin receptor agonists. In one embodiment, the molecules induce vasoconstriction of blood vessels in the brain, relieve swelling and headaches. In one embodiment, the compositions are used for the treatment of moderate to severe headaches that interfere with a subject's performance of daily tasks, and showing symptoms of nausea, vomiting and sensitivity to light and noise.

In another embodiment, the diketopiperazine is 2,5-diketo-3,6-di(4-X-aminobutyl)piperazine; wherein X is selected from the group consisting of succinyl, glutaryl, maleyl, and fumaryl; or a pharmaceutically acceptable salt thereof. In another embodiment, the pharmaceutical composition is an inhalable dry powder formulation. In yet another embodiment, the inhalable dry powder formulation further comprises a pharmaceutically acceptable carrier or excipient.

In one embodiment, the inhalable dry powder formulation is provided to the patient by pulmonary inhalation using a dry powder inhalation system. In one embodiment, the system comprises a dry powder inhaler with or without a container and a dry powder formulation.

In an exemplary embodiment, a method is provided for treating a migraine headache, which method comprises administering to a patient in need of treatment a dry powder composition by oral inhalation; wherein the dry powder composition comprises an active agent for treating migraines, including, a triptan such as sumatriptan, almotriptan, eletriptan, frovatriptan, naratriptan, rizatriptan, zolmitriptan and pharmaceutically acceptable salts thereof, and a substituted diketopiperazine such as fumaryl diketopiperazine, or a salt of the diketopiperazine such as disodium fumaryl diketopiperazine. The dry powder composition can be administered to the patient at the time of onset of the migraine headache as needed by the patient or as determined and instructed by the physician. In one embodiment, the dose of the triptan can reduce or avoid unwanted side effects associated with injectable or tablet drug therapy, including, flushing, sweating, vertigo, fatigue, tingling, drowsiness, dizziness, dry mouth, heartburn, abdominal pain, abdominal cramps, weakness, feeling of warmth or coldness, bitter taste from tablets and nasal sprays, and local burning from injection site by proving a reduced amount of triptan required with other modes of administration.

In a particular embodiment, a method of treating symptoms associated with migraine comprises administering to a subject in need of said treatment a thereapeutically effective amount of a dry powder pharmaceutical composition by inhalation comprising a triptan, including, sumatriptan, almotriptan, eletriptan, frovatriptan, naratriptan, rizatriptan, zolmitriptan and pharmaceutically acceptable salts thereof, and a substituted diketopiperazine in a composition comprising bis [3,6-(N-fumaryl-4-aminobutyl)]-2,5-d iketopiperazine or bis [3,6-(N-fumaryl-4-aminobutyl)]-2,5-diketopiperazine disodium salt. In certain embodiments, the pharmaceutical composition can comprise a dry powder comprising a pharmaceutically acceptable carrier or other inactive agents. In some embodiments, the amount of triptans in the dry powder composition, for example, sumatriptan succinate can vary depending on the subject's requirements, for example, the triptan can be in amounts 1 mg or greater. In example embodiments, the amount of sumatriptan or a salt thereof, including, sumatriptan succinate in a powder for pulmonary inhalation can be administered in a range of from about 1 mg to about 50 mg. In another embodiment, the triptan is a salt of rizatriptan, including, but not limited to benzoate. In other embodiments, the triptan salts can be, for example, almotriptan malate, frovatriptan succinate, eletriptan hydrobromide, and naratriptan hydrochloride. In certain embodiments, the dry powder composition can optionally comprise an amino acid such an aliphatic amino acid, for example, alanine, glycine, leucine, isoleucine, norleucine at amounts ranging from about 0.5% to about 30% by weight. In one particular embodiment, the dry powder composition comprises the amino acid L-leucine. In some embodiments, a pharmaceutical composition may comprise microparticles, wherein a microparticle may comprise 1) a diketopiperazine, and at least one of: a serotonin receptor agonist, such as a triptan, and an aliphatic amino acid. A triptan, and/or an aliphatic amino acid may be incorporated into, adhered to, complexed with, or coated onto a diketopiperazine microparticle. In some embodiments, a diketopiperazine microparticle may be coated with at least one of a serotonin receptor agonist, such as a triptan, and an aliphatic amino acid.

In alternative embodiments, the method of treating a migrane headache can comprise a combination therapy administering a dry powder composition comprising a triptan by oral inhalation, and optionally, administering a second medication or drug, for example, selective serotonin reuptake inhibitor such as fluoxetine and duloxetine, which can be given by other routes of administration such as oral tablets or injections. In one embodiment, the combination therapy can comprise a dry powder composition comprising the triptan and one or more additional drug(s) that can be administered by inhalation.

In another embodiment of the disclosed method, the step of administering the composition to the patient comprises pulmonary administration of the dry powder composition by inhalation using a breath powered, dry powder inhaler with or without a container, wherein the container can be a cartridge, such as a unit dosing cartridge for a reusable inhaler, or a single use inhaler. In this and other embodiments, the dry powder inhaler system comprises a high resistance dry powder inhaler having air flow resistance values through its conduits in use of about 0.0065 to about 0.200$\sqrt{(\text{kPa})}$/L per minute, wherein the dry powder inhaler in use has an air flow distribution of from about 10% to about 30% through the container, which generates peak inhalation pressure differentials of about 2 kPa to about 20 kPa, and peak flow rates of between 7 L to about 70 L per minute.

DEFINITION OF TERMS

Figure 1:
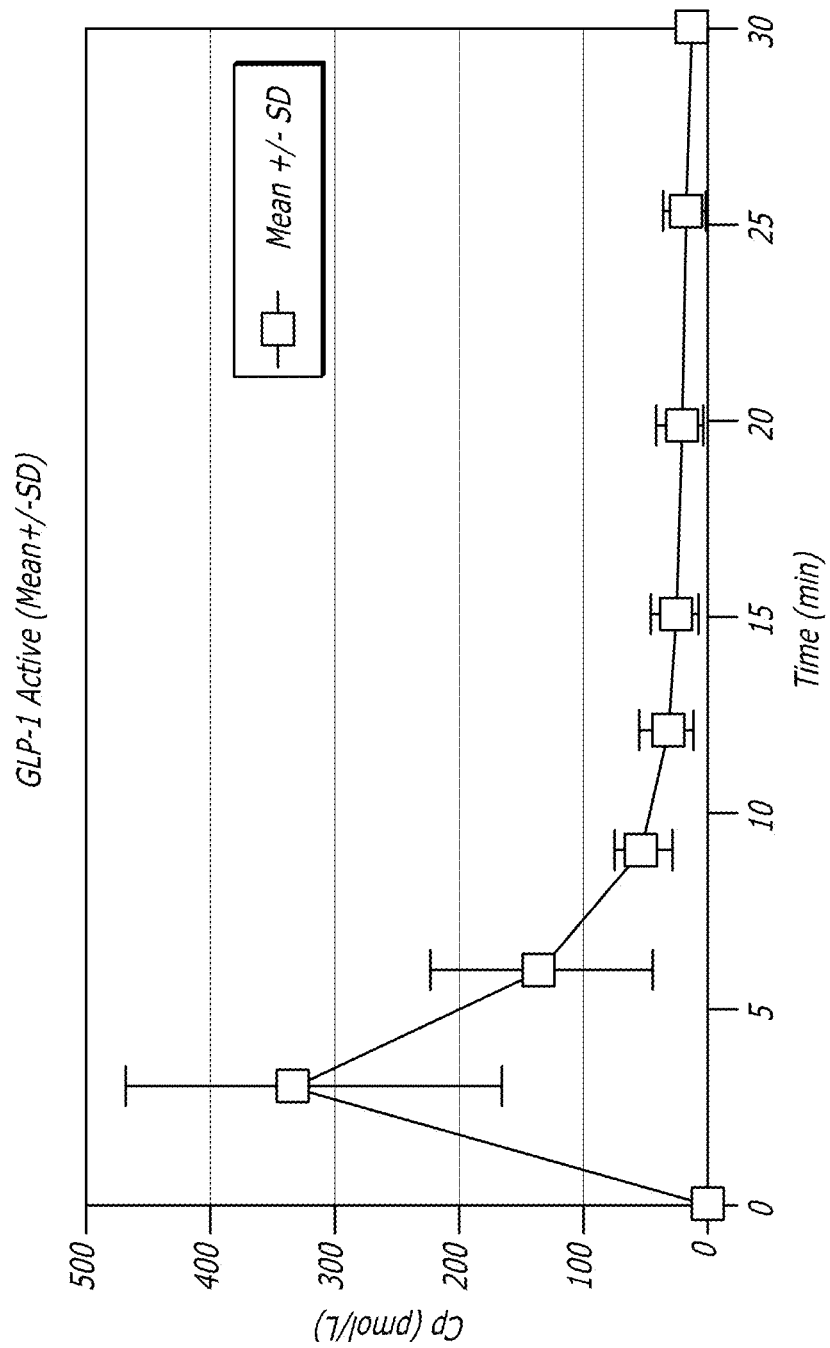
FIG. 1 depicts the mean plasma concentration of active glucagon-like peptide 1 (GLP-1) in subjects treated with an inhalable dry powder formulation containing a GLP-1 dose of 1.5 mg measured at various times after inhalation.

Prior to setting forth the invention, it may be helpful to provide an understanding of certain terms that will be used hereinafter:

Active Agents: As used herein "active agent" refers to drugs, pharmaceutical substances and bioactive agents. Active agents can be small molecules, which are typically less than about 1,000 in molecular weight, do not necessarily have repeated units. Active agents can also be organic macromolecules including nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 40 amino acid residues, but may include more. Proteins are polymers that typically contain more than 40 amino acid residues. The term polypeptide as is know in the art and as used herein, can refer to a peptide, a protein, or any other chain of amino acids of any length containing multiple peptide bonds, though generally containing at least 10 amino acids. The active agents can fall under a variety of biological activity classes, such as vasoactive agents, neuroactive agents, hormones, anticoagulants, immunomodulating agents, cytotoxic agents, antibiotics, antiviral agents, antigens, and antibodies. More particularly, active agents may include, in a non-limiting manner, insulin and analogs thereof, growth hormone, parathyroid hormone (PTH), ghrelin, granulocyte macrophage colony stimulating factor (GM-CSF), glucagon-like peptide 1 (GLP-1), and analogs of such peptides, alkynes, cyclosporins, clopidogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens. In some instances, the terms "drug" and "active agent" are used interchangeably.

Diketopiperazine: As used herein, "diketopiperazine" or "DKP" includes diketopiperazines, derivatives, analogs and modifications thereof, in both the salt and non-salt form of any of the foregoing, falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

Formula 1

Diketopiperazines, in addition to making aerodynamically suitable microparticles, can also facilitate the delivery of active agents by rapidly dissolving at physiologic pH thereby releasing the active agent and speeding its absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In one embodiment, the diketopiperazine is 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di (4-aminobutyl)-2,5-diketopiperazine, which can be formed by (thermal) condensation of the amino acid lysine. Exemplary derivatives include 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071, 497, and 6,331,318, each of which is incorporated herein by reference for all that it teaches regarding diketopiperazines and diketopiperazine-mediated drug delivery). The use of DKP salts is described in co-pending U.S. Pat. No. 7,820,676, which is hereby incorporated by reference for all it teaches regarding diketopiperazine salts. Pulmonary drug delivery using DKP microparticles is disclosed in U.S. Pat. No. 6,428, 771, which is hereby incorporated by reference in its entirety. Further details related to adsorption of active agents onto crystalline DKP particles can be found in co-pending U.S. Pat. Nos. 7,799,344 and 7,803,404, which are hereby incorporated by reference in their entirety.

Drug delivery system: As used herein, "drug delivery system" refers to a system for delivering one or more active agents.

Dry powder: As used herein, "dry powder" refers to a fine particulate composition that is not suspended or dissolved in a propellant, carrier, or other liquid. It is not meant to necessarily imply a complete absence of all water molecules.

Percent respirable fraction per fill (% RF/Fill): As used herein "% RF/Fill" refers to the amount of powder particles emitted from an inhaler, or drug delivery system, which particles are in the respirable range and can be smaller than 5.8 µm, normalized by the total amount of powder filled into inhaler or drug delivery system. In some embodiments, the inhaler comprises a cartridge for containing the dry powder.

Early phase: As used herein, "early phase" refers to the rapid rise in blood insulin concentration induced in response to a meal. This early rise in insulin in response to a meal is sometimes referred to as first-phase. In more recent sources first-phase is sometimes used to refer to the more rapid rise in blood insulin concentration of the kinetic profile achievable with a bolus IV injection of glucose in distinction to the meal-related response.

Endocrine disease: The endocrine system is an information signal system that releases hormones from the glands to provide specific chemical messengers which regulate many and varied functions of an organism, e.g., mood, growth and development, tissue function, and metabolism, as well as sending messages and acting on them. Diseases of the endocrine system include, but are not limited to diabetes mellitus, thyroid disease, and obesity. Endocrine disease is characterized by dysregulated hormone release (a productive pituitary adenoma), inappropriate response to signalling (hypothyroidism), lack or destruction of a gland (diabetes mellitus type 1, diminished erythropoiesis in chronic renal failure), reduced responsiveness to signaling (insulin resistance of diabetes mellitus type 2), or structural enlargement in a critical site such as the neck (toxic multinodular goiter). Hypofunction of endocrine glands can occur as result of loss of reserve, hyposecretion, agenesis, atrophy, or active destruction. Hyperfunction can occur as result of hypersecretion, loss of suppression, hyperplastic, or neoplastic change, or hyperstimulation. The term endocrine disorder encompasses metabolic disorders.

Excursion: As used herein, "excursion" can refer to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating. While excursion has been described here in terms of blood glucose, in other contexts the term may be similarly applied to other analytes.

Glucose elimination rate: As used herein, "glucose elimination rate" is the rate at which glucose disappears from the blood. It is commonly determined by the amount of glucose infusion required to maintain stable blood glucose, often around 120 mg/dL during the study period. This glucose elimination rate is equal to the glucose infusion rate, abbreviated as GIR.

Hyperglycemia: As used herein, "hyperglycemia" is a higher than normal fasting blood glucose concentration, usually 126 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL 3.5 mM). Clinically relevant hypoglycemia is defined as blood glucose concentration below 63 mg/dL or causing patient symptoms such as hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal or snack.

Microparticles: As used herein, the term "microparticles" includes particles of generally 0.5 to 100 microns in diameter and particularly those less than 10 microns in diameter. Various embodiments will entail more specific size ranges. The microparticles can be assemblages of crystalline plates with irregular surfaces and internal voids as is typical of those made by pH controlled precipitation of the DKP acids. In such embodiments the active agents can be entrapped by the precipitation process or coated onto the crystalline surfaces of the microparticle. The microparticles can also be spherical shells or collapsed spherical shells comprising DKP salts with the active agent dispersed throughout. Typically such particles can be obtained by spray drying a co-solution of the DKP and the active agent. The DKP salt in such particles can be amorphous. The forgoing descriptions should be understood as exemplary. Other forms of microparticles are contemplated and encompassed by the term.

Obesity: is a condition in which excess body fat has accumulated to such an extent that health may be negatively affected. Obesity is typically assessed by BMI (body mass index) with BMI of greater than 30 kg/m$^2$.

Peripheral tissue: As used herein, "peripheral tissue" refers to any connective or interstitial tissue that is associated with an organ or vessel.

Periprandial: As used herein, "periprandial" refers to a period of time starting shortly before and ending shortly after the ingestion of a meal or snack.

Postprandial: As used herein, "postprandial" refers to a period of time after ingestion of a meal or snack. As used herein, late postprandial refers to a period of time 3, 4, or more hours after ingestion of a meal or snack.

Potentiation: Generally, potentiation refers to a condition or action that increases the effectiveness or activity of some agent over the level that the agent would otherwise attain. Similarly it may refer directly to the increased effect or activity. As used herein, "potentiation" particularly refers to the ability of elevated blood insulin concentrations to boost effectiveness of subsequent insulin levels to, for example, raise the glucose elimination rate.

Prandial: As used herein, "prandial" refers to a meal or a snack.

Preprandial: As used herein, "preprandial" refers to a period of time before ingestion of a meal or snack.

Pulmonary inhalation: As used herein, "pulmonary inhalation" is used to refer to administration of pharmaceutical preparations by inhalation so that they reach the lungs and in particular embodiments the alveolar regions of the lung. Typically inhalation is through the mouth, but in alternative embodiments in can entail inhalation through the nose.

DETAILED DESCRIPTION

There is disclosed a method for the treatment of a disease or disorder which utilizes a drug delivery system that effectively delivers an active agent to the pulmonary circulation so that the active agent enters the pulmonary circulation and can be delivered in a therapeutic amount to the site(s) of action. The methods of treatment of disease or disorders comprise administering to a patient in need of treatment a formulation which can deliver the active agent directly into the pulmonary circulation, and thereby to the arterial circulation, and can avoid degradation of the active agent such as peptides, by enzymes or other mechanisms in the local peripheral and/or vasculature tissues of the lungs. In one embodiment, the method comprises the effective therapeutic delivery of active agents using a drug delivery system which allows for very rapid lung absorption of the active agent into the circulation and increases its effective bioavailability. In this embodiment, lower dosages of an active agent can be delivered by this method of administration. In similar embodiments effective doses can be achieved where they were not feasible by other modes of administration.

In embodiments herein, there is disclosed a method for the treatment of disease, including, endocrine disease, such as diabetes, hyperglycemia and obesity. The inventors have identified the need to deliver drugs directly to the systemic circulation, in particular, the arterial circulation in a noninvasive fashion so that the drug reaches the target organ(s) prior to returning through the venous system. This approach may paradoxically result in a higher peak target organ exposure to active agents than would result from a comparable administration via an intravenous, subcutaneous or other parenteral route. A similar advantage can be obtained versus oral administration as, even with formulations providing protection from degradation in the digestive tract, upon absorption the active agent also enters the venous circulation.

In one embodiment, the drug delivery system can be used with any type of active agent that is rapidly metabolized and/or degraded by direct contact with the local degradative enzymes or other degradative mechanisms, for example, oxidation, phosphorylation or any modification of the molecules including small molecules, proteins or peptides, in the peripheral or vascular venous tissue encountered with other routes of administration such as oral, intravenous, transdermal, and subcutaneous administration. In this embodiment, the method can comprise the step of identifying and selecting an active agent which activity is metabolized or degraded by oral, subcutaneous or intravenous administration. For example, due to lability, subcutaneous injection of GLP-1 has not led to effective levels of GLP-1 in the blood. This contrasts with peptides such as insulin which can be delivered effectively by such modes of administration. In these embodiments, the method of administering a drug is advantageous for, for example, rapid onset of treatment since the drug can reach the target organ more rapidly through the arterial circulation without invasive therapy such as injections.

In certain embodiments, the method of treatment of a disease or disorder comprises the step of selecting a suitable carrier for inhalation and delivering an active substance to pulmonary alveoli. In this embodiment, the carrier can be associated with one or more active agents to form a drug/carrier complex which can be administered as a composition that avoids rapid degradation of the active agent in the peripheral and vascular venous tissue of the lung. In one embodiment, the carrier is a diketopiperazine.

The method described herein can be utilized to deliver many types of active agents, including small molecules and biologicals. In particular embodiments, the method utilizes a drug delivery system that effectively delivers a therapeutic amount of an active agent, including, small molecules or peptide hormones, rapidly into the arterial circulation. In one embodiment, the one or more active agents include, but are not limited to peptides such as glucagon-like peptide 1 (GLP-1), proteins, lipokines, small molecule pharmaceuticals, nucleic acids and the like, which is/are sensitive to degradation or deactivation; formulating the active agent into a dry powder composition comprising a diketopiperazine and delivering the active agent(s) into the systemic circulation by pulmonary inhalation using a cartridge and a dry powder inhaler. In one embodiment, the method comprises selecting a peptide that is sensitive to enzymes in the local vascular or peripheral tissue of, for example, the dermis, or lungs. The present method allows the active agent to avoid or reduce contact with peripheral tissue, venous or liver metabolism/degradation. In another embodiment, for systemic delivery the active agent should not have specific receptors in the lungs.

In alternate embodiments, the drug delivery system can also be used to deliver therapeutic peptides or proteins of naturally occurring, recombinant, or synthetic origin for treating disorders or diseases, including, but not limited to adiponectin, cholecystokinin (CCK), secretin, gastrin, glucagon, motilin, somatostatin, brain natriuretic peptide (BNP), atrial natriuretic peptide (ANP), parathyroid hormone, parathyroid hormone related peptide (PTHrP), IGF-1, growth hormone releasing factor (GHRF), granulocyte-macrophage colony stimulating factor (GM-CSF), anti-IL-8 antibodies, IL-8 antagonists including ABX-IL-8; integrin beta-4 precursor (ITB4) receptor antagonist, enkephalins, nociceptin, nocistatin, orphanin FQ2, calcitonin, CGRP, angiotensin, substance P, neurokinin A, pancreatic polypeptide, neuropeptide Y, delta-sleep-inducing peptide, prostaglandins including PG-12, LTB receptor blockers including, LY29311, BIIL 284, CP105696; vasoactive intestinal peptide; triptans such as sumatriptan and lipokines such as C16:1n7 or palmitoleate or analogs thereof. In yet another embodiment, the active agent is a small molecule drug.

In one embodiment, the method of treatment is directed to the treatment of diabetes, hyperglycemia and/or obesity using, for example, formulations comprising glucagon-like peptide 1 (GLP-1), oxyntomodulin (OXN), or peptide YY (3-36) (PYY) either alone or in combination with one another, or in combination with one or more other active agents. In one embodiment, the method of treatment comprises administration of a formulation which does not contain GLP-1.

The incretin hormones GLP-1 and gastric inhibitory polypeptide (GIP) are produced by the endocrine cells of the intestine following ingestion of food. GLP-1 and GIP stimulate insulin secretion from the beta cells of the islets of Langerhans in the pancreas. Only GLP-1 causes insulin secretion in the diabetic state; however; the GLP-1 protein itself has been ineffective as a clinical treatment for diabetes when delivered by injection as it has a very short half-life in vivo. Exenatide (BYETTA®), a 39-amino-acid peptide, is an insulin secretagogue with glucoregulatory effects which bears a 50% amino acid homology to GLP-1 and has a longer half-life in vivo. Exenatide is a synthetic version of exendin-4, a hormone found in the saliva of the Gila monster.

In an exemplary embodiment, a method for treating obesity, diabetes and/or hyperglycemia comprises administering to a patient in need of treatment a dry powder composition or formulation comprising GLP-1, which stimulates the rapid secretion of endogenous insulin from pancreatic β-cells without causing unwanted side effects such as profuse sweating, nausea, and vomiting. In one embodiment, the method of treating disease can be applied to a patient, including a mammal, suffering with obesity, Type 2 diabetes mellitus and/or hyperglycemia at dosages ranging from about 0.02 to about 3 mg of GLP-1 in the formulation in a single dose. The method of treating hyperglycemia, diabetes, and/or obesity can be designed so that the patient can receive at least one dose of a GLP-1 formulation in proximity to a meal or snack. In this embodiment, the dose of GLP-1 can be selected depending on the patient's requirements. In one embodiment, pulmonary administration of GLP-1 can comprise a GLP-1 dose greater than 3 mg for example, in treating patients with type 2 diabetes.

In embodiments of the invention, the GLP-1 formulation is administered by inhalation such as by pulmonary administration. In this embodiment, pulmonary administration can be accomplished by providing the GLP-1 in a dry powder formulation for inhalation. The dry powder formulation is a stable composition and can comprise microparticles which are suitable for inhalation and which dissolve rapidly in the lung and rapidly deliver GLP-1 to the pulmonary circulation. Suitable particle sizes for pulmonary administration can be less than 10 μm in diameter, and preferably less than 5 μm. Exemplary particle sizes that can reach the pulmonary alveoli range from about 0.5 μm to about 5.8 μm in diameter. Such sizes refer particularly to aerodynamic diameter, but often also correspond to actual physical diameter as well. Such particles can reach the pulmonary capillaries and can avoid extensive contact with the peripheral tissue in the lung. In this embodiment, the drug can be delivered to the arterial circulation in a rapid manner and avoid degradation of the active ingredient by enzymes or other mechanisms prior to reaching its target or site of action in the body. In one embodiment, dry powder compositions for pulmonary inhalation comprising GLP-1 and FDKP can comprise microparticles wherein from about 35% to about 75% of the microparticles have an aerodynamic diameter of less than 5.8 μm.

The methods of delivery presented in various embodiments of the present invention can provide a more direct path to an active agent's site of action. Thus in addition to the avoidance of degradation, though in some instances still in part due to it, the biodistribution of the active agent can differ from that achieved with modes of delivery that entail absorption into and travel through the venous circulation prior to reaching sites of action in the body. Thus, sampling of venous blood to determine active agent concentration may underestimate the concentration of active agent at a site of action when using embodiments of the present disclosure while, in comparison, overestimating it when other modes of administration are used. The more labile an active agent is the greater this effect can be. For active agents such as GLP-1, with multiple effects and sites of action, a different constellation of effects may be observed as the relative concentrations at different sites of action will differ from that achieved using other modes of administration. This can further contribute to greater effective bioavailability, avoidance of unwanted effects and the like.

In one embodiment, the dry powder formulation for use with the methods comprises particles comprising a GLP-1 molecule and a diketopiperazine or a pharmaceutically acceptable salt thereof. In this and other embodiments, the dry powder composition of the present invention comprises one or more GLP-1 molecules selected from the group consisting of a native GLP-1, a GLP-1 metabolite, a long acting GLP-1, a GLP-1 derivative, a GLP-1 mimetic, an exendin, or an analog thereof. GLP-1 analogs include, but are not limited to GLP-1 fusion proteins, such as albumin linked to GLP-1.

In an exemplary embodiment, the method comprises the administration of the peptide hormone GLP-1 to a patient for the treatment of hyperglycemia and/or diabetes, and obesity. The method comprises administering to a patient in need of treatment an effective amount of an inhalable composition or formulation comprising a dry powder formulation comprising GLP-1 which stimulates the rapid secretion of endogenous insulin from pancreatic β-cells without causing unwanted side effects, including, profuse sweating, nausea, and vomiting. In one embodiment, the method of treating disease can be applied to a patient, including a mammal, suffering with Type 2 diabetes mellitus and/or hyperglycemia at dosages ranging from about 0.01 mg to about 3 mg, or from about 0.2 mg to about 2 mg of GLP-1 in the dry powder formulation. In one embodiment, the patient or subject to be treated is a human. The GLP-1 can be administered immediately before a meal (preprandially), at mealtime (prandially), and/or at about 15, 30 or 45 minutes after a meal (postprandially). In one embodiment, a single dose of GLP-1 can be administered immediately before a meal and another dose can be administered after a meal. In a particular embodiment, about 0.5 mg to about 1.5 mg of GLP-1 can be administered immediately before a meal, followed by 0.5 mg to about 1.5 mg about 30 minutes after a meal. In this embodiment, the GLP-1 can be formulated with inhalation particles such as a diketopiperazines with or without additional pharmaceutical carriers and excipients. In one embodiment, pulmonary administration of the GLP-1 formulation can provide plasma concentrations of GLP-1 greater than 100 pmol/L without inducing unwanted adverse side effects, such as profuse sweating, nausea and vomiting.

In another embodiment, a method for treating a patient including a human with type 2 diabetes and hyperglycemia is provided, the method comprises administering to the patient an inhalable GLP-1 formulation comprising GLP-1 in a dose of from about 0.5 mg to about 3 mg in FDKP microparticles wherein the levels of glucose in the blood of the patient are reduced to fasting plasma glucose concentrations of from 85 to 70 mg/dL within about 20 min after dosing without inducing nausea or vomiting in the patient. In one embodiment, pulmonary administration of GLP-1 at doses greater than 0.5 mg in a formulation comprising FDKP microparticles does not substantially inhibit gastric emptying.

In one embodiment, GLP-1 can be administered either alone as the active ingredient in the composition, or with a dipeptidyl peptidase (DPP-IV) inhibitor such as sitagliptin or vildagliptin, or with one or more other active agents. DPP-IV is a ubiquitously expressed serine protease that exhibits post-proline or alanine peptidase activity, thereby generating biologically inactive peptides by cleavage at the N-terminal region after X-proline or X-alanine, wherein X refers to any amino acid. Because both GLP-1 and GIP (glucose-dependent insulinotropic peptide) have an alanine residue at position 2, they are substrates for DPP-IV. DPP-IV inhibitors are orally administered drugs that improve glycemic control by preventing the rapid degradation of incretin hormones, thereby resulting in postprandial increases in levels of biologically active intact GLP-1 and GIP.

In this embodiment, the action of GLP-1 can be further prolonged or augmented in vivo if required, using DPP-IV inhibitors. The combination of GLP-1 and DPP-IV inhibitor therapy for the treatment of hyperglycemia and/or diabetes allows for reduction in the amount of active GLP-1 that may be needed to induce an appropriate insulin response from the β-cells in the patient. In another embodiment, the GLP-1 can be combined, for example, with other molecules other than a peptide, such as, for example, metformin. In one embodiment, the DPP-IV inhibitor or other molecules, including metformin, can be administered by inhalation in a dry powder formulation together with the GLP-1 in a co-formulation, or separately in its own dry powder formulation which can be administered concurrently with or prior to GLP-1 administration. In one embodiment, the DPP-IV inhibitor or other molecules, including metformin, can be administered by other routes of administration, including orally. In one embodiment, the DPP-IV inhibitor can be administered to the patient in doses ranging from about 1 mg to about 100 mg depending on the patient's need. Smaller concentrations of the DPP-IV inhibitor may be used when co-administered, or co-formulated with GLP-1. In this embodiment, the efficacy of GLP-1 therapy may be improved at reduced dosage ranges when compared to current dosage forms.

In embodiments described herein, GLP-1 can be administered at mealtime (in proximity in time to a meal or snack). In this embodiment, GLP-1 exposure can be limited to the postprandial period so it does not cause the long acting effects of current therapies. In embodiments wherein a DPP-IV inhibitor is co-administered, the DPP-IV inhibitor may be given to the patient prior to GLP-1 administration at mealtime. The amounts of DPP-IV inhibitor to be administered can range, for example, from about 0.10 mg to about 100 mg, depending on the route of administration selected. In further embodiments one or more doses of the GLP-1 can be administered after the beginning of the meal instead of or in addition to a dose administered in proximity to the beginning of a meal or snack. For example one or more doses can be administered 15 to 120 minutes after the beginning of a meal, such as at 30, 45, 60, or 90 minutes.

In one embodiment, the drug delivery system can be utilized in a method for treating obesity so as to control or reduce food consumption in an animal such as a mammal. In this embodiment, patients in need of treatment or suffering with obesity are administered a therapeutically effective amount of an inhalable composition or formulation comprising GLP-1, an exendin, oxyntomodulin, peptide YY(3-36), or combinations thereof, or analogs thereof, with or without additional appetite suppressants known in the art. In this embodiment, the method is targeted to reduce food consumption, inhibit food intake in the patient, decrease or suppress appetite, and/or control body weight. In another embodiment, the composition does not include GLP-1.

In one embodiment, the inhalable formulation comprises a dry powder formulation comprising the above-mentioned active ingredient with a diketopiperazine, including 2,5-diketo-3,6-di(4-X-aminobutyl)piperazine; wherein X is selected from the group consisting of succinyl, glutaryl, maleyl, and fumaryl, or a salt of the diketopiperazine. In this embodiment, the inhalable formulation can comprise microparticles for inhalation comprising the active ingredient with the aerodynamic characteristics as described above. In one embodiment, the amount of active ingredient can be determined by one of ordinary skill in the art, however, the present microparticles can be loaded with various amounts of active ingredient as needed by the patient. For example, for oxyntomodulin, the microparticles can comprise from about 1% (w/w) to about 75% (w/w) of the active ingredient in the formulation. In certain embodiments, the inhalable formulations can comprise from about 10% (w/w) to about 30% (w/w) of the pharmaceutical composition and can also comprise a pharmaceutically acceptable carrier, or excipient, such as a surfactant, such as polysorbate 80. In this embodiment, oxyntomodulin can be administered to the patient from once to about four times a day or as needed by the patient with doses ranging from about 0.05 mg up to about 5 mg in the formulation. In particular embodiments, the dosage to be administered to a subject can range from about 0.1 mg to about 3.0 mg of oxyntomodulin. In one embodiment, the inhalable formulation can comprise from about 50 pmol to about 700 pmol of oxyntomodulin in the formulation.

In embodiments disclosed herein wherein PYY is used as the active ingredient, a dry powder formulation for pulmonary delivery can be made comprising from about 0.10 mg to about 3.0 mg of PYY per dose. In certain embodiments, the formulation can comprise a dry powder comprising PYY in an amount ranging from about 1% to about 75% (w/w) of the peptide in the formulation. In particular embodiments, the amount of PYY in the formulation can be 5%, 10%, 15%, or 20% (w/w) and further comprising a diketopiperazine. In one embodiment, the PYY is administered in a formulation comprising a diketopiperazine, such as FDKP or a salt thereof, including sodium salts. In certain embodiments, PYY can be administered to a subject in dosage forms so that plasma concentrations of PYY after administration are from about 4 pmol/L to about 100 pmol/L or from about 10 pmol/L to about 50 pmol/L. In another embodiment, the amount of PYY can be administered, for example, in amounts ranging from about 0.01 mg to about 30 mg, or from about 5 mg to about 25 mg in the formulation. Other amounts of PYY can be determined as described, for example, in Savage et al. Gut 1987 February; 28(2):166-70; which disclosure is incorporated by reference herein. The PYY and/or analog, or oxyntomodulin and/or analog formulation can be administered preprandially, prandially, periprandially, or postprandially to a subject, or as needed and depending on the patient physiological condition.

In one embodiment, the formulation comprising the active ingredient can be administered to the patient in a dry powder formulation by inhalation using a dry powder inhaler such as the inhaler disclosed, for example, in U.S. Pat. No. 7,305,986 and U.S. patent application Ser. No. 10/655,153 (US 2004/0182387), which disclosures are incorporated herein by reference. Repeat inhalation of dry powder formulation comprising the active ingredient can also be administered between meals and daily as needed. In some embodiments, the formulation can be administered once, twice, three or four times a day.

In still yet a further embodiment, the method of treating hyperglycemia and/or diabetes comprises the administration of an inhalable dry powder composition comprising a diketopiperazine having the formula 2,5-diketo-3,6-di(4-X-aminobutyl)piperazine, wherein X is selected from the group consisting of succinyl, glutaryl, maleyl, and fumaryl. In this embodiment, the dry powder composition can comprise a diketopiperazine salt. In still yet another embodiment of the present invention, there is provided a dry powder composition, wherein the diketopiperazine is 2,5-diketo-3,6-di-(4-fumaryl-aminobutyl)piperazine, with or without a pharmaceutically acceptable carrier, or excipient.

In certain embodiments, the method of treatment can comprise a dry powder formulation for inhalation comprising GLP-1, wherein the GLP-1 molecule is native GLP-1, or an amidated GLP-1 molecule, wherein the amidated GLP-1 molecule is GLP-1(7-36) amide, or combinations thereof. In one embodiment, the GLP-1 can be an analog such as exenatide.

In another embodiment, GLP-1 can be administered with insulin as a combination therapy and given prandially for the treatment of hyperglycemia and/or diabetes, for example, Type 2 diabetes mellitus. In this embodiment, GLP-1 and insulin can be co-formulated in a dry powder formulation or administered separately to a patient in their own formulation. In one embodiment, wherein the GLP-1 and insulin are co-administered, both active ingredients can be co-formulated, for example, the GLP-1 and insulin can be prepared in a dry powder formulation for inhalation using a diketopiperazine particle as described above. Alternatively, the GLP-1 and insulin can be formulated separately, wherein each formulation is for inhalation and comprise a diketopiperazine particle. In one embodiment the GLP-1 and the insulin formulations can be admixed together in their individual powder form to the appropriate dosing prior to administration. In this embodiment, the insulin can be short-, intermediate-, or long-acting insulin and can be administered prandially.

In one embodiment for the treatment of Type 2 diabetes using co-administration of GLP-1 and insulin, an inhalable formulation of GLP-1 can be administered to a patient prandially, simultaneously, or sequentially to an inhalable formulation of insulin such as insulin/FDKP. In this embodiment, in a Type 2 diabetic, GLP-1 can stimulate insulin secretion from the patient's pancreas, which can delay disease progression by preserving β-cell function (such as by promoting β-cell growth) while prandially-administered insulin can be used as insulin replacement which mimics the body's normal response to a meal. In certain embodiments of the combination therapy, the insulin formulation can be administered by other routes of administration. In this embodiment, the combination therapy can be effective in reducing insulin requirements in a patient to maintain the euglycemic state. In one embodiment, the combination therapy can be applied to patients suffering with obesity and/or Type 2 diabetes who have had diabetes for less than 10 years and are not well controlled on diet and exercise or secretagogues. In one embodiment, the patient population for receiving GLP-1 and insulin combination therapy can be characterized by having β-cell function greater than about 25% of that of a normal healthy individual and/or, insulin resistance of less than about 8% and/or can have normal gastric emptying. In one embodiment, the inhalable GLP-1 and insulin combination therapy can comprise a rapid acting insulin such as insulin glulisine (APIDRA®), insulin lispro (HUMALOG®) or insulin aspart (NOVOLOG®), or a long acting insulin such as insulin detemir (LEVEMIR®) or insulin glargine (LANTUS®), which can be administered by an inhalation powder also comprising FDKP or by other routes of administration.

In another embodiment, a combination therapy for treating Type 2 diabetes can comprise administering to a patient in need of treatment an effective amount of an inhalable insulin formulation comprising an insulin and a diketopiperazine, wherein the insulin can be a native insulin peptide, a recombinant insulin peptide, and further administering to the patient a long acting insulin analog which can be provided by inhalation in a formulation comprising a diketopiperazine or by another route of administration such as by subcutaneous injection. The method can further comprise the step of administering to the patient an effective amount of a DPP IV inhibitor. In one embodiment, the method can comprise administering to a patient in need of treatment, a formulation comprising a rapid acting or long acting insulin molecule and a diketopiperazine in combination with formulation comprising a long acting GLP-1, which can be administered separately and/or sequentially. GLP-1 therapy for treating diabetes, in particular Type 2 diabetes, can be advantageous since administration of GLP-1 alone in a dry powder inhalable formulation or in combination with insulin or non-insulin therapies can reduce the risk of hypoglycemia.

In another embodiment, rapid acting GLP-1 and a diketopiperazine formulation can be administered in combination with a long acting GLP-1, such as exendin, for the treatment of diabetes, which can be both administered by pulmonary inhalation. In this embodiment, a diabetic patient suffering, for example, with Type 2 diabetes, can be administered prandially an effective amount of an inhalable formulation comprising GLP-1 so as to stimulate insulin secretion, while sequentially or sometime after such as from mealtime up to about 45 min, thereafter administering a dose of exendin-4. Administration of inhalable GLP-1 can prevent disease progression by preserving n-cell function while exendin-4 can be administered twice daily at approximately 10 hours apart, which can provide basal levels of GLP-1 that can mimic the normal physiology of the incretin system in a patient. Both rapid acting GLP-1 and a long acting GLP-1 can be administered in separate, inhalable formulations. Alternatively, the long acting GLP-1 can be administered by other methods of administration including, for example, transdermally, intravenously or subcutaneously. In one embodiment, prandial administration of a short-acting and long acting GLP-1 combination may result in increased insulin secretion, greater glucagon suppression and a longer delay in gastric emptying compared to long acting GLP-1 administered alone. The amount of long acting GLP-1 administered can vary depending on the route of administration. For example, for pulmonary delivery, the long acting GLP-1 can be administered in doses from about 0.1 mg to about 1 mg per administration, immediately before a meal or at mealtime, depending on the form of GLP-1 administered to the patient.

In one embodiment, the present method can be applied to the treatment of obesity. A therapeutically effective amount of an inhalable GLP-1 formulation can be administered to a patient in need of treatment, wherein an inhalable dry powder, GLP-1 formulation comprises GLP-1 and a diketopiperazine as described above. In this embodiment, the inhalable GLP-1 formulation can be administered alone or in combination with one or more endocrine hormone and/or anti-obesity active agents for the treatment of obesity. Exemplary endocrine hormones and/or anti-obesity active agents include, but are not limited to, peptide YY, oxyntomodulin, amylin, amylin analogs such as pramlintide acetate, and the like. In one embodiment, the anti-obesity agents can be administered in a co-formulation in a dry powder inhalable composition alone or in combination with GLP-1 together or in a separate inhalable dry powder composition for inhalation. Alternatively, in the combination of GLP-1 with one or more anti-obesity agents, or agents that can cause satiety, the GLP-1 formulation can be administered in a dry powder formulation and the anti-obesity agent can be administered by alternate routes of administration. In this embodiment, a DPP-IV inhibitor can be administered to enhance or stabilize GLP-1 delivery into the pulmonary arterial circulation. In another embodiment, the DPP-IV inhibitor can be provided in combination with an insulin formulation comprising a diketopiperazine. In this embodiment, the DPP-IV inhibitor can be formulated in a diketopiperazine for inhalation or it can be administered in other formulation for other routes of administration such as by subcutaneous injection or oral administration.

In an embodiment, a kit for treating diabetes and/or hyperglycemia is provided which comprises a medicament cartridge for inhalation comprising a GLP-1 formulation and an inhalation device which is configured to adapt or securely engage the cartridge. In this embodiment, the kit can further comprise a DPP-IV inhibitor co-formulated with GLP-1, or in a separate formulation for inhalation or oral administration as described above. In variations of this embodiment, the kit does not include the inhalation device which can be provided separately.

In one embodiment, the present combination therapy using the drug delivery system can be applied to treat metabolic disorders or syndromes. In this embodiment, the drug delivery formulation can comprise a formulation comprising a diketopiperazine and an active agent, including GLP-1 and/or a long acting GLP-1 alone or in combination with one or more active agents such as a DPP-IV inhibitor and exendin, targeted to treat the metabolic syndrome. In this embodiment, at least one of the active agents to be provided to the subject in need of treatment and who may exhibit insulin resistance can be administered by pulmonary inhalation.

In another embodiment, the pulmonary administration of an inhalable dry powder formulation comprising GLP-1 and a diketopiperazine can be used as a diagnostic tool to diagnose the level or degree of progression of type 2 diabetes in a patient afflicted with diabetes in order to identify the particular treatment regime suitable for the patient to be treated. In this embodiment, a method for diagnosing the level of diabetes progression in a patient identified as having diabetes, the method comprising administering to the patient a predetermined amount of an inhalable dry powder formulation comprising GLP-1 and a diketopiperazine and measuring the endogenous insulin production or response. The administration of the inhalable dry powder formulation comprising GLP-1 can be repeated with predetermined amounts of GLP-1 until the appropriate levels of an insulin response is obtained for that patient to determine the required treatment regime required by the patient. In this embodiment, if a patient insulin response is inadequate, the patient may require alternative therapies. Patients who are sensitive or insulin-responsive can be treated with a GLP-1 formulation comprising a diketopiperazine as a therapy. In this manner, the specific amount of GLP-1 can be administered to a patient in order to achieve an appropriate insulin response to avoid hypoglycemia. In this and other embodiments, GLP-1 can induce a rapid release of endogenous insulin which mimics the normal physiology of insulin release.

In one embodiment, the present drug delivery system can be applied to treat metabolic disorders or syndromes. In this embodiment, the drug delivery formulation can comprise a formulation comprising a diketopiperazine and an active agent, including GLP-1 and/or a long acting GLP-1 alone or in combination with one or more active agents such as a DPP-IV inhibitor and exendin, targeted to treat the metabolic syndrome. In this embodiment, at least one of the active agents to be provided to the subject in need of treatment and who may exhibit insulin resistance can be administered by pulmonary inhalation. In another embodiment, the drug formulation does not include GLP-1.

In another exemplary embodiment, a method for treating migraines using a therapeutically effective pharmaceutical composition comprising a powder for pulmonary delivery is disclosed, wherein the powder comprises microparticles of a diketopiperazine and an active agent for treating migraines. In this embodiment, the pharmaceutical composition comprises, for example, a diketopiperazine, including, FDKP or an FDKP salt, for example, a divalent salt of FDKP, including disodium FDKP, and a small molecule, including a vasoconstrictor as the active agent Examples of vasoconstrictors are serotonin receptor agonists including, tripans such as sumatriptan, almotriptan, eletriptan, frovatriptan, naratriptan, rizatriptan, zolmitriptan and pharmaceutically acceptable salts thereof, including sumatriptan succinate, rizatriptan benzoate, almotriptan malate. In one embodiment, the vasoconstrictor, for example, a triptan can be provided to a patient in need of treatment in amounts ranging from at least about 0.1 mg, at least about 1 mg, at least about 5 mg, about 50 mg or less, about 40 mg or less, about 1 mg to about 50 mg, about 5 mg to about 30 mg, about 10 mg. to about 20 mg, about 1 mg, about 10 mg, about 20 mg, or any amount in a range bounded by, or between, any of these values. A pharmaceutical composition comprising a triptan may be given regularly, including daily, twice daily, thrice daily, etc., and/or may be given as need at the onset of migraine symptoms. In one embodiment, the triptan can be administered to the patient by inhalation. In a particular embodiment, the triptan is provided to a patient by oral inhalation for delivery to the arterial circulation in the lungs.

In an exemplary embodiment of the invention, the drug delivery formulation can comprise an aliphatic amino acid, for example, alanine, glycine, leucine, isoleucine, norleucine, and serine. In certain embodiments, the aliphatic amino acid is from about 0.5% to about 30% by weight of the composition. In a particular embodiment, the pharmaceutical composition comprises L-leucine. In one embodiment, the pharmaceutical composition comprises a dry powder for oral inhalation comprising FDKP disodium salt, sumatriptan and L-leucine.

EXAMPLES

The following examples are included to demonstrate certain embodiments of the invention. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention.

Example 1

Administration of GLP-1 in an Inhalable Dry Powder to Healthy Adult Males

GLP-1 has been shown to control elevated blood glucose in humans when given by intravenous (iv) or subcutaneous (sc) infusions or by multiple subcutaneous injections. Due to the extremely short half-life of the hormone, continuous subcutaneous infusion or multiple daily subcutaneous injections would be required to achieve clinical efficacy. Neither of these routes is practical for prolonged clinical use. Applicants have found in animal experiments that when GLP-1 was administered by inhalation, therapeutic levels could be achieved. The results of these studies can be found, for example, in U.S. patent application Ser. No. 11/735,957, the disclosure of which is incorporated by reference herein.

In healthy individuals, several of the actions of GLP-1, including reduction in gastric emptying, increased satiety, and suppression of inappropriate glucagon secretion appear to be linked to the burst of GLP-1 released as meals begin. By supplementing this early surge in GLP-1 with a formulation of GLP-1 and 2,5-diketo-3,6-di(4-fumaryl-aminobutyl)piperazine (FDKP) as an inhalation powder, a pharmacodynamic response, including endogenous insulin production, reduction in glucagon and glucose levels, in diabetic animals can be elicited. In addition, the late surge in native GLP-1 linked to increased insulin secretion can be mimicked by postprandial administration of GLP-1/FDKP inhalation powder.

A Phase 1a clinical trial of GLP-1/FDKP inhalation powder was designed to test the safety and tolerability of selected doses of a new inhaled glycemic control therapeutic product for the first time in human subjects. GLP-1/FDKP inhalation powder was administered using the MedTone® Inhaler device, previously tested. The experiments were designed to identify the safety and tolerability of various doses of GLP-1/FDKP inhalation powder by pulmonary inhalation. Doses were selected for human use based on animal safety study results from non-clinical studies in rats and primates using GLP-1/FDKP administered by inhalation as described in U.S. application Ser. No. 11/735,957, which is incorporated herein by reference.

Twenty-six subjects were enrolled into 5 cohorts to provide up to 4 evaluable subjects in each of cohorts 1 and 2 and up to 6 evaluable subjects in each of cohorts 3 to 5 who met eligibility criteria and completed the study. Each subject was dosed once with GLP-1 as GLP-1/FDKP inhalation powder at the following dose levels: cohort 1: 0.05 mg; cohort 2: 0.45 mg; cohort 3: 0.75 mg; cohort 4: 1.05 mg and cohort 5: 1.5 mg of GLP-1. Dropouts were not replaced. These dosages assumed a body mass of 70 kg. Persons of ordinary skill in the art can determine additional dosage levels based on the studies disclosed herein.

In these experiments, the safety and tolerability of ascending doses of GLP-1/FDKP inhalation powder in healthy adult male subjects were determined. The tolerability of ascending doses of GLP-1/FDKP inhalation powder were determined by monitoring pharmacological or adverse effects on variables including reported adverse events (AE), vital signs, physical examinations, clinical laboratory tests and electrocardiograms (ECG).

Additional pulmonary safety and pharmacokinetic parameters were also evaluated. Pulmonary safety as expressed by the incidence of pulmonary and other adverse events and changes in pulmonary function between Visit 1 (Screening) and Visit 3 (Follow-up) was studied. Pharmacokinetic (PK) parameters of plasma GLP-1 and serum fumaryl diketopiperazine (FDKP) following dosing with GLP-1/FDKP inhalation powder were measured as $AUC_{0-120\ min}$ plasma GLP-1 and $AUC_{0-480\ min}$ serum FDKP. Additional PK parameters of plasma GLP-1 included the time to reach maximal plasma GLP-1 concentration, $T_{max}$ plasma GLP-1; the maximal concentration of GLP-1 in plasma, $C_{max}$ plasma GLP-1, and the half of total time to reach maximal concentration of GLP-1 in plasma, $T_{1/2}$ plasma GLP-1. Additional PK parameters of serum FDKP included $T_{max}$ serum FDKP, $C_{max}$ serum FDKP, and $T_{1/2}$ serum FDKP. Clinical trial endpoints were based on a comparison of the following pharmacological and safety parameters determined in the trial subject population. Primary endpoints included the incidence and severity of reported AEs, including cough and dyspnea, nausea and/or vomiting, as well as changes from screening in vital signs, clinical laboratory tests and physical examinations. Secondary endpoints included pharmacokinetic disposition of plasma GLP-1 and serum FDKP ($AUC_{0-120\ min}$ plasma GLP-1 and $AUC_{0-480\ min}$ serum FDKP), plasma GLP-1 ($T_{max}$ plasma GLP-1, $C_{max}$ plasma GLP-1 $T_{1/2}$ plasma GLP-1); serum FDKP ($T_{max}$ serum FDKP, $C_{max}$ serum FDKP); pulmonary function tests (PFTs), and ECG.

The clinical trial consisted of 3 clinic visits: 1) One screening visit (Visit 1); 2) One treatment visit (Visit 2); and 3) One follow-up visit (Visit 3) 8-14 days after Visit 2. A single dose of GLP-1/FDKP inhalation powder was administered at Visit 2.

Five doses of GLP-1/FDKP inhalation powder (0.05, 0.45, 0.75, 1.05 and 1.5 mg of GLP-1) were assessed. To accommodate all doses, formulated GLP-1/FDKP was mixed with FDKP inhalation powder containing particles without active agent. Single-dose cartridges containing 10 mg dry powder consisting of GLP-1/FDKP inhalation powder (15% weight to weight GLP-1/FDKP) as is or mixed with the appropriate amount of FDKP inhalation powder was used to obtain the desired dose of GLP-1 (0.05 mg, 0.45 mg, 0.75 mg, 1.05 mg and 1.5 mg). The first 2 lowest dose levels were evaluated in 2 cohorts of 4 subjects each and the 3 higher dose levels were evaluated in 3 cohorts of 6 subjects each. Each subject received only 1 dose at 1 of the 5 dose levels assessed. In addition to blood drawn for GLP-1 (active and total) and FDKP measurements, samples were drawn for glucagon, glucose, insulin, and C-peptide determination. The results from these experiments are described with reference to the following figures and tables.

FIG. 1 depicts the active GLP-1 plasma concentration in cohort 5 after pulmonary administration of 1.5 mg of GLP-1 dose. The data showed that the peak GLP-1 concentration occurred prior to the first sampling point at 3 minutes, closely resembling intravenous (IV) bolus administration. GLP-1 plasma concentrations in some subjects were greater than 500 pmol/L, the assay limit. Peak active GLP-1 plasma concentrations range from about 150 pmol/L to about 500 pmol/L. Intravenous bolus administration of GLP-1 as reported in the literature (Vilsboll et al. 2000) results in ratios of total:active GLP-1 of 3.0-5.0 compared to a ratio of 1.5 in cohort 5 of this study. At comparable active concentrations the metabolite peaks were 8-9 fold greater following intravenous administration compared to pulmonary administration, suggesting that pulmonary delivery results in rapid delivery and less degradation of GLP-1.

TABLE 1

| Parameter[a] | Treatment | | | | |
|---|---|---|---|---|---|
| | 0.05 mg (n = 4) | 0.45 mg (n = 4) | 0.75 mg (n = 6) | 1.05 mg (n = 6) | 1.5 mg (n = 6) |
| | GLP-1[a] | | | | |
| $AUC_{0-120}$ (min*pmol/L) | ND | n = 1<br>355.33 | n = 6<br>880.12<br>(195.656) | n = 4<br>1377.88<br>(634.054) | n = 4<br>AULQ |
| $C_{max}$ (pmol/L) | n = 4<br>2.828<br>(2.4507) | n = 4<br>24.630<br>(8.7291) | n = 6<br>81.172<br>(63.3601) | n = 6<br>147.613<br>(122.7014) | n = 6<br>310.700<br>(54.2431) |
| $t_{max}$ (min) | n = 4<br>3.00<br>(3.00, 3.00) | n = 4<br>3.00<br>(3.00, 4.02) | n = 6<br>3.00<br>(3.00, 6.00) | n = 6<br>3.00<br>(3.00, 4.98) | n = 6<br>3.00<br>(3.00, 3.00) |
| $T_{1/2}$ (min) | n = 1<br>6.1507 | n = 3<br>3.0018<br>(0.83511) | n = 6<br>5.5000<br>(2.96928) | n = 4<br>3.6489<br>(1.88281) | n = 6<br>3.9410<br>(1.79028) |

TABLE 1-continued

| Parameter[a] | Treatment | | | | |
|---|---|---|---|---|---|
| | 0.05 mg (n = 4) | 0.45 mg (n = 4) | 0.75 mg (n = 6) | 1.05 mg (n = 6) | 1.5 mg (n = 6) |
| | | | FDKP | | |
| $AUC_{0-120}$ (min*pmol/L) | | | | n = 6 22169.2 (4766.858) | n = 6 25594.7 (5923.689) |
| $C_{max}$ (pmol/L) | | | | n = 6 184.21 (56.893) | n = 6 210.36 (53.832) |
| $t_{max}$ (min) | | | | n = 6 4.50 (3.00, 25.02) | n = 6 6.00 (3.00, 19.98) |
| $T_{1/2}$ (min) | | | | n = 6 126.71 (11.578) | n = 6 123.82 (15.640) |

[a]All parameters are mean (SD) except tmax, which is median (range)
AULQ—Two or more subjects in the dose group had plasma concentrations of the analyte that were AULQ;
NA = The pharmacokinetic profile did not meet the specifications for this profile because of the short sampling time (20 minutes);
ND = Parameter could not be calculated because of insufficient data is some subjects.

In healthy individuals, physiological post-prandial venous plasma concentrations of GLP-1 typically range from 10-20 pmol/L (Vilsboll et al. *J. Clin. Endocr. & Metabolism.* 88(6): 2706-13, June 2003). These levels were achieved with some subjects in cohort 2, who received 0.45 mg GLP-1. Higher doses of GLP-1 produced peak plasma GLP-1 concentrations substantially higher than physiological peak venous concentrations. However, because the half-life of GLP-1 is short (about 1-2 min), plasma concentrations of active GLP-1 fell to the physiological range by 9 min after administration. Although the peak concentrations are much higher than those seen physiologically in the venous circulation, there is evidence that local concentrations of GLP-1 may be much higher than those seen systemically.

Table 1 shows the pharmacokinetic profile of GLP-1 in a formulation comprising FDKP from this study.

FDKP pharmacokinetic parameters are also represented in Table 1 for cohorts 4 and 5. Other cohorts were not analyzed. The data also shows that mean plasma concentration of FDKP for the 1.05 mg and the 1.5 mg GLP-1 treated subjects were about 184 and 211 pmol/L, respectively. Maximal plasma FDKP concentrations were attained at about 4.5 and 6 min after administration for the respective dose with a half-life about 2 hr (127 and 123 min).

Figure 2A:
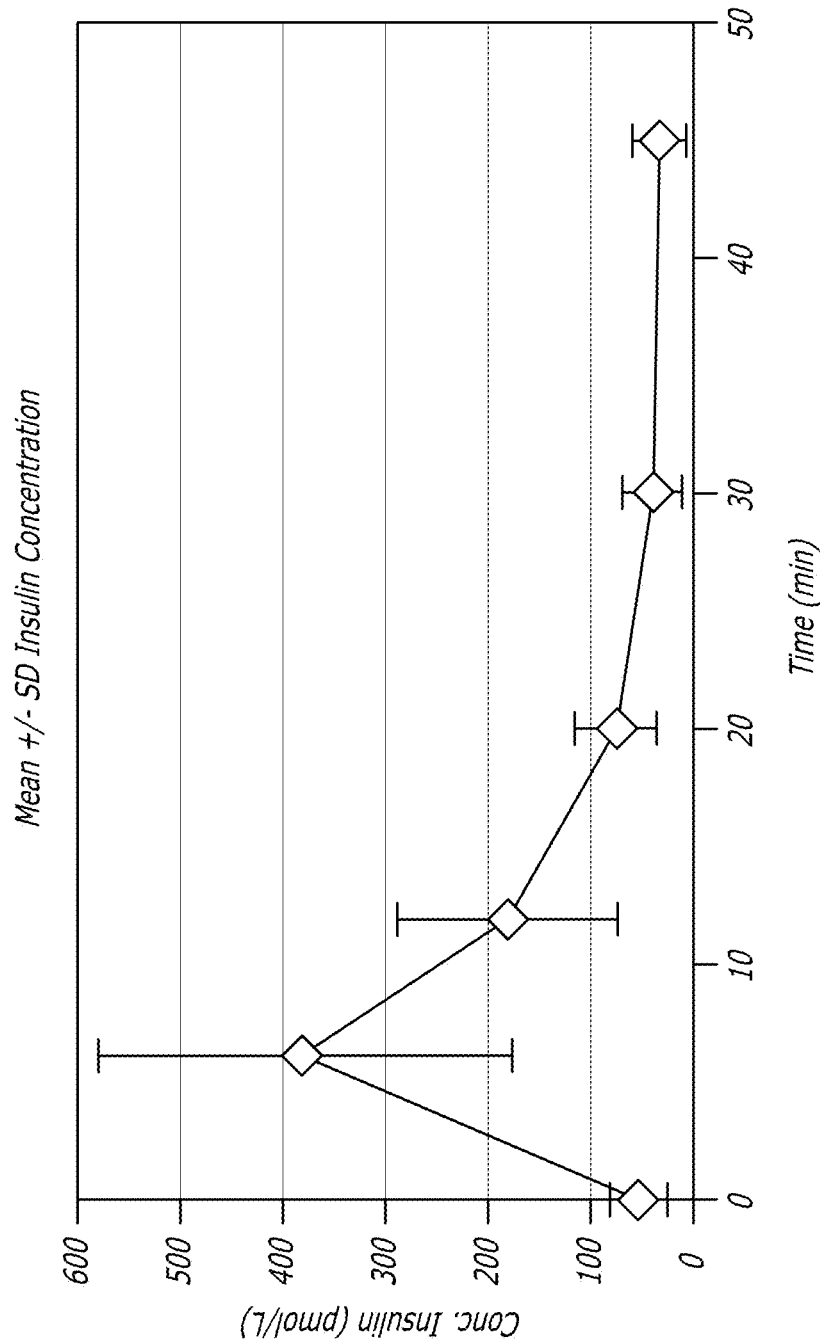
FIG. 2A depicts the mean plasma concentration of insulin in subjects treated with an inhalable dry powder formulation containing a GLP-1 dose of 1.5 mg measured at various times after inhalation.
Figure 2B:
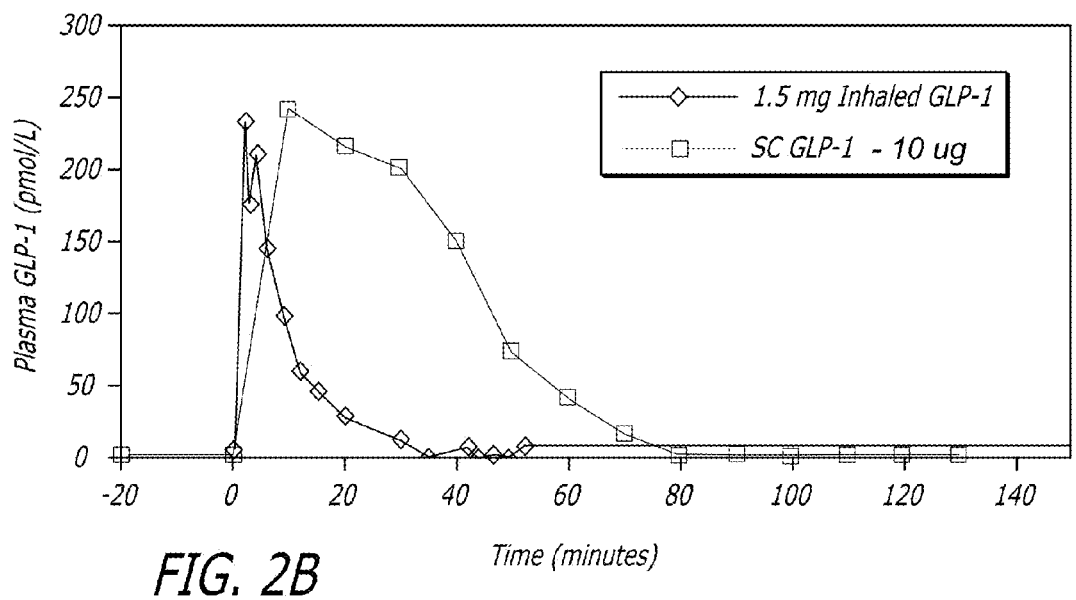
FIG. 2B depicts the plasma concentration of GLP-1 in subjects treated with an inhalable dry powder formulation containing a GLP-1 dose of 1.5 mg measured at various times after inhalation compared to subjects treated with a subcutaneous administration of GLP-1.
Figure 2C:
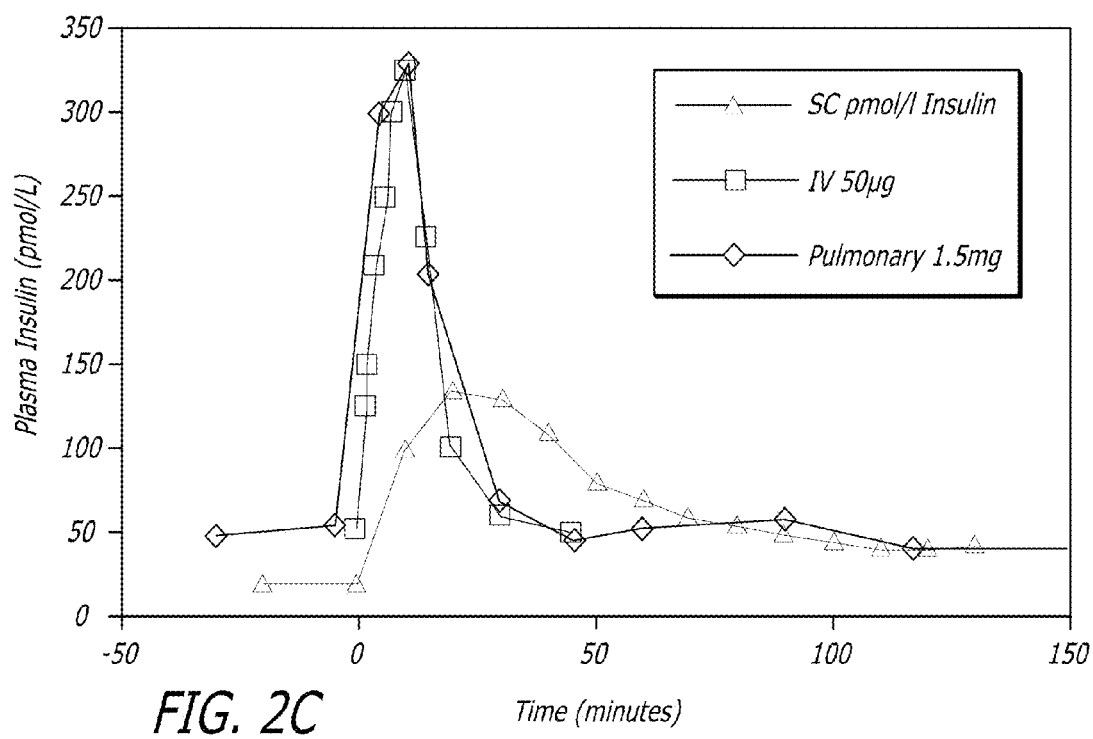
FIG. 2C depicts the plasma insulin concentration in subjects treated with an inhalable dry powder formulation containing a GLP-1 dose of 1.5 mg measured at various times after inhalation compared to subjects treated with an intravenous GLP-1 dose of 50 µg and subjects treated with a subcutaneous GLP-1 dose.

FIG. 2A depicts mean insulin concentrations in subjects treated with an inhalable dry powder formulation of GLP-1 at a dose of 1.5 mg. The data show the 1.5 mg GLP-1 dose induced endogenous insulin release from β-cells since insulin concentrations were detected in all subjects, and the mean peak insulin concentrations of about 380 pmol/L occurred at 6 min after dosing or earlier. The insulin release was rapid, but not sustained, since plasma insulin concentration fell rapidly after the initial response to GLP-1. FIG. 2B depicts the GLP-1 plasma concentration of subjects treated with the 1.5 mg dose of GLP administered by pulmonary inhalation compared to subcutaneous administration of a GLP-1 dose. The data illustrate that pulmonary administration of GLP-1 occurs relatively fast and peak plasma concentration of GLP-1 occur faster than with subcutaneous administration. Additionally, pulmonary inhalation of GLP-1 leads to GLP-1 plasma concentrations returning to basal levels much faster than with subcutaneous administration. Thus the exposure of the patient to GLP-1 provided by pulmonary inhalation using the present drug delivery system is shorter in time than by subcutaneous administration and the total exposure to GLP-1 as measured by AUC is less for the inhaled GLP-1. FIG. 2C illustrates that pulmonary administration of a dry powder formulation of GLP-1 induces an insulin response which is similar to the response obtained after intravenous administration of GLP-1, but different in peak time and amount of endogenous insulin produced than with subcutaneous GLP-1 administration, which indicates that pulmonary administration of GLP-1 using the present formulation is more efficacious at inducing an insulin response.

Figure 3:
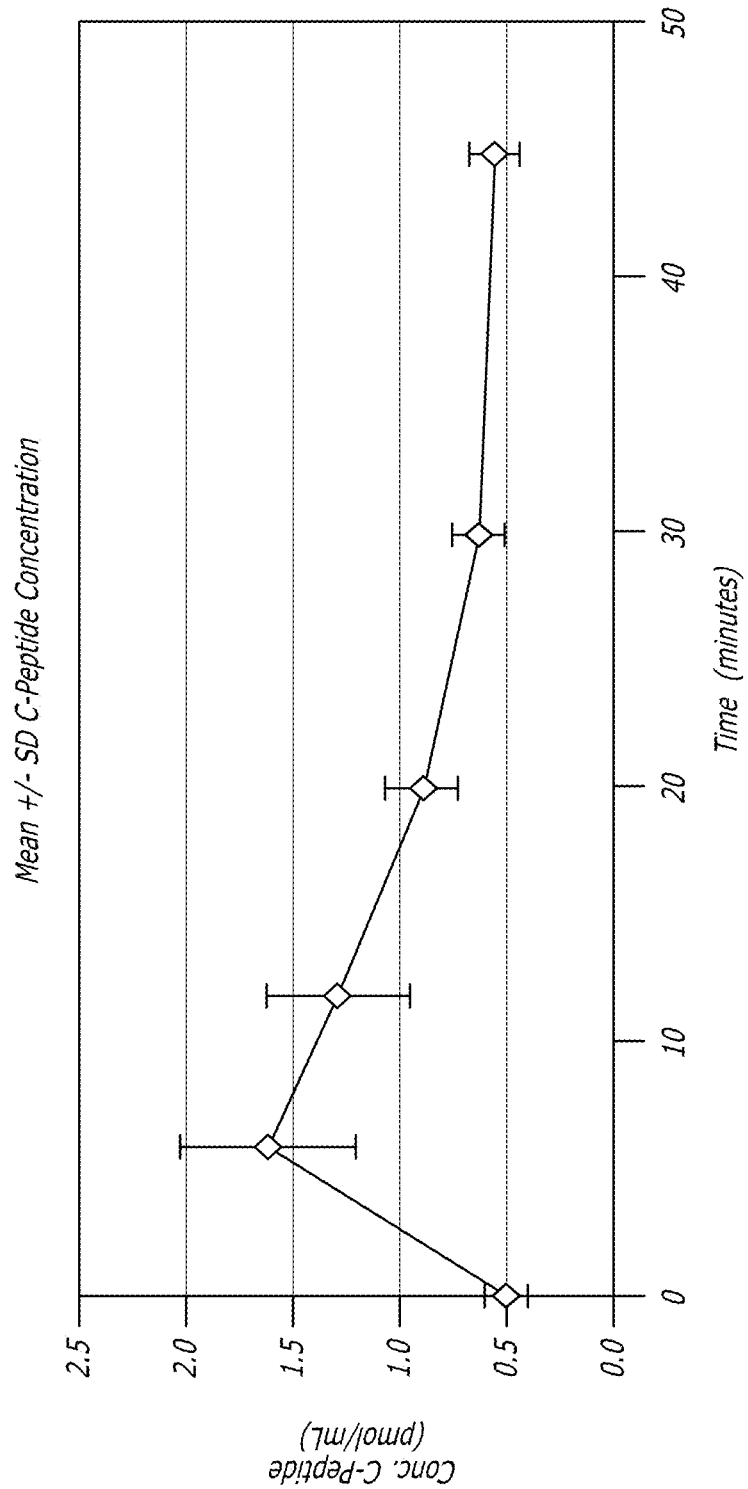
FIG. 3 depicts the mean plasma concentration of the C-peptide in subjects treated with an inhalable dry powder formulation containing a GLP-1 dose of 1.5 mg measured at various times after inhalation.

FIG. 3 depicts the plasma C-peptide concentrations in subjects treated with an inhalable dry powder formulation containing a GLP-1 dose of 1.5 mg measured at various times after inhalation. The data demonstrate that C-peptide is released following GLP-1 inhalation confirming endogenous insulin release.

Figure 4:
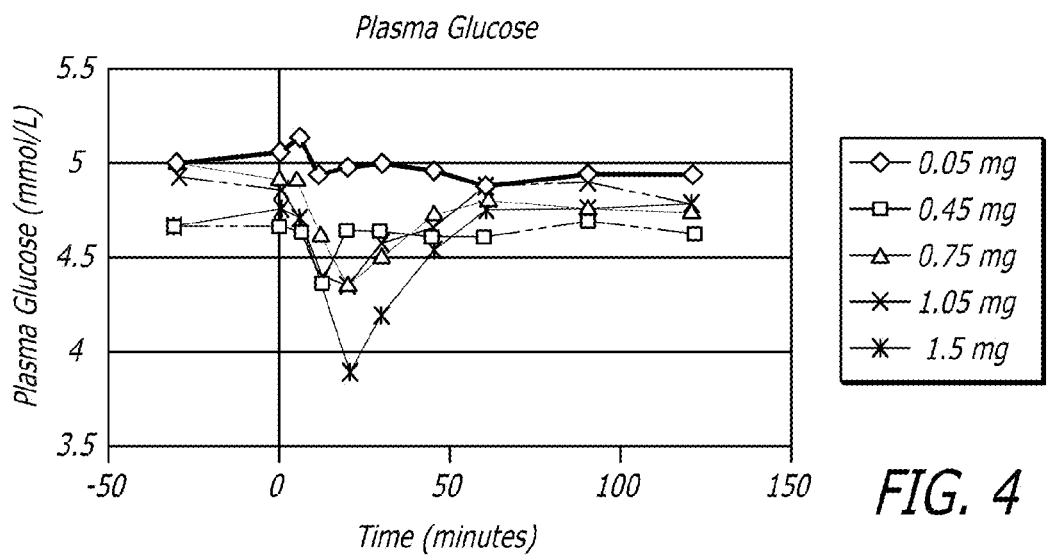
FIG. 4 depicts the mean plasma concentration of glucose in subjects treated with an inhalable dry powder formulation containing GLP-1 doses of 0.05 mg, 0.45 mg, 0.75 mg, 1.05 mg and 1.5 mg, measured at various times after inhalation.

FIG. 4 depicts fasting plasma glucose concentrations in subjects treated with the GLP-1 formulation containing GLP-1. Mean fasting plasma glucose (FPG) concentrations were approximately 4.7 mmol/L for those receiving the 1.5 mg dose. GLP-1 mediated insulin release is glucose dependent. Hypoglycemia is not historically observed in euglycemic subjects. In this experiment, the data clearly show that glucose concentrations in these euglycemic healthy subjects were reduced following pulmonary administration of GLP-1. At the 1.5 mg GLP-1 dose, two of the six subjects had glucose concentrations lowered by GLP-1 to below 3.5 mmol/L, the laboratory value that defines hypoglycemia. Plasma glucose decreased more than 1.5 mol/L in two of the six subjects who received the 1.5 mg GLP-1 dose. Moreover, decreases in plasma glucose were correlated to the GLP-1 dose. The smallest decrease in glucose concentration was seen with the 0.05 mg dose, and the largest decrease was seen with the 1.5 mg dose. The three intermediate doses of GLP-1 produced roughly equal decreases in plasma glucose. The data indicate that the GLP-1 glucose-dependency was overcome based on GLP-1 concentrations above the physiologic range. Physiologic ranges for GLP-1(7-36) amide in normal individuals has been reported to be in the range of 5-10 pmol/L during fasting, and increase rapidly after eating to 15 to 50 pmol/L (Drucker, D. and Nauck, M. The Lancet 368:1696-1705, 2006).

Figure 5:
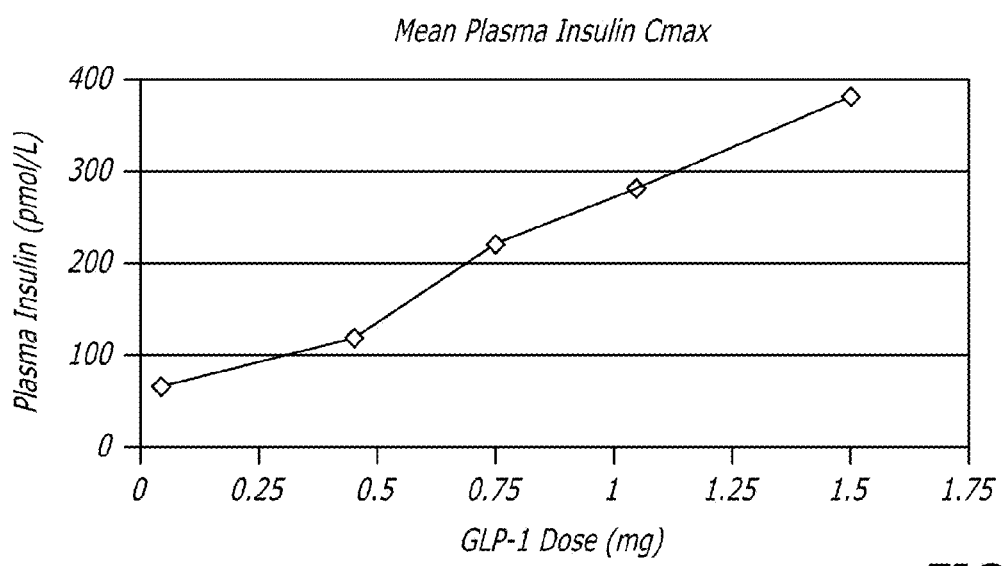
FIG. 5 depicts mean plasma insulin concentrations in patients treated with an inhalable dry powder formulation containing GLP-1 doses of 0.05 mg, 0.45 mg, 0.75 mg, 1.05 mg and 1.5 mg. The data shows that insulin secretion in response to pulmonary GLP-1 administration is dose dependent.

FIG. 5 further depicts the dose dependent insulin concentrations in plasma after pulmonary administration of GLP-1.

In most subjects, the insulin release was not sustained, since plasma insulin concentration fell rapidly after the initial response to GLP-1 administration. In most subjects, the peak plasma insulin response ranged from 200-400 pmol/L with one subject exhibiting peak plasma insulin levels that exceeded 700 pmol/L. Thus, the data indicate that insulin response is GLP-1 dose dependent.

Figure 6:
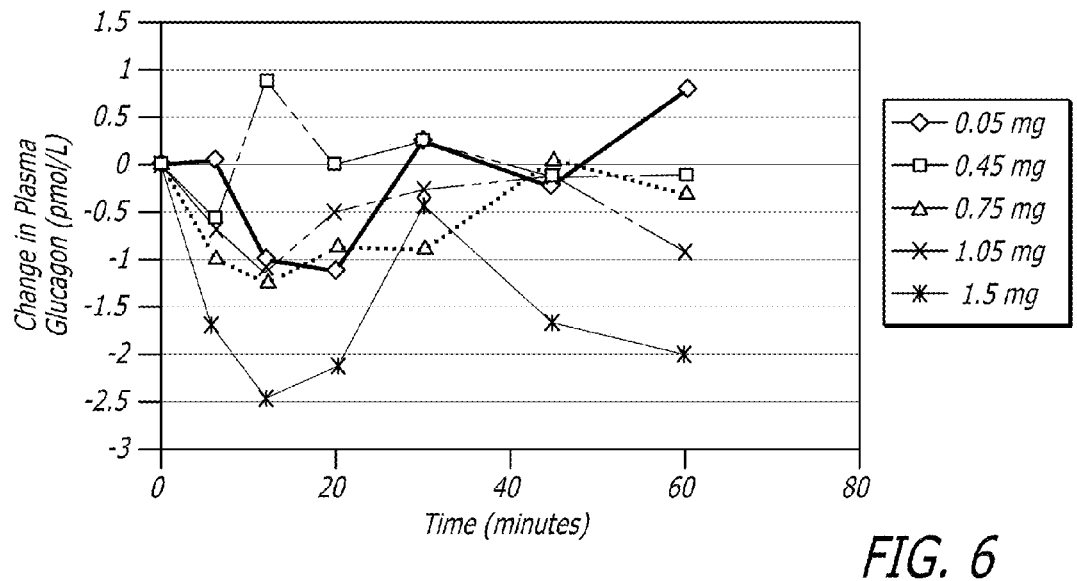
FIG. 6 depicts mean plasma glucagon concentrations in patients treated with an inhalable dry powder formulation containing GLP-1 doses of 0.05 mg, 0.45 mg, 0.75 mg, 1.05 mg and 1.5 mg.

FIG. 6 depicts glucagon concentrations in plasma after GLP-1 pulmonary administration at the various dosing groups. Baseline glucagon levels ranged from 13.2 pmol/L to 18.2 pmol/L in the various dose groups. The maximum change in plasma glucagon was seen at 12 min after dosing. The largest decrease in plasma glucagon was approximately 2.5 pmol/L and was seen in the 1.5 mg dose group. The maximum suppression of glucagon secretion was potentially underestimated because the minima did not always occur at 12 min.

Tables 2 and 3 report the adverse events or side effect symptoms recorded for the patient population in the study. The list of adverse events reported in the literature for GLP-1 administered by injection is not extensive; and those reported have been described as mild or moderate, and tolerable. The primary adverse events reported have been profuse sweating, nausea and vomiting when active GLP-1 concentrations exceed 100 pmol/L. As shown in Tables 1 and 3, and FIG. 1, pulmonary administration at doses of 1.05 mg and 1.5 mg resulted in active GLP-1 concentrations greatly exceeding 100 pmol/L without the side effects normally observed with parenteral (subcutaneous, intravenous [either bolus or infusion]) GLP-1. None of the subjects in this study reported symptoms of nausea, profuse sweating or vomiting. Subjects in Cohort 5 reached $C_{max}$ comparable to that observed with a 50 µg/kg IV bolus data (reported by Vilsboll et al. 2000), where the majority of subjects reported significant adverse events.

TABLE 2

Adverse Events

| Adverse Event | 0.05 mg (n = 4) | 0.45 mg (n = 4) | 0.75 mg (n = 6) | 1.05 mg (n = 6) | 1.5 mg (n = 6) |
|---|---|---|---|---|---|
| Cough | 3 | 1 | 3 | 5 | 5 |
| Dysphonia | 2 | — | 2 | 3 | 3 |
| Productive Cough | — | — | 1 | — | — |
| Throat Irritation | — | — | — | 1 | — |
| Headache | 1 | 1 | — | 1 | 1 |
| Dizziness | — | — | — | — | 2 |
| Dysgeusia | — | — | 1 | — | — |
| Fatigue | — | — | 1 | 1 | 1 |
| Seasonal Allergy | — | — | — | 1 | — |
| Rhinitis | — | — | — | 1 | — |
| Increased Appetite | — | — | — | — | 1 |

TABLE 3

Comparative Adverse Events of GLP-1:
IV vs. Pulmonary Administration

| Adverse Events | IV[†] (16.7 µg) | IV[†]* (50 µg) | Pulmonary* (1.5 mg) |
|---|---|---|---|
| Reduced well-being | 42% | 100% | 17% |
| Nausea | 33% | 83% | 0% |
| Profuse sweating | 17% | 67% | 0% |

[†]Vilsboll et al. Diabetes Care, June 2000;
*Comparable $C_{max}$

Tables 2 and 3 show there were no serious or severe adverse events reported by any subjects in the study who received GLP-1 by pulmonary inhalation. The most commonly reported adverse events were those associated with inhalation of a dry powder, cough and throat irritation. Surprisingly, in the patients treated by pulmonary inhalation, no subject reported nausea or dysphoria, and there was no vomiting associated with any of these subjects. The inventors also found that pulmonary administration of GLP-1 in a dry powder formulation lack inhibition of gastric emptying in the above subjects (data not shown). Inhibition of gastric emptying is a commonly encountered unwanted side effect associated with injected standard formulations of GLP-1.

In summary, the clinical GLP-1/FDKP powder contained up to 15 wt % GLP-1 providing a maximum dose of 1.5 mg GLP-1 in 10 mg of powder. Andersen cascade measurements indicated that 35-70% of the particles had aerodynamic diameters <5.8 µm. A dose of 1.5 mg GLP-1 produced mean peak concentrations >300 pmol/L of active GLP-1 at the first sampling time (3 min); resulted in mean peak insulin concentrations of 375 pmol/L at the first measured time point (6 min); reduced mean fasting plasma glucose from 85 to 70 mg/dL 20 min after dosing; and was well tolerated and did not cause nausea or vomiting.

Example 2

Comparison of Pulmonary Administration of GLP-1 and Exenatide, and Subcutaneous Administration of Exenatide to male Zucker Diabetic Fat Rats Much effort has been expended in developing analogs of GLP-1 with longer circulating half-lives to arrive at a clinically useful treatment. As demonstrated herein, pulmonary administration of GLP-1 also provides clinically meaningful activity. It was thus of interest to compare these two approaches.

Preparation of FDKP Particles.

Fumaryl diketopiperazine (FDKP) and polysorbate 80 were dissolved in dilute aqueous ammonia to obtain a solution containing 2.5 wt % FDKP and 0.05 wt % polysorbate 80. The FDKP solution was then mixed with an acetic acid solution containing polysorbate 80 to form particles. The particles were washed and concentrated by tangential flow filtration to achieve approximately 11% solids by weight.

Preparation of GLP-1 Stock Solution.

A 10 wt % GLP-1 stock solution was prepared in deionized water by combining 60 mg GLP-1 solids (86.6% peptide) with 451 mg deionized water. About 8 µL glacial acetic acid was added to dissolve the peptide.

Preparation of GLP-1/FDKP Particles.

A 1 g portion of the stock FDKP suspension (108 mg particles) was transferred to a 2 mL polypropylene tube. The appropriate amount of GLP-1 stock solution was added to the suspension and gently mixed. The pH of the suspension was adjusted from pH ~3.5 to pH ~4.5 by adding 1 µL aliquots of 50% (v/v) ammonium hydroxide. The GLP-1/FDKP particle suspension was then pelleted into liquid nitrogen and lyophilized. The dry powders were assayed by high performance liquid chromatography (HPLC) to confirm drug content.

Preparation of Exenatide Stock Solution.

A 10 wt % exendin stock solution was prepared in 2% wt acetic acid by combining 281 mg exendin solids (88.9% peptide) with 2219 mg 2% wt acetic acid.

Preparation of Exenatide/Fdkp Particles.

A 1533 mg portion of a stock FDKP particle suspension (171 mg particles) was transferred to a 4 mL glass vial. A 304 mg portion of exendin stock solution was added to the suspension and gently mixed. The pH of the suspension was adjusted from pH ~3.7 to pH ~4.5 by adding 3-5 µL aliquots of 25% (v/v) ammonium hydroxide. The exenatide/FDKP particle suspension was then pelleted into liquid nitrogen and lyophilized. The dry powders were assayed by high performance liquid chromatography (HPLC) to confirm drug content.

Pharmacokinetic and Pharmacodynamic Assessment in Rats.

Male Zucker Diabetic Fatty (ZDF) rats (5/group) were assigned to one of four test groups. Animals were fasted overnight then administered glucose (1 g/kg) by intraperitoneal injection immediately prior to test article dosing. Animals in the control group received air by pulmonary insufflation. Animals in Group 1 received exenatide (0.3 mg) in saline (0.1 mL) by subcutaneous (SC) injections. Animals in Group 2 received 15% by weight exenatide/FDKP (2 mg) by pulmonary insufflation. Animals in Group 3 received 15% by weight GLP-1/FDKP (2 mg) by pulmonary insufflation. Blood samples were collected from the tail prior to dosing and at 15, 30, 45, 60, 90, 120, 240, and 480 min after dosing. Plasma was harvested. Blood glucose and plasma GLP-1 or plasma exenatide concentrations were determined.

Exenatide pharmacokinetics are reported in FIG. 7A. These data showed that exanetide is absorbed rapidly following insufflation of exenatide/FDKP powder. The bioavailability of the inhaled exenatide was 94% compared to subcutaneous injection. This may indicate that pulmonary administration is particularly advantageous to exenatide. The time to maximum peak circulating exenatide concentrations ($T_{max}$) was 30 min in rats receiving subcutaneous exenatide compared to <15 min in rats receiving inhaled exenatide. This $T_{max}$ was similar to that of insufflated GLP-1/FDKP (data not shown).

Figure 7:
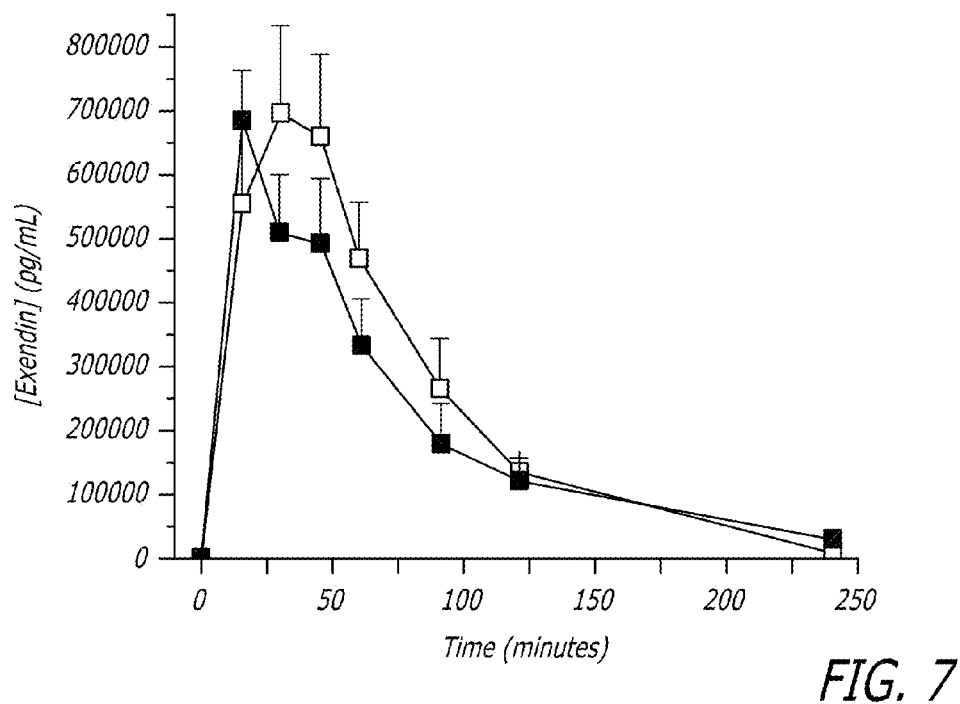
FIG. 7 depicts the mean plasma exendin concentrations in male Zucker Diabetic Fatty (ZDF) rats receiving exendin-4/FDKP (fumaryl diketopiperazine) powder by pulmonary insufflation versus subcutaneous (SC) administered exendin-4. The closed squares represent the response following pulmonary insufflation of exendin-4/FDKP powder. The open squares represent the response following administration of exendin-4. Data are plotted as means±SD.
Figure 8:
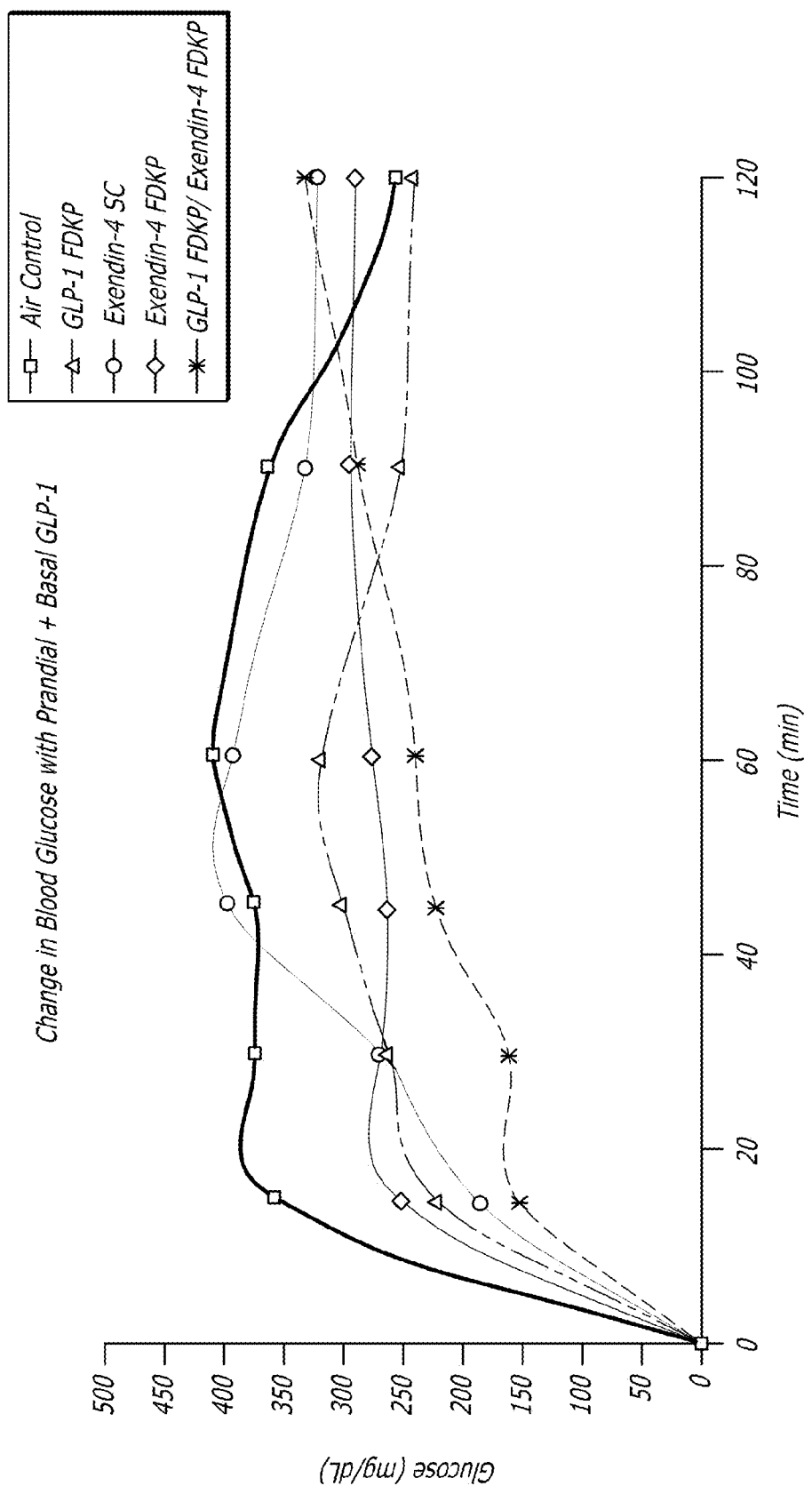
FIG. 8 depicts changes in blood glucose concentration from baseline in male ZDF rats receiving either air control, exendin-4/FDKP powder, or GLP-1/FDKP powder by pulmonary insufflation versus subcutaneously administered exendin-4. The graph also shows a combination experiment in which the rats were administered by pulmonary insufflation an inhalation powder comprising GLP-1/FDKP, followed by an inhalation powder comprising exendin-4/FDKP. In the graph, the closed diamonds represent the response following pulmonary insufflation of exendin-4/FDKP powder. The closed circles represent the response following administration of subcutaneous exendin-4. The triangles represent the response following administration of GLP-1/FDKP powder. The squares represent the response following pulmonary insufflation of air alone. The stars represent the response given by 2 mg of GLP-1/FDKP given to the rats by insufflation followed by a 2 mg exendin-4/FDKP powder administered also by insufflation.

Comparative pharmacodynamics are reported in FIG. 8. These data showed the changes in blood glucose for all four test groups. Glucose excursions following the glucose tolerance test were lower in animals receiving inhaled exenatide/FDKP as compared to animals receiving SC exenatide. Since exenatide exposure was comparable in both groups (FIG. 7), these data suggest that the shorter time to peak exenatide concentrations in the exenatide/FDKP group provided better glucose control. Additionally, glucose excursions were comparable in animals receiving either GLP-1/FDKP or exenatide/FDKP. These data are surprising because the circulating half-life of exenatide (89 min) is considerably longer than that of GLP-1(15 min). Indeed, exenatide was developed to maximize circulating half-life for the purpose of increasing efficacy. These data suggest that the longer circulating half-life of exenatide offers no advantage in controlling hyperglycemia when using pulmonary administration. Moreover pulmonary administration of either molecule provided superior blood glucose control the SC exenatide.

FIG. 7 depicts mean plasma exendin concentrations in male ZDF rats receiving exendin-4/FDKP powder formulation administered by pulmonary insufflation versus subcutaneous exendin-4. The closed squares represent the response following pulmonary insufflation of exendin-4/FDKP powder. The open squares represent the response following administration of subcutaneously administered exendin-4. The data are plotted as ±standard deviation. The data show that rats insufflated with powders providing GLP-1 doses of 0.12, 0.17, and 0.36 mg produced maximum plasma GLP-1 concentrations ($C_{max}$) of 2.3, 4.9 and 10.2 nM and exposures (AUC) of 57.1 nM·min, 92.6 nM·min, and 227.9 nM·min, respectively ($t_{max}$=10 min, $t_{1/2}$=10 min). In an intraperitoneal glucose tolerance test conducted after 4 consecutive days of dosing 0.3 mg GLP-1 per day, treated animals exhibited significantly lower glucose concentrations than the control group (p<0.05). At 30 min post-challenge, glucose increased by 47% in control animals but only 17% in treated animals.

FIG. 8 depicts the change in blood glucose from baseline in male ZDF rats receiving either air control, exendin-4/FDKP powder, or GLP-1/FDKP powder by pulmonary insufflation versus subcutaneous exendin-4 and exendin-4 administered by pulmonary insufflation. The closed diamonds represent the response following pulmonary insufflation of exendin-4/FDKP powder. The closed circles represent the response following administration of subcutaneous exendin-4. The closed triangles represent the response following administration of GLP-1/FDKP powder. The closed squares represent the response following pulmonary insufflation of air alone. The open squares represent the response given by 2 mg of GLP-1/FDKP given to the rats by insufflation followed by a 2 mg exendin-4/FDKP powder administered also by insufflation.

Example 3

Oxyntomodulin/FDKP Powder Preparation.

Oxyntomodulin, also known as glucagon-37, is a peptide consisting of 37 amino acid residues. The peptide was manufactured and acquired from American Peptide Company, Inc. of Sunnyvale, Calif. FDKP particles in suspension were mixed with an oxyntomodulin solution, then flash frozen as pellets in liquid nitrogen and lyophilized to produce sample powders.

Six powders were prepared with target peptide content between 5% and 30%. Actual peptide content determined by HPLC was between 4.4% and 28.5%. The aerodynamic properties of the 10% peptide-containing powder were analyzed using cascade impaction.

The FDKP solution was mixed with an acetic acid solution containing polysorbate 80 to form particles. The particles were washed and concentrated by tangential flow filtration to achieve approximately 11% solids by weight.

FDKP particle suspension (1885 mg×11.14% solids=210 mg FDKP particles) was weighed into a 4 mL clear glass vial. The vial was capped and mixed using a magnetic stirrer to prevent settling. Oxyntomodulin solution (909 mg of 10% peptide in 2 wt % acetic acid) was added to the vial and allowed to mix. The final composition ratio was approximately 30:70 oxyntomodulin:FDKP particles. The oxyntomodulin/FDKP suspension had an initial pH of 4.00 which was adjusted to pH 4.48 by adding 2-10 µL increments of 1:4 (v/v) ammonium hydroxide/water. The suspension was pelleted into a small crystallization dish containing liquid nitrogen. The dish was placed in a freeze dryer and lyophilized at 200 mTorr. The shelf temperature was ramped from −45° C. to 25° C. at 0.2° C./min and then held at 25° C. for approximately 10 hours. The resultant powder was transferred to a 4 mL clear glass vial. Total yield of the powder after transfer to the vial was 309 mg (103%). Samples were tested for oxyntomodulin content by dissolving the oxyntomodulin preparation in sodium bicarbonate and assaying by high pressure liquid chromatography in a Waters 2695 separations system using deionized with 0.1% trifluoroacetic acid (TFA) and acetonitrile with 0.1% TFA as mobile phases, with the wavelength detection set at 220 and 280 nm. Data was analyzed using a Waters Empower™ software program.

Pharmacokinetic and Pharmacodynamic Assessment in Rats.

Figure 9A:
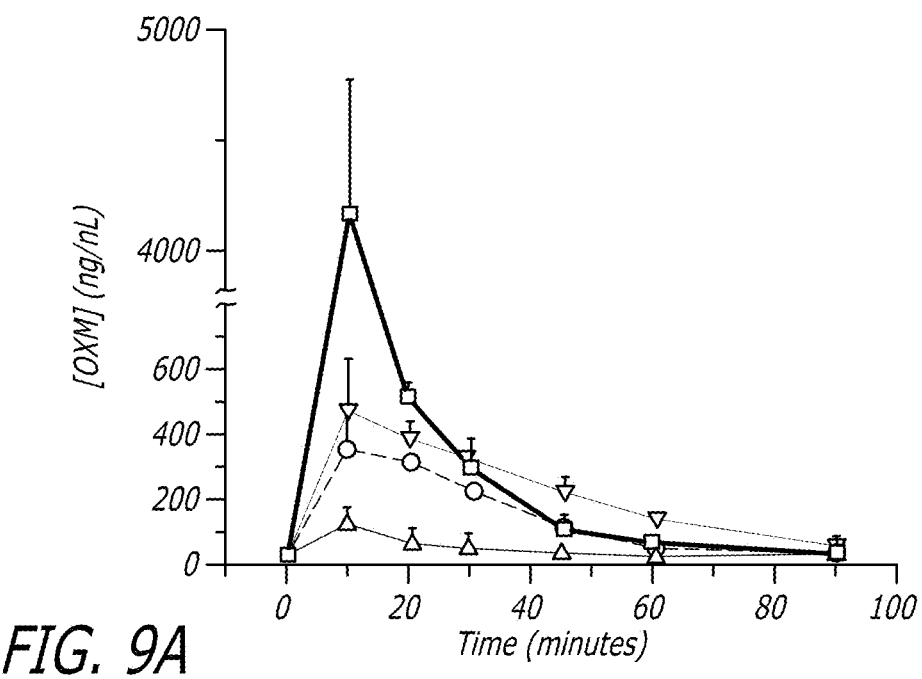
FIG. 9A depicts the mean plasma oxyntomodulin concentrations in male ZDF rats receiving oxyntomodulin/FDKP powder by pulmonary insufflation versus intravenous (IV) oxyntomodulin. The squares represent the response following IV administration of oxyntomodulin alone. The up triangles represent the response following pulmonary insufflation of 5% oxyntomodulin/FDKP powder (0.15 mg oxyntomodulin). The circles represent the response following pulmonary insufflation of 15% oxyntomodulin/FDKP powder (0.45 mg oxyntomodulin). The down triangles represent the response following pulmonary insufflation of 30% oxyntomodulin/FDKP powder (0.9 mg oxyntomodulin). Data are plotted as means±SD.

Male ZDF rats (10/group) were assigned to one of four groups. Animals in the one group received oxyntomodulin by intravenous injection. Animals in the other three groups received 5% oxyntomodulin/FDKP powder (containing 0.15 mg oxyntomodulin), 15% oxyntomodulin/FDKP powder (containing 0.45 mg oxyntomodulin), or 30% oxyntomodulin/FDKP powder (containing 0.9 mg oxyntomodulin) by pulmonary insufflation. Blood samples were collected from the tail prior to dosing and at various times after dosing for measurement of plasma oxyntomodulin concentrations (FIG. 9A). Food consumption was also monitored at various times after dosing with oxyntomodulin (FIG. 9B).

FIG. 9A is a graph comparing the plasma concentrations of oxyntomodulin following administration of an inhalable dry powder formulation at various amounts in male ZDF rats and control rats receiving oxyntomodulin by intravenous injection. These data show that oxyntomodulin is absorbed rapidly following insufflation of oxyntomodulin/FDKP powder. The time to maximum peak circulating oxyntomodulin concentrations ($T_{max}$) was less than 15 min in rats receiving inhaled oxyntomodulin. This study shows that the half life of oxyntomodulin is from about 22 to about 25 min after pulmonary administration.

Figure 9B:
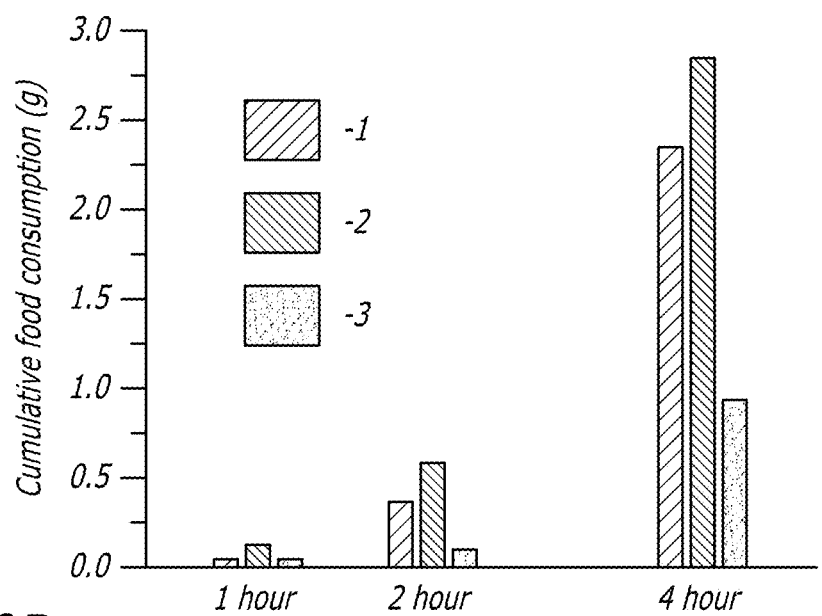
FIG. 9B depicts the cumulative food consumption in male ZDF rats receiving 30% oxyntomodulin/FDKP powder (0.9 mg oxyntomodulin) by pulmonary insufflation (1); oxyntomodulin alone (1 mg oxyntomodulin) by IV injection (2); or air control (3).

FIG. 9B is a bar graph showing cumulative food consumption in male ZDF rats treated with intravenous oxyntomodulin or oxyntomodulin/FDKP powder administered by pulmonary insufflation compared to control animals receiving an air stream. The data show that pulmonary administration of oxyntomodulin/FDKP reduced food consumption to a greater extent than either intravenous oxyntomodulin or air control with a single dose.

In a similar set of experiments, rats received an air stream as control (Group 1) or 30% oxyntomodulin/FDKP powder by pulmonary insufflation. Rats administered oxyntomodulin/FDKP inhalation powder received doses of either 0.15 mg oxyntomodulin (as 0.5 mg of oxyntomodulin/FDKP powder; Group 2), 0.45 mg oxyntomodulin (as 1.5 mg of oxyntomodulin/FDKP powder, Group 3) or 0.9 mg oxyntomodulin (as 3 mg of oxyntomodulin/FDKP powder, Group 4) prepared as described above. The studies were conducted in ZDF rats fasted for 24 hr prior to the start of the experiment. Rats were allowed to eat after receiving the experimental dose. A predetermined amount of food was given to the rats and the amount of food the rats consumed was measured at various times after the start of the experiment. The oxyntomodulin/FDKP dry powder formulation was administered to the rats by pulmonary insufflation and food measurements and blood samples were taken at various points after dosing.

Figure 10A:
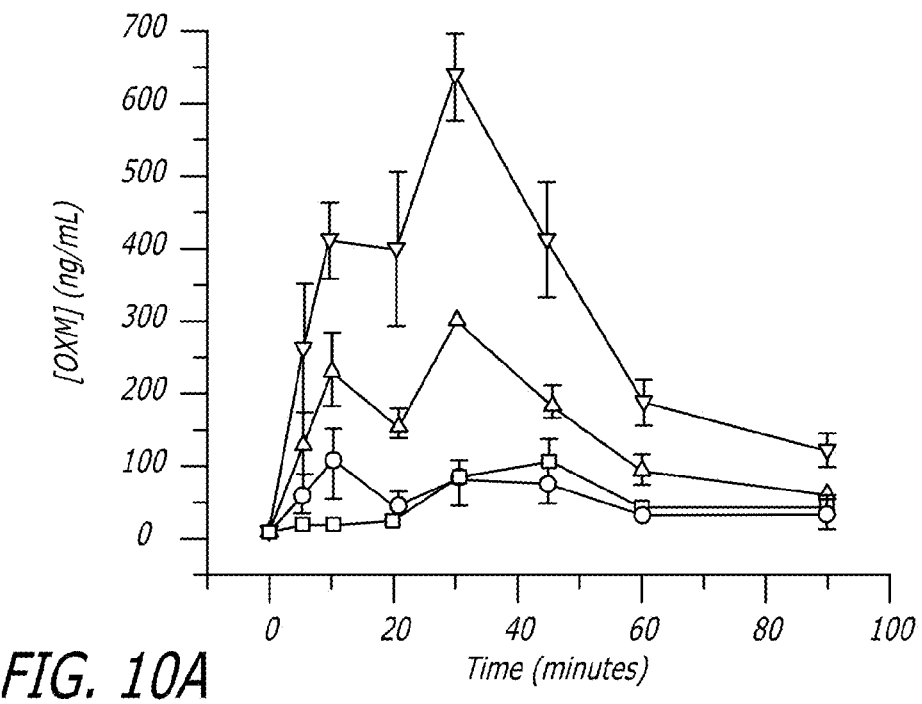
FIG. 10A depicts the mean plasma oxyntomodulin concentrations in male ZDF rats receiving oxyntomodulin/FDKP powder by pulmonary insufflation versus air control. The squares represent the response following administration of air control. The circles represent the response following pulmonary insufflation of oxyntomodulin/FDKP powder (0.15 mg oxyntomodulin). The up triangles represent the response following pulmonary insufflation of oxyntomodulin/FDKP powder (0.45 mg oxyntomodulin). The down triangles represent the response following pulmonary insufflation of oxyntomodulin/FDKP powder (0.9 mg oxyntomodulin). Data are plotted as means±SD.
Figure 10B:
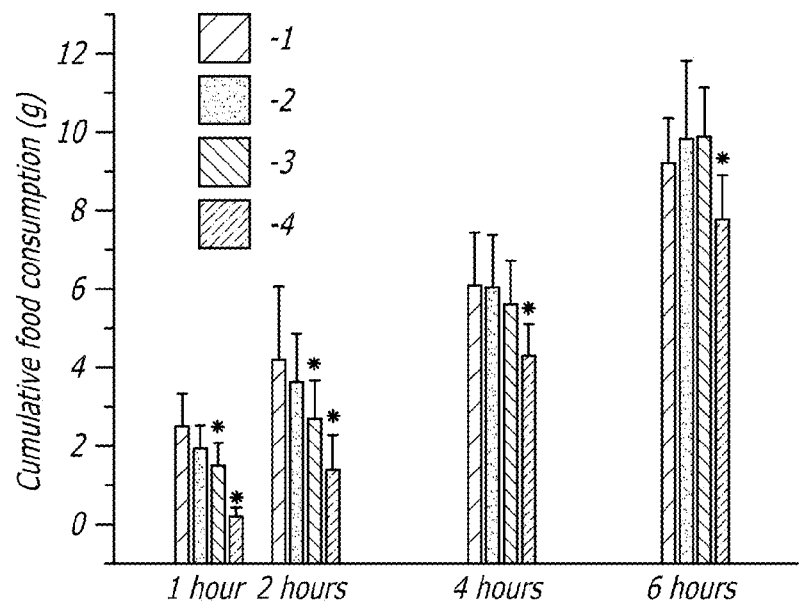
FIG. 10B depicts data from experiments showing cumulative food consumption in male ZDF rats receiving 30% oxyntomodulin/FDKP powder at varying doses including 0.15 mg oxyntomodulin (1); 0.45 mg oxyntomodulin (2); or 0.9 mg oxyntomodulin (3) by pulmonary insufflation compared to air control (4). Data are plotted as means±SD. An asterisk (*) denotes statistical significance.

FIGS. 10A and 10B show circulating oxyntomodulin concentrations for all test animals and the change in food consumption from control, respectively. Rats given oxyntomodulin consumed significantly less food than the control rats for up to 6 hr after dosing. Higher doses of oxyntomodulin appeared to suppress appetite more significantly that the lower doses indicating that appetite suppression is dose dependent, as the rats given the higher dose consumed the least amount of food at all time points measured after dosing.

Maximal concentrations of oxyntomodulin in blood were detected at 10 to 30 min and that maximal concentration of oxyntomodulin was dose dependent as the rats receiving 1.5 mg of oxyntomodulin had a maximal plasma concentration of 311 µg/mL and rats receiving 3 mg of oxyntomodulin had a maximal plasma concentration of 660 µg/mL. The half-life ($t_{1/2}$) of oxyntomodulin in the Sprague Dawley rats after administration by pulmonary insufflation ranged from about 25 to 51 min.

Example 4

Administration of GLP-1 in an Inhalable Dry Powder to Type 2 Diabetic Patients A Phase 1 clinical trial of GLP-1/FDKP inhalation powder was conducted in patients suffering with Type 2 diabetes mellitus to assess the glucose levels of the patients before and after treatment with GLP-1 dry powder formulation by pulmonary inhalation. These studies were conducted according to Example 1 and as described herein. GLP-1 inhalation powder was prepared as described in U.S. patent application Ser. No. 11/735,957, which disclosure is incorporated herein by reference. The dry inhalation powder contained 1.5 mg of human GLP-1(7-36) amide in a total of 10 mg dry powder formulation containing FDKP in single dose cartridge. For this study, 20 patients with Type 2 diabetes, including adult males and postmenopausal females, were fasted overnight and remained fasted for a period of 4 hr after GLP-1 inhalation powder administration. The dry powder formulation was administered using the MedTone® dry powder inhaler (MannKind Corporation), and described in U.S. patent application Ser. No. 10/655,153, which disclosure is incorporated herein by reference in its entirety.

Blood samples for assessing serum glucose levels from the treated patients were obtained at 30 min prior to dosing, at dosing (time 0), and at approximately 2, 4, 9, 15, 30, 45, 60, 90, 120 and 240 min following GLP-1 administration. The serum glucose levels were analyzed for each sample.

Figure 11:
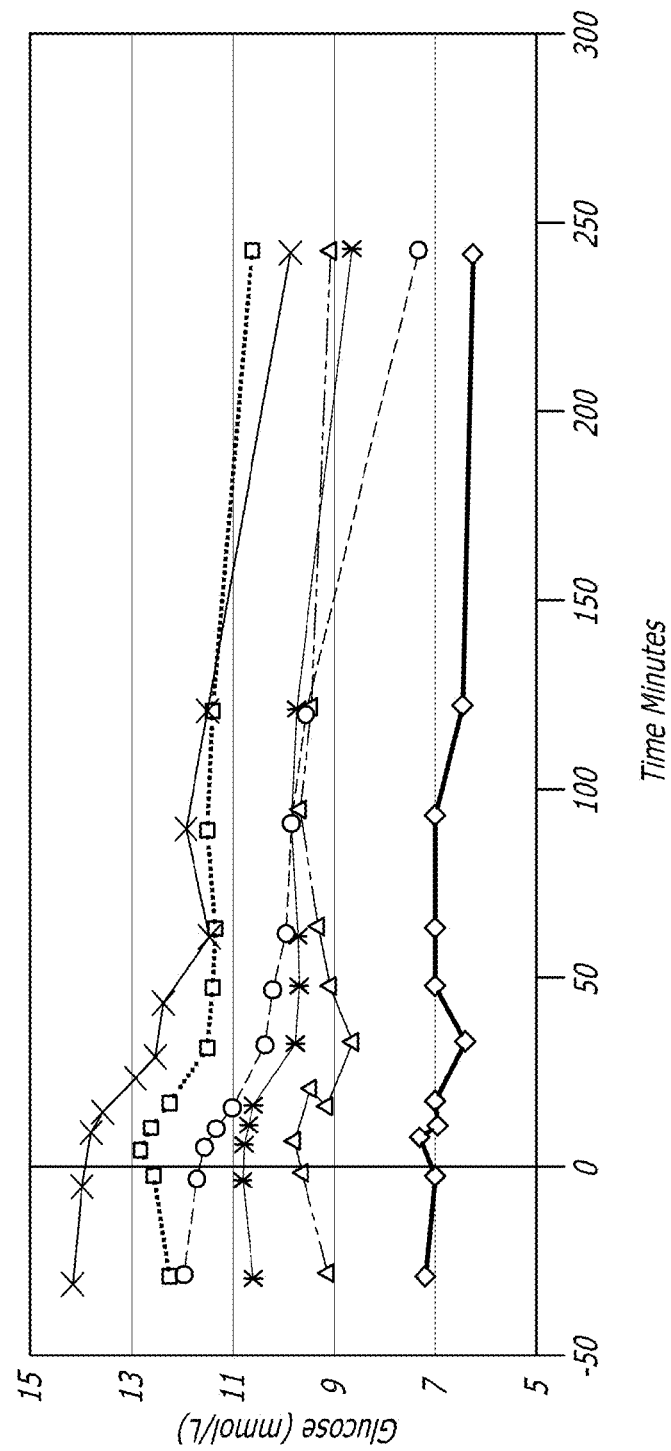
FIG. 11 depicts the glucose values obtained from six fasted Type 2 diabetic patients following administration of a single dose of an inhalable dry powder formulation containing GLP-1 at various time points.

FIG. 11 is a graph showing the results of these studies and depicts the glucose values obtained from six fasted patients with Type 2 diabetes following administration of a single dose of an inhalable dry powder formulation containing GLP-1 at various time points. The glucose values for all six patients decreased following administration of GLP-1 and remained depressed for at least 4 hrs after administration at the termination of the study.

Figure 12:
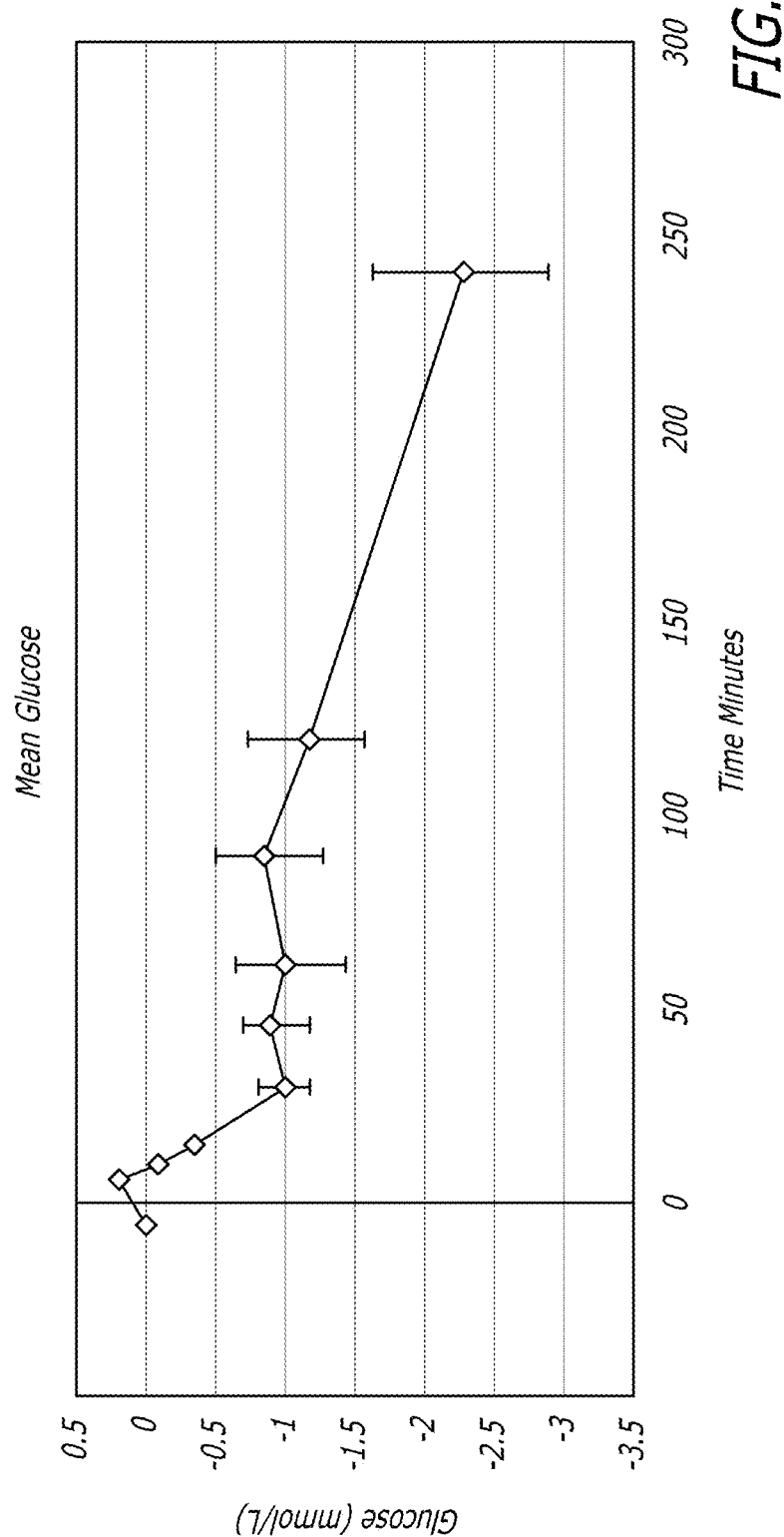
FIG. 12 depicts the mean glucose values for the group of six fasted Type 2 diabetic patients of FIG. 11, in which the glucose values are expressed as the change of glucose levels from zero time (dosing) for all six patients.

FIG. 12 is a graph showing the mean glucose values for the group of six fasted patients with Type 2 diabetes whose glucose values are shown in FIG. 11. In FIG. 12, the glucose values are expressed as the mean change of glucose levels from zero time (dosing) for all six patients. FIG. 12 shows a mean glucose drop of approximately 1 mmol/L, which is approximately equivalent to from about 18 mg/dL to about 20 mg/dL, is attained by the 30 min time point. This mean drop in glucose levels to last for 120 min. The changes are larger in subjects with higher baseline glucose and more prolonged, whereas in 2 of the 6 subjects, the subjects with the lowest baseline fasted blood glucose, showed only a transient lowering of glucose levels in this timeframe (data not shown). It was noted that those with higher fasting glucose do not typically have the same insulin response as those with lower values, so that when stimulated, those subjects with higher fasting glucose typically exhibit a greater response than those whose glucose value are closer to normal.

Example 5

First Pass Distribution Model of Intact GLP-1 to Brain and Liver

First pass distribution of GLP-1 through the systemic circulation following pulmonary delivery and intravenous bolus administration was calculated to determine the efficacy of delivery for both methods of GLP-1 administration. A model was developed based on the assumptions that: (1) the absorption of GLP-1 from the lungs and into the pulmonary veins exhibited zero-order kinetics; (2) the distribution of GLP-1 to the brain and within the brain occurs instantaneously, and (3) clearance of GLP-1 from the brain and liver distribution is driven by basal blood flow only. Based on these assumptions, the analysis to determine the amount of GLP-1 in the brain and liver was based on published data with respect to extraction of GLP-1 by certain tissues and organs (Deacon, C. F. et al. "Glucagon-like peptide 1 undergoes differential tissue-specific metabolism in the anesthetized pig." *American Physiological Society*, 1996, pages E458-E464), and blood flow distribution to the body and rate due to cardiac output from human studies (Guyton Textbook of Physiology, 10$^{th}$ Edition; W. B. Saunders, 2000, page 176). In a normal subject (70 kg) having normal physiological parameters such as blood pressure at resting, the basal flow rate to the brain and liver are 700 mL/min and 1350 mL/min, respectively. Based on cardiac output, blood flow distribution to the body has been calculated to be 14% to the brain, 27% to the liver and 59% to remaining body tissues (Guyton).

Using the above-mentioned parameters, the relative amounts of GLP-1 that would be distributed to the brain and liver for a 1 mg dose given by pulmonary and intravenous administration were determined. One mg of GLP-1 was divided by 60 seconds, and the resultant number was multiplied by 14% flow distribution to the brain. Therefore, every second a fraction of the dose is appearing in the brain. From the data available indicating that blood in the brain is equal to 150 mL and the clearance rate is 700 mL/min, the calculations on clearance of GLP-1 yields about 12 mL/second, which equals approximately 8% of the blood volume being cleared from the brain per second. In the intravenous studies in pigs reported by Deacon et al., 40% of GLP-1 was instantaneously metabolized in the vein and 10% was also metabolized in the deoxygenated blood in the lung. Accordingly, 40% followed by another 10% of the total GLP-1 was subtracted from the total amount administered in the calculations with respect to the intravenous data analysis.

For the GLP-1 amounts estimated in the liver, the same degradation assumptions were made for the intravenous and pulmonary administration routes, with 40% followed by another 10% total amount loss for the IV dose. Twenty-seven percent of the remaining GLP-1 was assumed to be distributed to the liver, with 75% of the blood passing through the portal bed first. Instantaneous distribution of blood in the liver was assumed. Calculations were as follows: One mg of GLP-1 was divided by 60 seconds, 40% followed by another 10% of the total GLP-1 was subtracted from the total amount administered with respect to the intravenous data analysis. No degradation was assumed for the pulmonary administration. The resultant numbers were multiplied by 27% flow distribution to the liver, for both routes of administration, with 75% of this amount passing though the portal bed first. In the intravenous studies in pigs reported by Deacon et al., 20% extraction by the portal bed was reported; hence 75% of the amount of GLP-1 was reduced by 20% before being introduced into the liver. Therefore, the total amount of GLP-1 appearing in the liver every second is comprised of a fraction which has undergone metabolism in the portal bed. From the data available indicating that blood volume in the liver is equal to 750 mL and the clearance rate is 1350 mL/minute, the calculations on clearance of GLP-1 yields about 22.5 mL/second, which equals approximately 3% of the blood volume being cleared from the liver per second. Deacon et al. reported 45% degradation in the liver, accordingly, 45% of the total GLP-1 was subtracted from the total amount appearing in the liver, and the remainder was added to the total remaining amount.

The results of the calculations described above are presented in Tables 4 and 5. The calculated GLP-1 distribution in brain and liver after pulmonary administration (Table 4) are shown below:

TABLE 4

Pulmonary administration of 1 mg GLP-1

| Time in Seconds | Brain (µg) | Liver (µg) |
|---|---|---|
| 1 | 2.3 | 2.10 |
| 5 | 9.94 | 9.91 |
| 60 | 29.0 | 58.9 |

The results illustrating the distribution of GLP-1 after an intravenous bolus administration are shown in Table 5 below:

TABLE 5

Intravenous bolus administration of 1 mg GLP-1 over 1 minute

| Time in Seconds | Brain (µg) | Liver (µg) |
|---|---|---|
| 1 | 1.26 | 1.14 |
| 5 | 5.37 | 5.35 |
| 60 | 15.6 | 31.7 |

The calculations above are representative illustrations of the distribution of GLP-1 to specific tissues of the body after degradation of GLP-1 by endogenous enzymes. Based on the above determinations, the amounts of GLP-1 in brain and liver after pulmonary administration are about 1.82 to about 1.86 times higher than the amounts of GLP-1 after intravenous bolus administration. Therefore, the data indicate that pulmonary delivery of GLP-1 can be a more effective route of delivery when compared to intravenous administration of GLP-1, as the amount of GLP-1 at various times after administration would be about double the amount obtained with intravenous administration. Therefore, treatment of a disease or disorder comprising GLP-1 by pulmonary administration would require smaller total amounts, or almost half of an intravenous GLP-1 dose that is required to yield the same or similar effects.

Example 6

The studies in this example were conducted to measure the pharmacokinetic parameters of various active agents by subcutaneous administration and in formulations comprising a FDKP, FDKP disodium salt, succinyl-substituted-DKP (SDKP, also referred to herein as Compound 1) or asymmetrical (fumaryl-monosubstituted)-DKP (also referred herein as Compound 2) to ZDF rats administered by pulmonary insufflation. The rats were divided into 8 groups and five rats were assigned to each group. Each rat in Group 1 received a 0.3 mg dose of exendin-4 in phosphate buffered saline solution by pulmonary liquid instillation; Group 2 received 0.3 mg of exendin-4 in phosphate buffered saline by subcutaneous injection.

Rats in Groups 3-8 received their dosing of active agent or exendin-4 by pulmonary insufflation as follows: Group 3 rats received a 2 mg formulation of GLP-1/FDKP by pulmonary insufflation, followed by a 2 mg dose of exendin-4; Group 4 received a formulation of exendin-4/FDKP; Group 5 rats received a 3 mg dose of exendin-4 formulated as a 9.2% load in a disodium salt of FDKP; Group 6 rats received a 2 mg dose of exendin-4 formulated as a 13.4% load in a disodium salt of FDKP; Group 7 rats received a 2 mg dose of exendin-4 formulated as a 14.5% load in SDKP, and Group 8 rats received a 2 mg dose of exendin-4 formulated as a 13.1% load in asymmetrical (fumaryl-mono-substituted) DKP.

Figure 13:
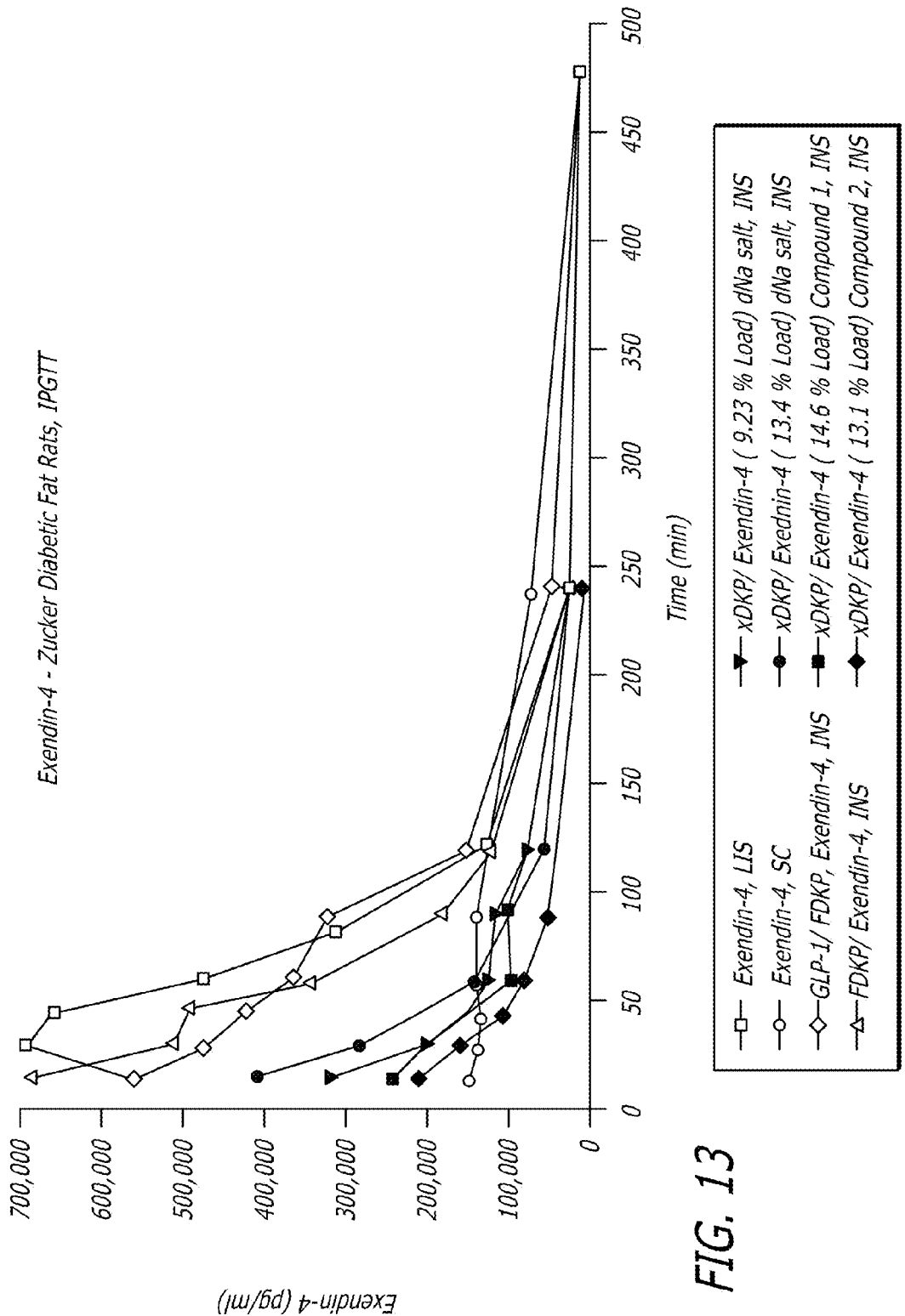
FIG. 13 depicts data obtained from experiments in which ZDF rats were administered exendin-4 in a formulation comprising a diketopiperazine or a salt of a diketopiperazine, wherein the exendin-4 was provided by various routes of administration (liquid installation (LIS), SC, pulmonary insufflation (INS)) in an intraperitoneal glucose tolerance test (IPGTT). In one group, rats were treated with exendin-4 in combination with GLP-1 by pulmonary insufflation.

The dosing of the animals occurred over the course of two days to accommodate the high number of subjects. The various test articles were administered to the animals and blood samples were taken at various times after dosing. Exendin-4 concentrations were measured in plasma isolates; the results for which are provided in FIG. 13. As depicted in the graph, Group 4 treated rats which received exendin-4 in a formulation containing FDKP exhibited high levels of exendin-4 in the blood earlier than 30 min and at higher levels than the rats in Group 2, which received exendin-4 by subcutaneous administration. In all groups, the levels of exendin-4 decrease sharply at about an hour after administration.

Administration of exendin-4/FDKP by pulmonary insufflation in ZDF rats has similar dose-normalized $C_{max}$, AUC, and bioavailability as exendin-4 administered as a subcutaneous injection. Exendin-4/FDKP administered by pulmonary insufflation showed a greater than two-fold half life compared to exendin-4 by subcutaneous injection. Exendin-4 administered as a fumaryl(mono-substituted)DKP, or SDKP formulation showed lower dose normalized $C_{max}$, AUC, and bioavailability compared to subcutaneous injection (approximately 50% less) but higher levels than pulmonary instillation.

After an overnight fast, ZDF rats were given a glucose challenge by intraperitoneal injection (IPGTT). Treatment with exendin-4/FDKP showed a greater reduction in blood glucose levels following the IPGTT compared to exendin-4 by the subcutaneous route. Compared to air control animals, blood glucose levels were significantly lowered following an IPGTT for 30 and 60 min in animals administered exendin-4 by subcutaneous injection and exendin-4/FDKP powder by pulmonary administration, respectively. Group 3 ZDF rats treated with exendin-4/FDKP and GLP-1 by pulmonary insufflation after intraperitoneal glucose administration (IPGTT) showed surprisingly lower blood glucose levels following IPGTT compared to either treatment alone at 30 min post dose (−28% versus −24%).

Example 7

The studies in this example were conducted to measure the pharmacokinetic and pharmacodynamic profile of peptide YY(3-36) formulations by pulmonary administration to ZDF rats compared to intravenous injections.

Preparation of PYY/FDKP formulation for pulmonary delivery: Peptide YY(3-36) (PYY) used in these experiments was obtained from American Peptide and was adsorbed onto FDKP particles as a function of pH. A 10% peptide stock solution was prepared by weighing 85.15 mg of PYY into an 8 ml clear vial and adding 2% aqueous acetic acid to a final weight of 762 mg. The peptide was gently mixed to obtain a clear solution. FDKP suspension (4968 mg, containing 424 mg of FDKP preformed particles) was added to the vial containing the PYY solution, which formed a PYY/FDKP particle suspension. The sample was placed on a magnetic stir-plate and mixed thoroughly throughout the experiment. A micro pH electrode was used to monitor the pH of the mixture. Aliquots of 2-3 µL of a 14-15% aqueous ammonia solution were used to incrementally increase the pH of the sample. Sample volumes (75 µL for analysis of the supernatant; 10 µL for suspension) were removed at each pH point. The samples for supernatant analysis were transferred to 1.5 ml, 0.22 µm filter tubes and centrifuged. The suspension and filtered supernatant samples were transferred into HPLC autosampler vials containing 990 µL of 50 mM sodium bicarbonate solution. The diluted samples were analyzed by HPLC to assess the characteristics of the preparations. The experiments indicated that, for example, a 10.2% of PYY solution can be adsorbed onto FDKP particles at pH 4.5 In this particular preparation, for example, the PYY content of the resultant powder was determined by HPLC to be 14.5% (w/w). Cascade measurements of aerodynamic characteristics of the powder showed a respirable fraction of 52% with a 98% cartridge emptying when discharged through the MedTone® dry powder inhaler (MannKind Corporation). Based on the results above, multiple sample preparations of PYY/FDKP powder were made, including, 5%, 10%, 15% and 20% PYY.

Pharmacokinetic and pharmacodynamic studies: Female ZDF rats were used in these experiments and divided into 7 groups; five rats were assigned to each group, except for Group 1 which had 3 rats. The rats were fasted for 24 hr prior to being given their assigned dose and immediately provided with food after dosing and allowed to eat as desired for the period of the experiment. Each rat in Group 1 received a 0.6 mg IV dose of PYY in phosphate buffered saline solution; Group 2 rats received 1.0 mg of PYY pulmonary liquid instillation; Group 3 rats were designated as control and received a stream of air; Groups 4-7 rats received a dry powder formulation for inhalation administered by pulmonary insufflation as follows: Group 4 rats received 0.15 mg of PYY in a 3 mg PYY/FDKP powder formulation of 5% PYY (w/w) load; Group 5 rats received 0.3 mg of PYY in a 3 mg PYY/FDKP powder formulation of 10% PYY (w/w) load; Group 6 rats received 0.45 mg of PYY in a 3 mg PYY/FDKP powder formulation of 15% PYY (w/w) load; Group 7 rats received 0.6 mg of PYY in a 3 mg PYY/FDKP powder formulation of 20% PYY (w/w) load.

Figure 14:
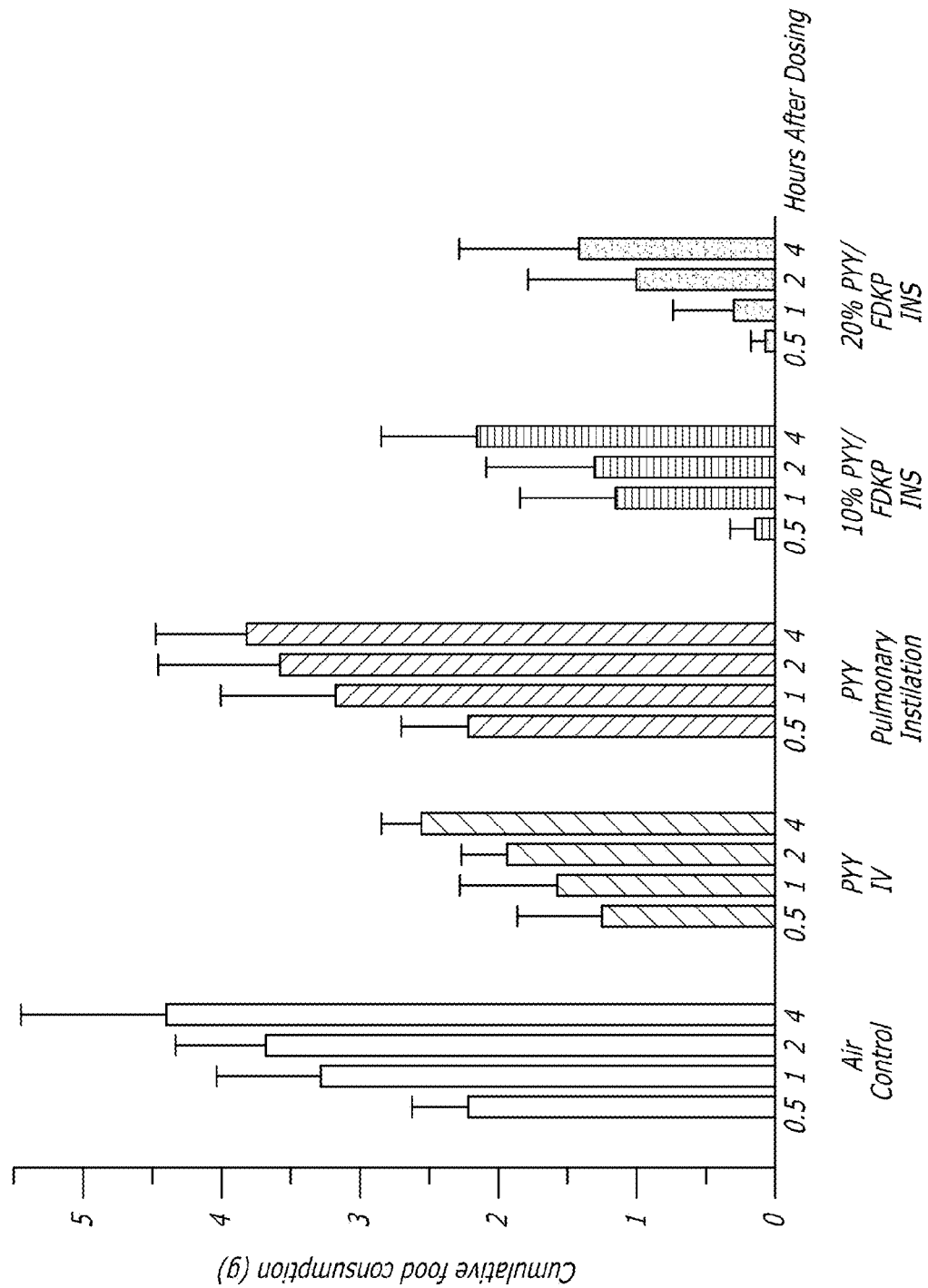
FIG. 14 depicts cumulative food consumption in male ZDF rats receiving air control by pulmonary insufflation, peptide YY(3-36) (PYY) alone by IV injection, PYY alone by pulmonary instillation, 10% PYY/FDKP powder (0.3 mg PYY) by pulmonary insufflation; 20% PYY/FDKP powder (0.6 mg PYY) by pulmonary insufflation. For each group food consumption was measured 30 minutes after dosing, 1 hour after dosing, 2 hours after dosing, and 4 hours after dosing. Data are plotted mean±SD.
Figure 15:
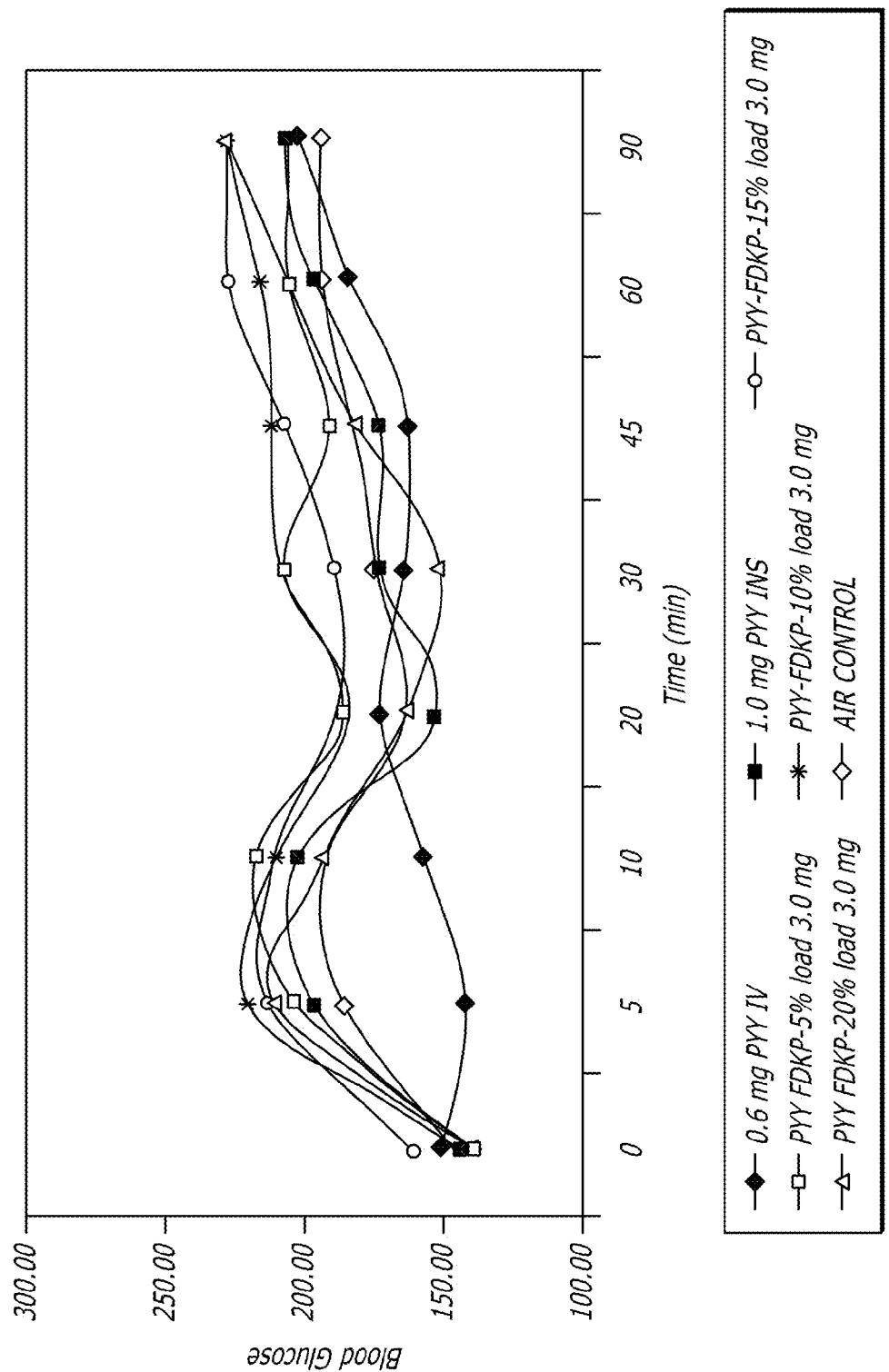
FIG. 15 depicts the blood glucose concentration in female ZDF rats administered PYY/FDKP powder by pulmonary insufflation versus intravenously administered PYY at various times following dose administration.
Figure 16:
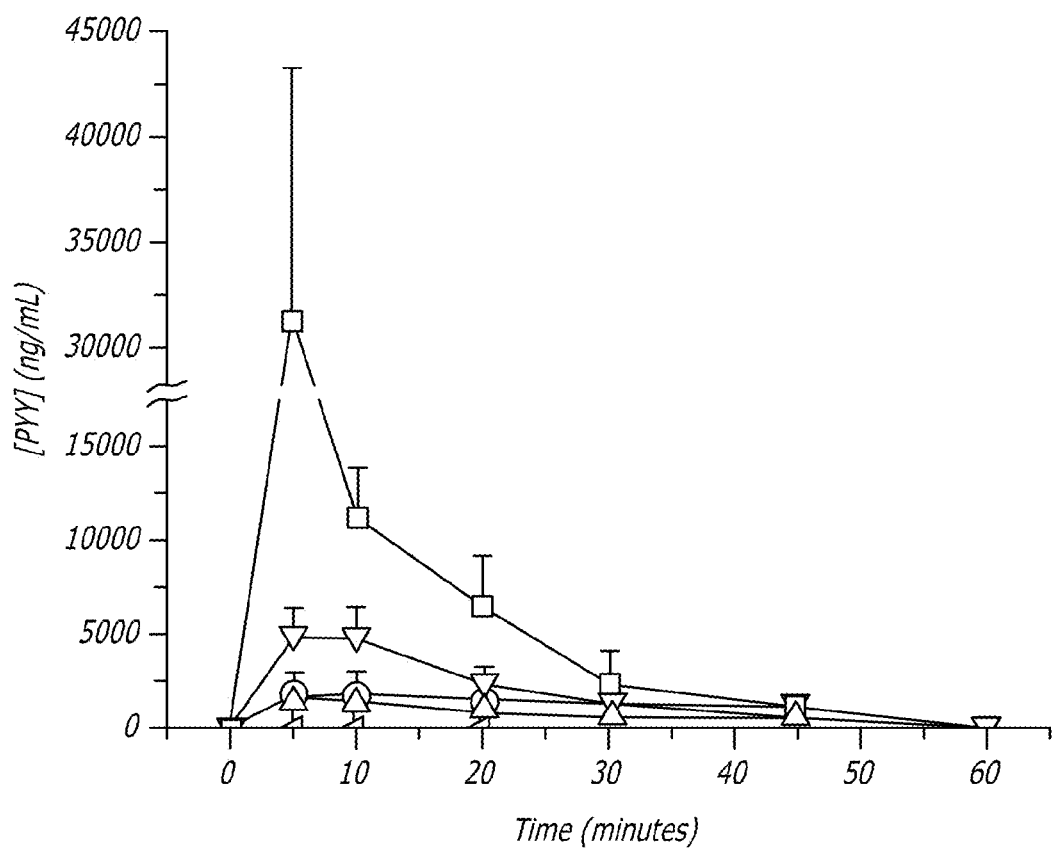
FIG. 16 depicts mean plasma concentrations of PYY in female ZDF rats receiving PYY/FDKP powder by pulmonary insufflation versus intravenously administered PYY. The squares represent the response following intravenous administration of PYY alone (0.6 mg). The circles represent the response following liquid instillation of PYY alone (1 mg). The down triangles represent the response following pulmonary insufflation of 20% PYY/FDKP powder (0.6 mg PYY). The up triangles represent the response following pulmonary insufflation of 10% PYY/FDKP powder (0.3 mg PYY). The left-pointing triangles represent the response following pulmonary insufflation of air alone. Data are plotted as ±SD.

Food consumption was measured for each rat at 30, 60, 90, 120, 240 min and 24 hr after dosing. PYY plasma concentrations and glucose concentrations were determined for each rat from blood samples taken from the rats before dosing and at 5, 10, 20, 30, 45, 60 and 90 min after dosing. The results of these experiments are shown in FIGS. 14-16 and Table 6 below. FIG. 14 is a bar graph of representative data from experiments measuring food consumption in female ZDF rats receiving PYY formulations by intravenous administration and by pulmonary administration in a formulation comprising a fumaryl-diketopiperazine at the various doses. The data show that food consumption was reduced for all PYY-treated rats when compared to control with the exception of Group 2 which received PYY by instillation. Reduction in food consumption by the rats was statistically significant for the rats treated by pulmonary insufflation at 30, 60, 90 and 120 min after PYY-dosing when compared to control. The data in FIG. 14 also show that while IV administration (Group 1) is relatively effective in reducing food consumption in the rats, the same amount of PYY (0.6 mg) administered by the pulmonary route in an FDKP formulation (Group 7) was more effective in reducing the amount of food intake or suppressing appetite for a longer period of time. All PYY-treated rats receiving pulmonary PYY-FDKP powders consumed less food when compared to controls.

FIG. 15 depicts the measured blood glucose levels in the female ZDF rats given PYY formulations by IV administration; by pulmonary administration with various formulations comprising a fumaryl-diketopiperazine and air control rats. The data indicate the blood glucose levels of the PYY-treated rats by pulmonary insufflation remained relatively similar to the controls, except for the Group 1 rats which were treated with PYY IV. The Group 1 rats showed an initial lower blood glucose level when compared to the other rats up to about 15 min after dosing.

FIG. 16 depicts representative data from experiments measuring the plasma concentration of PYY in the female ZDF rats given PYY formulations by IV administration; by pulmonary administration with various formulations comprising a fumaryl-diketopiperazine, and air control rats taken at various times after administration. These measurements are also represented in Table 6. The data show that Group 1 rats which were administered PYY IV attained a higher plasma PYY concentration (30.7 µg/mL) than rats treated by pulmonary insufflation. Peak plasma concentration ($T_{max}$) for PYY was about 5 min for Groups 1, 6 and 7 rats and 10 min for Group 2, 4 and 5 rats. The data show that all rats treated by pulmonary insufflation with a PYY/FDKP formulation had measurable amounts of PYY in their plasma samples, however, the Group 7 rats had the highest plasma PYY concentration (4.9 µg/mL) and values remained higher than the other groups up to about 35 min after dosing. The data also indicate that the plasma concentration of PYY administered by pulmonary insufflation is dose dependent. While administration by IV injection led to higher venous plasma concentration of PYY than did pulmonary administration of PYY/FDKP at the dosages used, the greater suppression of food consumption was nonetheless achieved with pulmonary administration of PYY/FDKP.

TABLE 6

| Rat Group Number | T½ (min) | Tmax (min) | Cmax (µg/mL) | AUCall/D (min/mL) | BA (%) |
|---|---|---|---|---|---|
| 1 | 13 | 5 | 30.7 | 0.61 | 100% |
| 2 | 22 | 10 | 1.7 | 0.06 | 11 |
| 4 | 23 | 10 | 0.51 | 0.10 | 16 |
| 5 | 30 | 10 | 1.33 | 0.15 | 25 |
| 6 | 26 | 5 | 2.79 | 0.20 | 33 |
| 7 | 22 | 5 | 4.90 | 0.22 | 36 |

Figure 17:
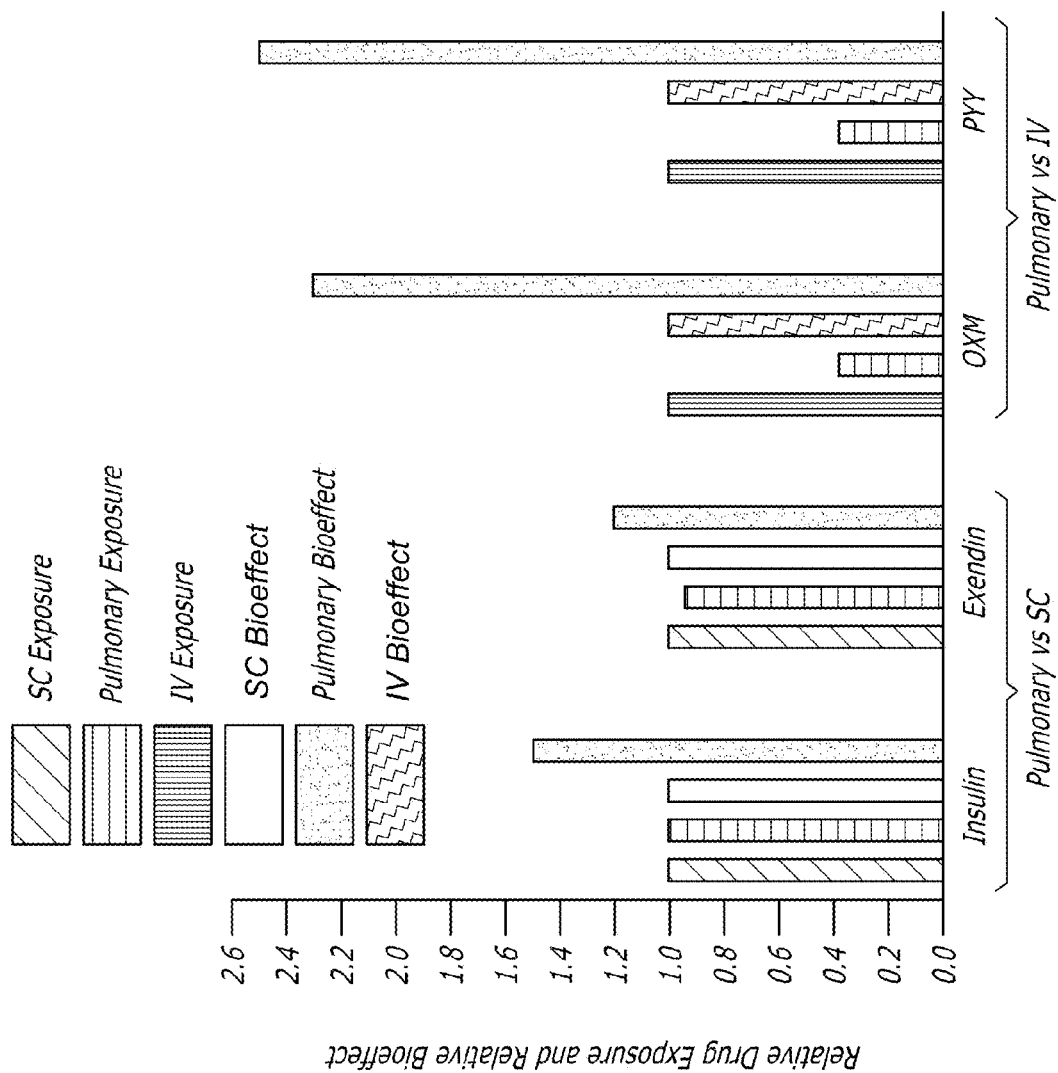
FIG. 17 depicts the relative drug exposure and relative bioeffect of the present formulations administered by pulmonary inhalation and containing insulin, exendin, oxyntomodulin or PYY compared to subcutaneous and intravenous administration.

FIG. 17 illustrates the effectiveness of the present drug delivery system as measured for several active agents, including insulin, exendin, oxyntomodulin and PYY and exemplified herewith. Specifically, FIG. 17 demonstrates the relationship between drug exposure and bioeffect of the pulmonary drug delivery system compared to IV and SC administration of the aforementioned active agents. The data in FIG. 17 indicate that the present pulmonary drug delivery system provides a greater bioeffect with lesser amounts of drug exposure than intravenous or subcutaneous administration. Therefore, lesser amounts of drug exposure can be required to obtain a similar or greater effect of a desired drug when compared to standard therapies. Thus, in one embodiment, a method of delivering an active agent including, peptides such as GLP-1, oxyntomodulin, PYY, for the treatment of disease, including diabetes, hyperglycemia and obesity which comprises administering to a subject in need of treatment an inhalable formulation comprising one or more active agents and a diketopiperazine whereby a therapeutic effect is seen with lower exposure to the active agent than required to achieve a similar effect with other modes of administration. In one embodiment, the active agents include peptides, proteins, lipokines.

Example 8

Assessment of Glp-1 Activity in Postprandial Type 2 Diabetes Mellitus.

The purpose of this study was to evaluate the effect of a GLP-1 dry powder formulation on postprandial glucose concentration and assess its safety including adverse events, GPL-1 activity, insulin response, and gastric emptying.

Experimental Design: The study was divided into two periods and enrolled 20 patients diagnosed with type 2 diabetes ranging in age from 20 to 64 years of age. Period 1 was an open-label, single-dose, trial in which 15 of the patients received a dry powder formulation comprising 1.5 mg of GLP-1 in FDKP administered after having fasted overnight. As control, 5 subjects received FDKP inhalation powder after fasting overnight. Period 2 was performed after completion of Period 1. In this part of the study, the patients were given 4 sequential treatments each with a meal challenge consisting of 475 Kcal and labeled with $^{13}$C-octanoate as marker. The study was designed as a double-blind, double dummy, crossover, meal challenge study, in which saline as control and exenatide were given as injection 15 minutes before a meal and dry powder formulations of inhalable GLP-1 or placebo consisting of a dry powder formulation without GLP-1, were administered immediately before the meal and repeated 30 minutes after the meal. The four treatments were as follows: Treatment 1 consisted of all patients receiving a placebo of 1.5 mg of dry powder formulation without GLP-1. In Treatment 2, all patients received one dose of 1.5 mg of GLP-1 in a dry powder formulation comprising FDKP. In Treatment 3, all patients received two doses of 1.5 mg of GLP-1 in a dry powder formulation comprising FDKP, one dose immediately before the meal and one dose 30 minutes after the meal. In Treatment 4, the patients received 10 µg of exenatide by subcutaneous injection. Blood samples from each patient were taken at various times before and after dosing and analyzed for several parameters, including GLP-1 concentration, insulin response, glucose concentration and gastric emptying. The results of this study are depicted in FIGS. 18-20.

Figure 18:
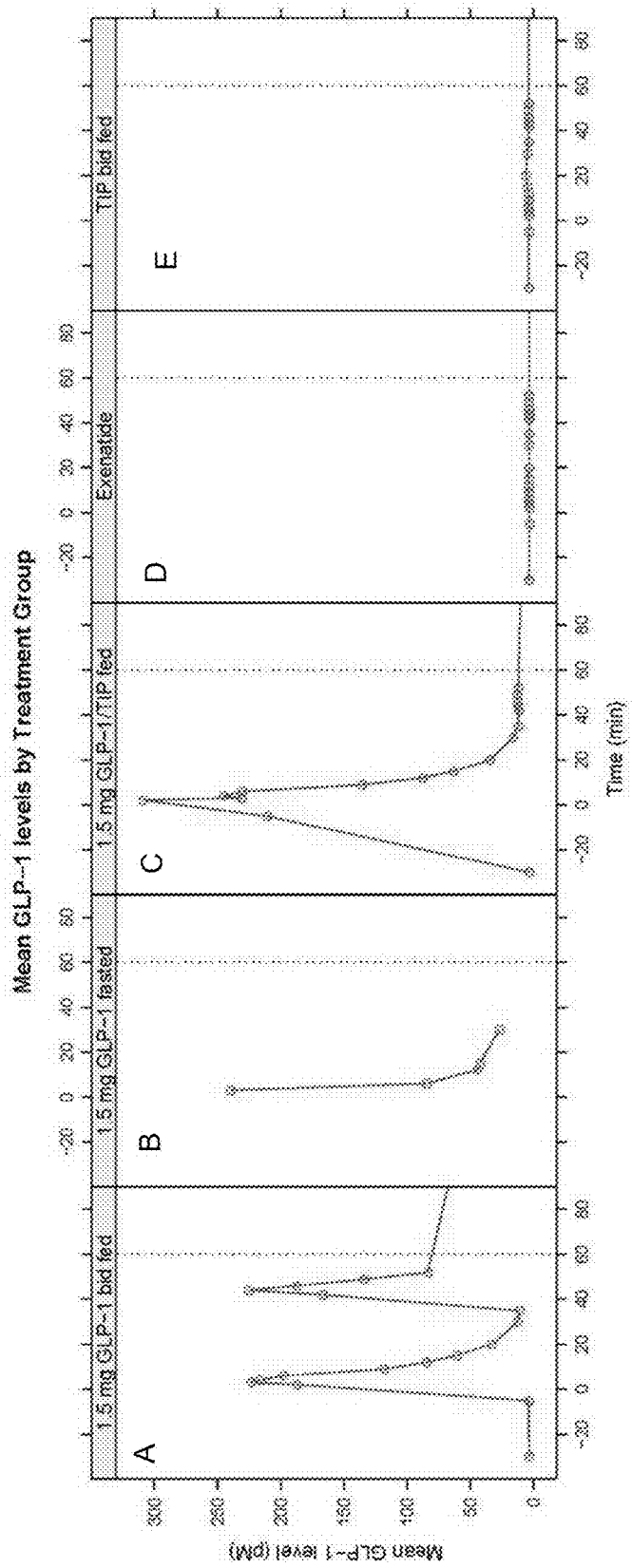
FIG. 18 depicts mean GLP-1 plasma levels in patients administered various inhaled GLP-1 and control formulations.

FIG. 18 depicts the mean GLP-1 levels in blood by treatment group as described above. The data demonstrate that the patients receiving the dry powder formulation comprising 1.5 mg of GLP-1 in FDKP had significantly higher levels of GLP-1 in blood soon after administration as shown in panels A, B and C and that the levels of GLP-1 sharply declined after administration in fed or fasted individuals. There were no measurable levels of GLP-1 in the exenatide-treated group (Panel D), or in controls (Panel E) receiving the dry powder formulation.

Figure 19:
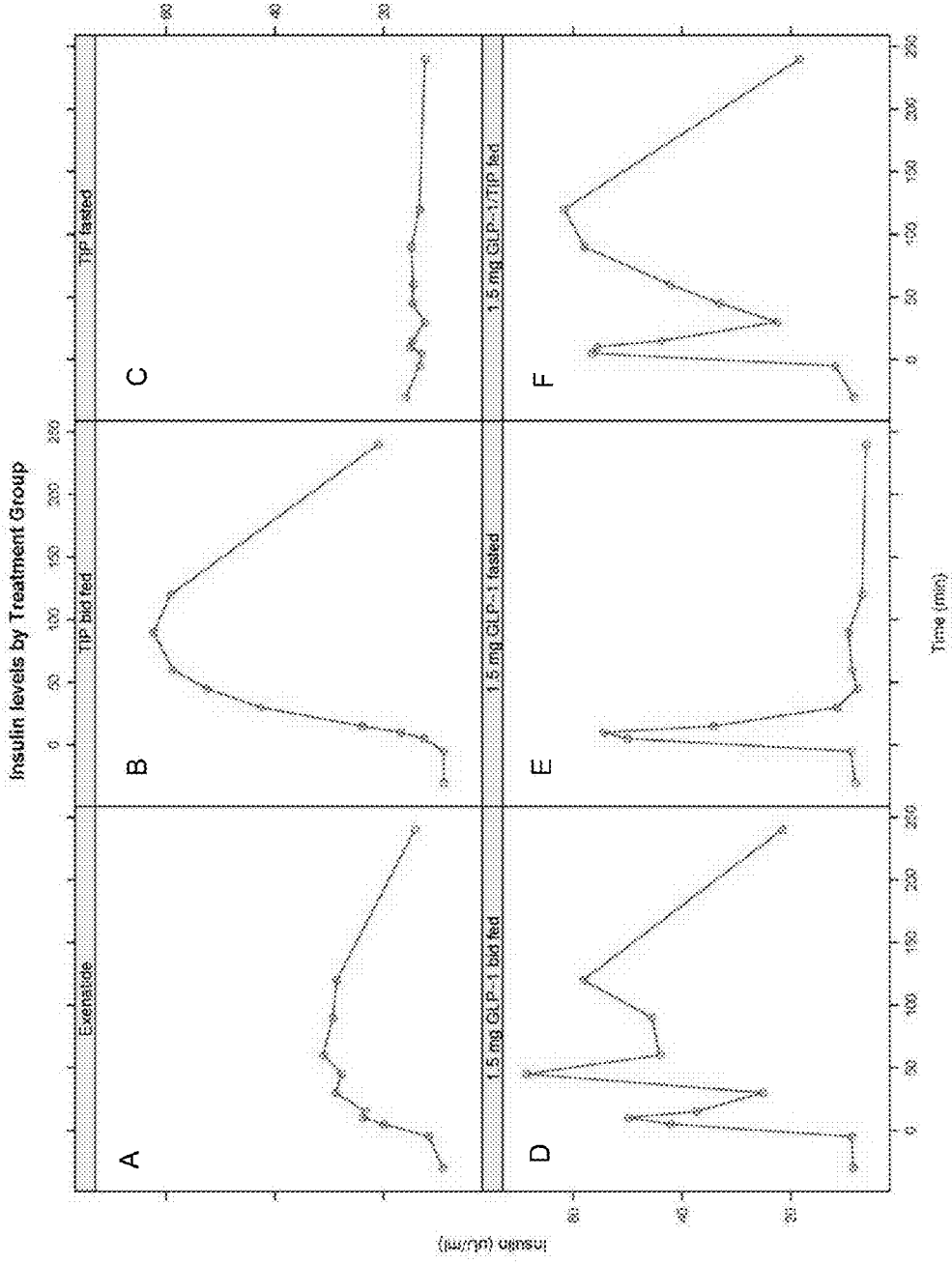
FIG. 19 depicts plasma insulin levels in patients administered various inhaled GLP-1 and control formulations.

FIG. 19 depicts the insulin levels of the patients in the study before or after treatment. The data show that endogenous insulin was produced in all patients after treatment including the placebo-treated patients in the meal challenge studies (Panel B), except for the fasted control patients (Panel C) who received the placebo. However, the insulin response was more significant in patients receiving GLP-1 in a dry powder composition comprising FDKP, in which the insulin response was observed immediately after treatment in both fed and fasted groups (Panels D-F). The results also showed that the glucose levels were reduced in patients treated with the dry powder formulation of GLP-1. Administration of the dry powder formulation of GLP-1 resulted in a delayed rise in blood glucose and reduced overall exposure (AUC) to glucose. Both the delayed rise and lessened exposure were more pronounced in subjects receiving a second administration of GLP-1 inhalation powder (data not shown). The magnitude of insulin release varied among patients, with some showing small but physiologically relevant levels of insulin whereas others exhibited much larger insulin releases. Despite the difference in insulin response between the patients, the glucose response was similar. This difference in insulin response may reflect variations in degree of insulin resistance and disease progression. Assessment of this response can be used as a diagnostic indicator of disease progression with larger releases (lacking greater effectiveness at controlling blood glucose levels) indicating greater insulin resistance and disease progression.

Figure 20:
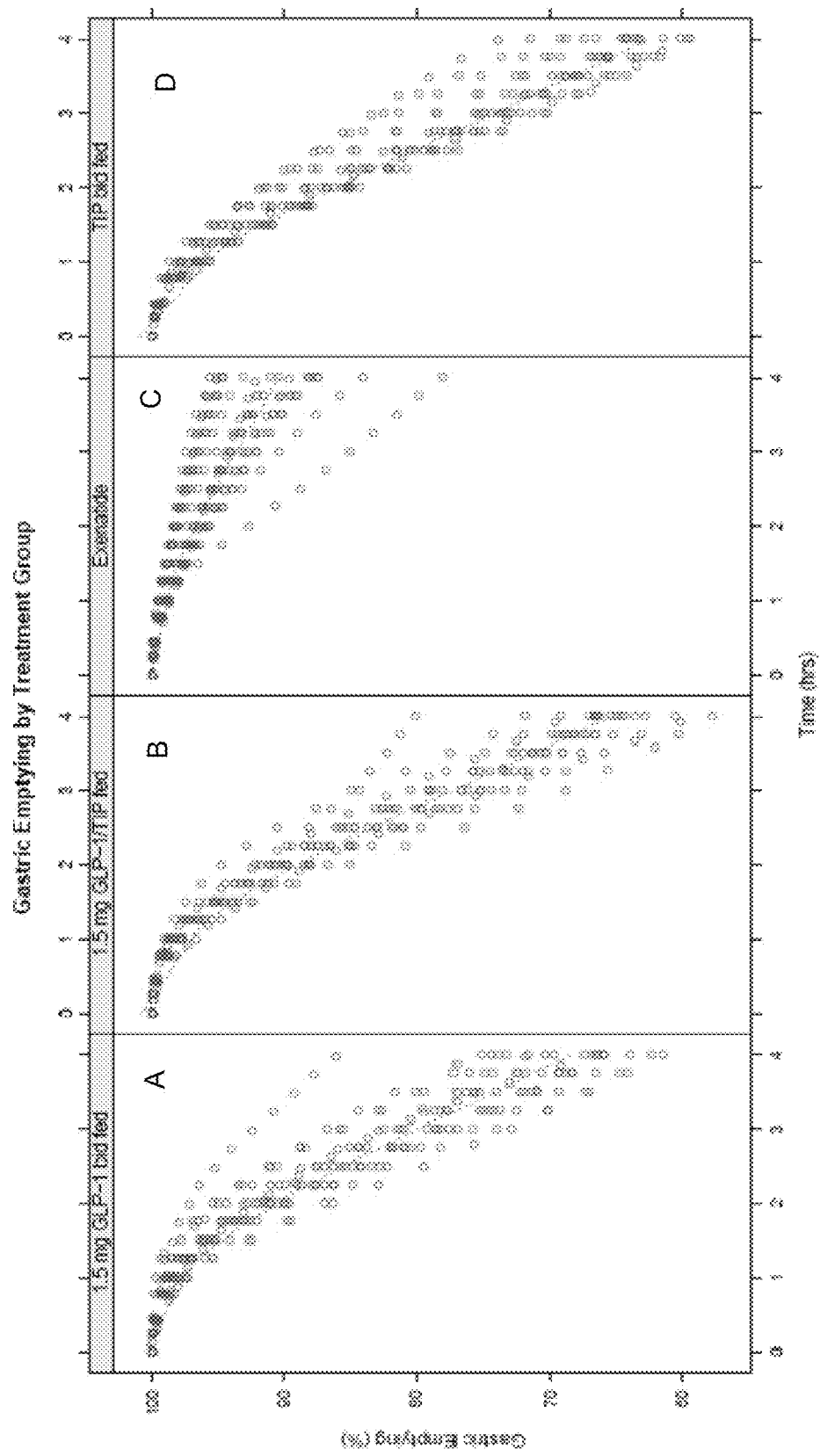
FIG. 20 depicts gastric emptying in response to an inhaled GLP-1 formulation in patients administered various inhaled GLP-1 and control formulations.

FIG. 20 depicts the percent gastric emptying by treatment groups. Panel A (patients in Treatment 3) and Panel B (patients in Treatment 2) patients had similar gastric emptying characteristics or percentages as the control patients shown in Panel D (Placebo treated patients with a dry powder formulation comprising FDKP without GLP-1). The data also show that patients treated with exenatide even at a 10 µg dose exhibited a significant delay or inhibition in gastric emptying when compared to controls. The data also demonstrate that the present system for delivering active agents comprising FDKP and GLP-1 lacks inhibition of gastric emptying; induces a rapid insulin release following GLP-1 delivery and causes a reduction in glucose AUC levels.

Example 9

Preparation and characterization of Sumatriptan-Disodium Fumaryl Diketopiperazine (Sumatriptan-Na$_2$FDKP) Inhalation Dry Powder Sumatriptan-Na$_2$FDKP powder was prepared from commercially available tablets of sumatriptan succinate. Sumatriptan succinate (Imitrex®, GlaxoSmithKline) was extracted from crushed tablets suspended in HPLC grade water to form a solution. The solution was then filtered through 0.45 µm nylon syringe filters to remove undissolved excipients and the filtrate was processed through a quaternary amine ion exchange extraction column to eliminate the succinate group. The sumatriptan in solution at a concentration greater than 10 mg/mL was then combined with a solution of Na$_2$FDKP at a concentration greater than about 10 mg/mL in solution. The Na$_2$FDKP was either prepared earlier or prepared from the FDKP free acid by dissolution with two equivalents of sodium hydroxide. In some experiments, the ratio of the concentration of sumatriptan starting solution to FDKP was greater than 1. The solution was spray dried (Buchi Mini Spray Dryer Model B-290) at an inlet temperature of from about 145° C. to about 200° C. and an outlet temperature of from about 75° C. to about 85° C. The drying gas was nitrogen set at a flow rate of about 670 L/hr. A dried powder was obtained.

Figure 21:
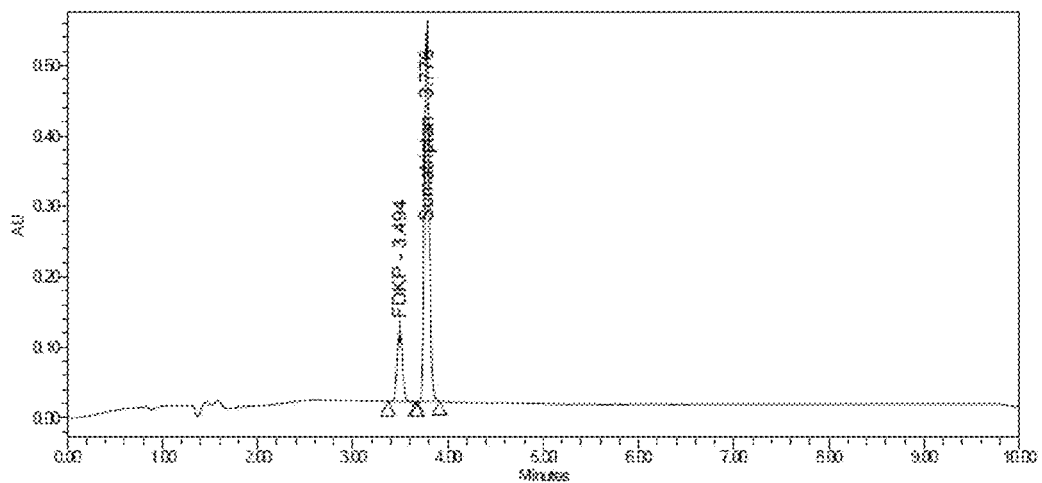
FIG. 21 depicts an HPLC chromatogram of a solution containing sumatriptan-Na$_2$FDKP spray-dried powders.

To ascertain the amount of sumatriptan in the powder, a sample of the powder was dissolved in an HPLC solution and assayed for content using a high pressure liquid chromatography (HPLC) system. The HPLC method quantifies sumatriptan in the presence of FDKP. FIG. 21 depicts an HPLC chromatogram of a solution of the dissolved powder, which shows that the two compounds can be easily separated and identified. Powders were also tested by thermal analysis (TGA and DSC) and cascade impaction. Table 7 shows representative data of Sumatriptan-Na$_2$FDKP powder characteristics made by the instant method, wherein the ratio of sumatriptan succinate concentration to FDKP in solution was about 1.5.

TABLE 7

| Assay (wt %) | | | | Cascade impaction | |
|---|---|---|---|---|---|
| Sumatriptan (% by weight) | FDKP | LOD | Total | % RF/fill | % CE |
| 38.8* | 37.0 | 3.4 | 79.2 | 17.9 | 68.0 |

*Target Sumatriptan level = 40%

Sumatriptan-Na$_2$FDKP powders made by the present method contained up to about 40% by weight of sumatriptan. The water content determined by loss on drying (LOD) was about 3.4%. The percent respirable fraction per fill was about 18%, and the amount of powder delivered by or emitted from the inhaler (cartridge emptying, CE) was about 68% using a using a breath powered inhaler as described in U.S. patent application Ser. No. 12/473,125 (US 2009/0308390), which disclosure is incorporated by reference in its entirety.

Table 8 illustrates the characterization of the bulk dry powder.

TABLE 8

| Assay (wt %) | | | | Cascade impaction | |
|---|---|---|---|---|---|
| Sumatriptan (% by weight) | FDKP | LOD | Total | % RF/fill | % CE |
| 38.8* | 37.0 | 3.4 | 79.2 | 17.9 | 68.0 |

*Target Sumatriptan level = 40%

Example 10

Sumatriptan-Na$_2$FDKP Inhalation Dry Powder—Pharmacokinetic (PK) and Pharmacodynamic (PD) Studies in Rats Powder preparation and characterization: Sumatriptan-Na$_2$FDKP powder was prepared as described in Example 9 above, except that the sumatriptan succinate was purchase from LGM Pharma (Boca Raton, Fla.) and L-leucine was added to study whether the aerodynamic performance of the resulting spray-dried powder formed would be improved. Three feed solutions were prepared at 4.5% total solids concentration for a 5 g scale. The feed solutions were prepared by adding FDKP disodium salt, sumatriptan succinate, and L-leucine (0-20 wt %) to de-ionized water with mixing. The solutions were titrated with dilute aqueous ammonia to pH 6.00. The resulting clear feed solutions were vacuum filtered through a 0.2 µm PES filter membrane and spray dried as described in Example 9, however, the drying gas flow was set at 25 kg/hr, the atomization flow was about 4 kg/hr and the atomization pressure was set at 4 bar. The sumatriptan succinate concentration (dry basis) in each solution was 56% to obtain a 40% sumatriptan target load. The powders were analyzed by HPLC, cascade impaction, Karl Fischer titration, scanning electron microscopy (SEM) and tap and bulk density. The results of these studies are shown in Table 9 and FIG. 22.

TABLE 9

| % L-leucine | Sumatriptan Assay (wt %) | % RF/fill | % CE | % water | Bulk density g/mL | Tapped density g/mL |
|---|---|---|---|---|---|---|
| 0 | 39.8 | 9.8 | 58.8 | 1.9 | 0.25 | 0.38 |
| 10 | 37.6 | 61.3 | 93.3 | 5.2 | 0.18 | 0.38 |
| 20 | 38.8 | 63.3 | 88.2 | 4.4 | 0.18 | 0.31 |

The data in Table 9 illustrate that the target and measured sumatriptan content for the bulk sumatriptan-Na$_2$FDKP powders are comparable. Aerodynamic performance improved with the addition of leucine. The powder without leucine had an RF/fill of 9.8% with 58.8% CE, the addition of 10% leucine increased RF/fill to 61.3% with 93.3% CE, and the addition of 20% leucine increased RF/fill to 63.3. % with 88.2% CE. The leucine-containing sumatriptan-Na$_2$FDKP powders had higher residual water content than the leucine-free powder. The addition of leucine also reduced the bulk powder density by approximately 30%.

Figure 22:
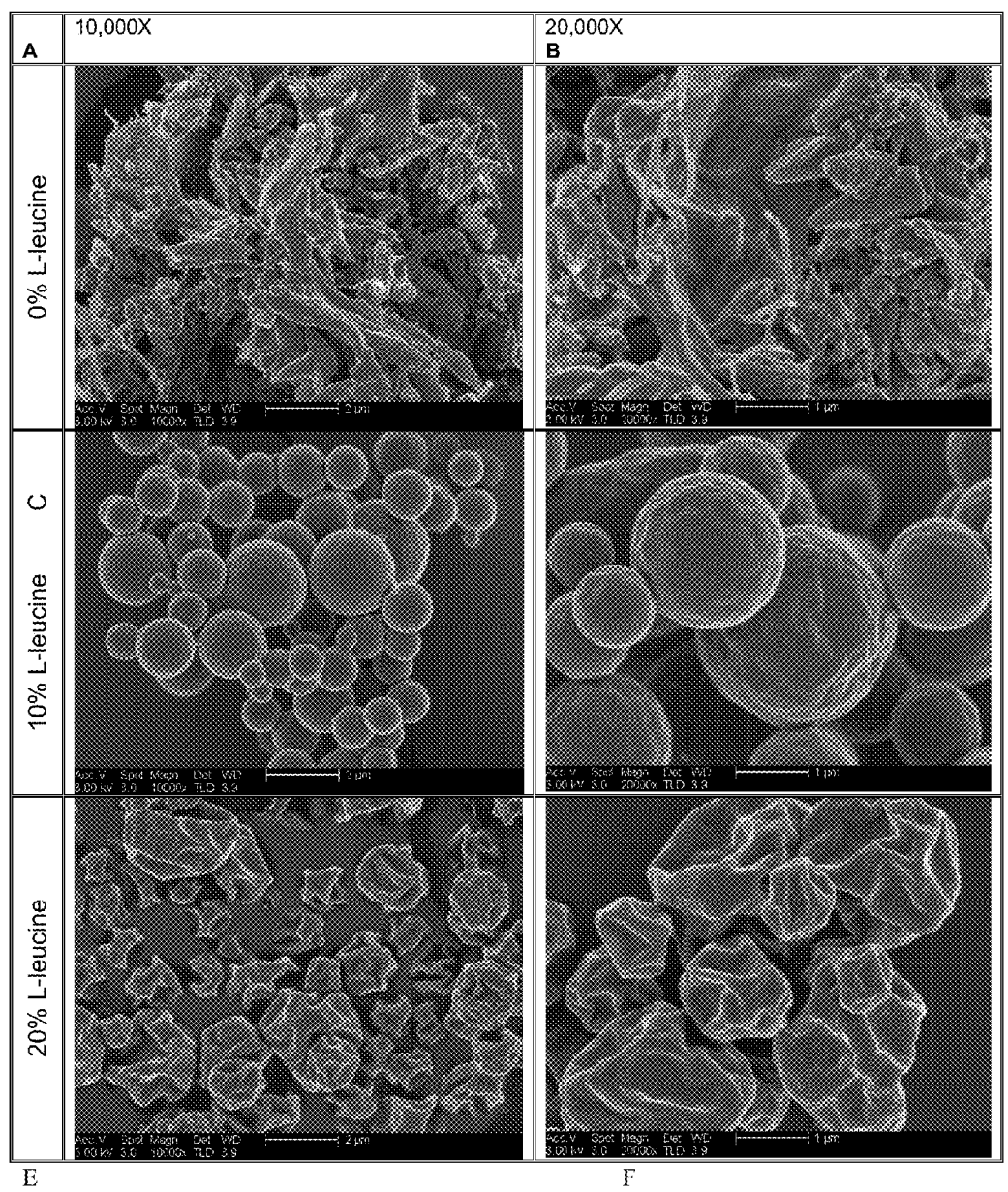
FIGS. 22 A and B are scanning electron micrographs of three powders made by the present method comprising sumatriptan-Na$_2$FDKP. Panels A and B represent powder particles without L-leucine. The powder particles with 10% leucine (Panel C and D) and the powder particles made with 20% leucine (Panel E and F).

FIG. 22 is a scanning electron micrograph of the three powders characterized in Table 3. As shown in panels A-F, each powder had distinct morphology. The particles without leucine were fused fragments with no uniform shape (Panel A and B). The particles with 10% leucine (Panel C and D) were substantially spherical with smooth surfaces and the particles made with 20% leucine (Panel E and F) have a raisin-like or shriveled morphology, typical of insulin-FDKP salt powders.

Stability of Sumatriptan-Na$_2$FDKP powders: Powders were also tested to determine their degree of stability. Samples of powder were incubated for a period of three months in an open dish exposed at 25° C./60% relative humidity (RH) and at 40° C./70% RH. Samples of the powders were assay by the HPLC method at 1, 2 and 3 months after the start of the experiments. The results are presented in Tables 10 and 11 below.

TABLE 10

Storage Condition: 25° C./60% RH
Sumatriptan Assay

| | Initial | 1 month | 2 months | 3 months |
|---|---|---|---|---|
| 0% L-leucine powder | 39.8 | 38.9% | 39.9% | 39.6% |
| | (100%) | (98%) | (100%) | (98%) |
| 10% L-leucine powder | 37.6 | 39.1% | 40.0% | 39.0% |
| | (100%) | (104%) | (106%) | (104%) |
| 20% L-leucine powder | 38.8 | 38.9% | 40.2% | 39.4% |
| | (100%) | (100%) | (104%) | (102%) |

TABLE 11

Storage Condition: 40° C./75% RH
Sumatriptan Assay

| | Initial | 7 days | 14 days |
|---|---|---|---|
| 0% L-leucine powder | 39.8 | 38.0 | 37.8 |
| | (100%) | (95%) | (95%) |
| 10% L-leucine powder | 37.6 | 38.8 | 38.6 |
| | (100%) | (103%) | (103%) |
| 20% L-leucine powder | 38.8 | 39.3 | 39.3 |
| | (100%) | (101%) | (101%) |

The data show that there was no degradation of the sumatriptan in the composition even after three months of exposure to 25° C./60% RH with or without L-leucine. At higher temperature, 40° C./70% RH, however, an insignificant, but slight decrease in sumatriptan content is observed after 1 and 2 weeks of incubation when compared to the samples containing L-leucine.

Inhalation studies in rats using Sumatriptan-Na$_2$FDKP powders: Powders prepared as described above were used in these experiments. The PK profile of sumatriptan administered as sumatriptan-Na$_2$FDKP powder (37.4% sumatriptan by weight) by pulmonary insufflation was evaluated and compared to sumatriptan nasal spray administered by pulmonary instillation or sumatriptan administered by intravenous injection or subcutaneous injection in female Sprague Dawley rats (n=6/group) (Table 12).

TABLE 12

| Group | Test Article | Achieved Sumatriptan Dose (mg) |
|---|---|---|
| 1 | Air Control | 0 |
| 2 | Sumatriptan by intravenous injection | 0.358 |
| 3 | Sumatriptan by subcutaneous injection | 0.358 |
| 4 | Sumatriptan nasal spray by pulmonary instillation | 0.483 |
| 5 | Sumatriptan-Na$_2$FDKP powder by pulmonary insufflation | 0.169* |

*mean achieved dose

Figure 23:
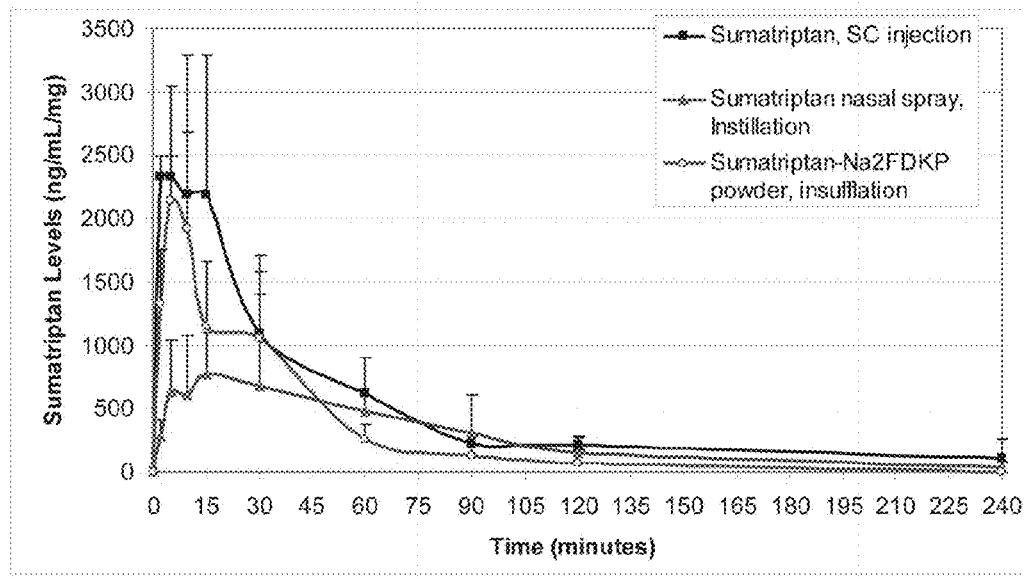
FIG. 23 depicts a graph of dose-normalized sumatriptan concentrations in blood samples following administration of sumatriptan-Na$_2$FDKP by insufflation compared to sumatriptan administered by SC injection and sumatriptan nasal spray by instillation for a period of 4 hrs after administration.

Blood samples for sumatriptan analysis were collected before dosing and at 2, 5, 10, 15, 30, 60, 90, 120 and 240 minutes after dosing. Animals were divided into two subsets (n=3/timepoint) for blood collection. Sumatriptan in serum was analyzed using an established LCMS assay. Maximum concentration and bioavailability of sumatriptan insufflated as sumatriptan-Na$_2$FDKP powder was higher than the sumatriptan administered by liquid instillation (nasal spray formulation) and comparable to sumatriptan administered by subcutaneous injection (FIG. 23). FIG. 23 shows that the time to maximum concentration was 5 minutes in the insufflation group versus 15 minutes in the pulmonary liquid instillation group. Overall dose-normalized exposure was similar for sumatriptan pulmonary insufflation and pulmonary liquid instillation, but the PK profiles are quite different. Sumatriptan was well tolerated across all treatment groups. Pharmacokinetic parameters were calculated using noncompartmental methods and the nonlinear regression program WinNonlin v5.2 (Table 12) based on the mean concentration curve (n=3/time point/formulation) after correction for the actual administered dose. Table 13 summarizes representative pharmacokinetic data in female Sprague Dawley rats.

TABLE 13

| Group | Route | AUC (min, ng/mL)/mg | $C_{max}$ ng/mL/mg | $t_{max}$ min | $t_{1/2}$ min | Bioavailability % |
|---|---|---|---|---|---|---|
| 2 | IV | 273,729 | 26,719 | 2 | 30.4 | 100 |
| 3 | SC | 99,583 | 2309 | 5 | 36.6 | 36.4 |
| 4 | LIS | 70,063 | 776 | 15 | 45.8 | 25.6 |
| 5 | INS | 69,411 | 2145 | 5 | 24 | 25.4 |

*IV = Intravenous injection;
SC = subcutaneous injection;
LIS = Pulmonary liquid instillation;
INS = pulmary insufflation It is apparent that the bioavailability of sumatriptan administered as Na$_2$FDKP sumatriptan powder by pulmonary insufflation was comparable to sumatriptan nasal spray administered by liquid instillation, but its PK profile ($t_{max}$, $C_{max}$) resembled SC injection.

Example 11

Sumatriptan-Na$_2$FDKP Inhalation Dry Powder—PK and PD Studies in Beagle Dogs

Figure 25:
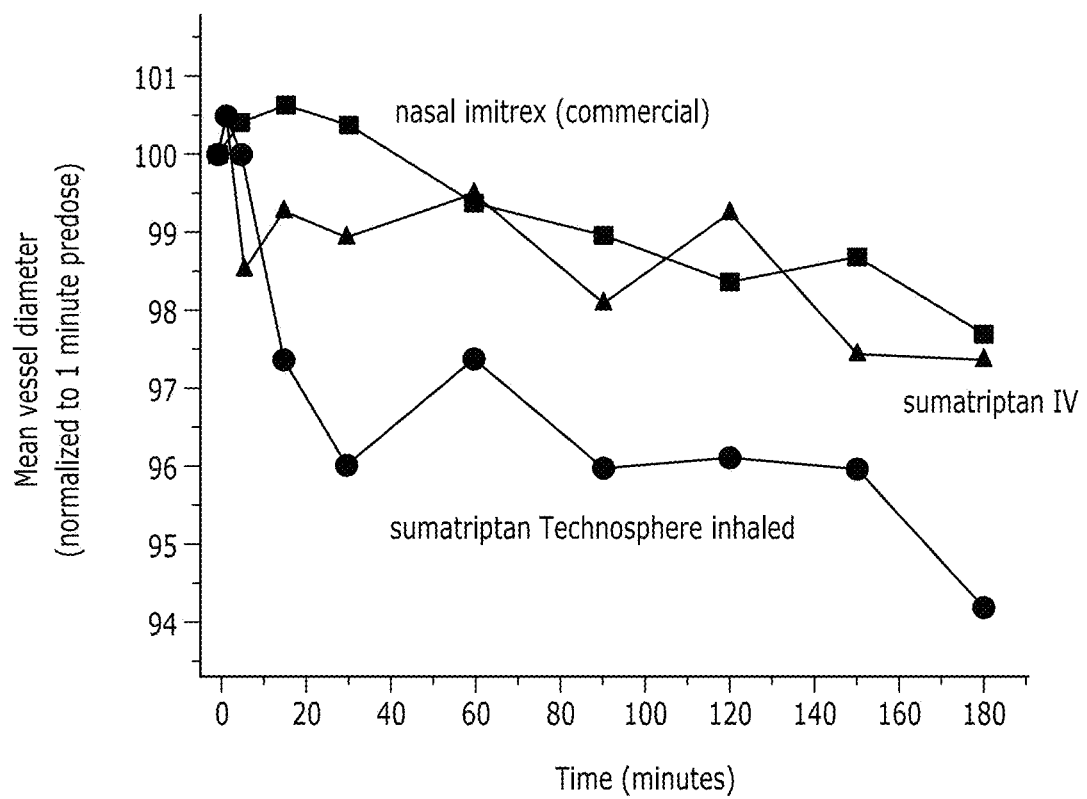
FIG. 25 depicts a graph of pharmacodynamic data showing the effects of intravenously administered sumatriptan compared to Imitrex® administered by nasal instillation and sumatriptan-Na$_2$FDKP by insufflation on blood vessel diameter.

Pharmacodynamic Study: The pharmacodynamic and pharmacokinetic profiles of sumatriptan were evaluated in an accepted migraine model in anesthetized dogs. The pathogenesis of migraine is primarily due to a marked and prolonged period of vasodilation of cranial vessels. A model of migraine was induced by a single intra-arterial injection of capsaicin which produces carotid vasodilation. Animals received either air control (n=2), sumatriptan by intranasal instillation using a microsprayer (0.28 mg/kg; n=3), sumatriptan-Na₂FDKP powder by pulmonary insufflation (0.28 mg/kg sumatriptan; n=3) or sumatriptan by intravenous bolus injection into a peripheral vessel (0.03 mg/kg; n=2). Heart rate, systolic, diastolic, mean arterial blood pressures, and carotid blood flow and diameter (mean, maximum, minimum flow) were monitored and recorded continuously. Data were collected continuously and reported as 1-minute averages at specific time points after sumatriptan administration. The study summary is presented in Tables 15 and the results are shown in FIGS. 25.

TABLE 15

Experimental design

| Group No. | No. of Animals | Model Induction | Test Material | Dose Levels (mg/kg) | Dose Regimen[a,b] | Monitoring Period |
|---|---|---|---|---|---|---|
| 1 | 2 | Capsaicin administered intra-arterially via a 1-minute infusion (56 μg/min; 1 mL/min) | Control | 0 | Intra-tracheal (insufflator) | 30 minutes of stable baseline followed by 5 minutes of monitoring after administration of capsaicin and prior to sumatriptan administration. Monitoring continued through at least 3 hours after dosing with test article |
| 2 | 3 | | Sumatriptan[c] | 0.28 | Nasal spray (microsprayer) | |
| 3 | 3 | | Sumatriptan Na₂FDKP powder | 0.29[d] | Intra-tracheal (insufflator) | |
| 4 | 2 | | Sumatriptan[c] | 0.030 | Intravenous | |

[a]Animals were anesthetized during all dosing procedures.
[b]Dosing with the appropriate test article commenced 5 minutes after model induction.
[c]Commercially available product (Imitrex ®).
[d]Equivalent to 0.75 mg/kg powder dose based on 38% content of active ingredient Sumatriptan-Na₂FDKP powder.

Blood samples from the dogs for sumatriptan analysis were collected before dosing and at 2, 5, 10, 15, 30, 60, 90, 120 and 240 minutes after dosing. Sumatriptan in serum was analyzed using an established LCMS assay.

Based on the PK data, one animal in the sumatriptan-Na₂FDKP powder group-treated appeared not to have not received test article, presumably due to technical difficulties. This animal showed unusually marked vasoconstriction which was suspect. Another animal in this group showed poor vasoconstriction and high levels of sumatriptan exposure. It was assumed that the tubes for blood samples from these two animals were inadvertently switched during collection. Therefore, data presented herewith were evaluated with (n=3) and without (n=2) the mis-dosed animal. Both sets of data suggest similar results.

Blood pressure and heart rate were unaltered by the administration of sumatriptan or control article, regardless of the route of administration. Systemic exposure of sumatriptan was associated with reductions in vasodilation. All groups, including the control, had reduction in carotid artery diameters from the end of capsaicin administration through 3 hours after dosing. Insufflation of sumatriptan-Na₂FDKP powder resulted in a more pronounced constriction of the carotid artery than the intra-nasal and intravenous routes of administration. The magnitude of vasoconstriction varied significantly between dose groups, so the data were analyzed in terms of vessel diameter relative to baseline diameter, or as a change in vessel diameter from the end of capsaicin dosing, or from baseline.

Figure 24:
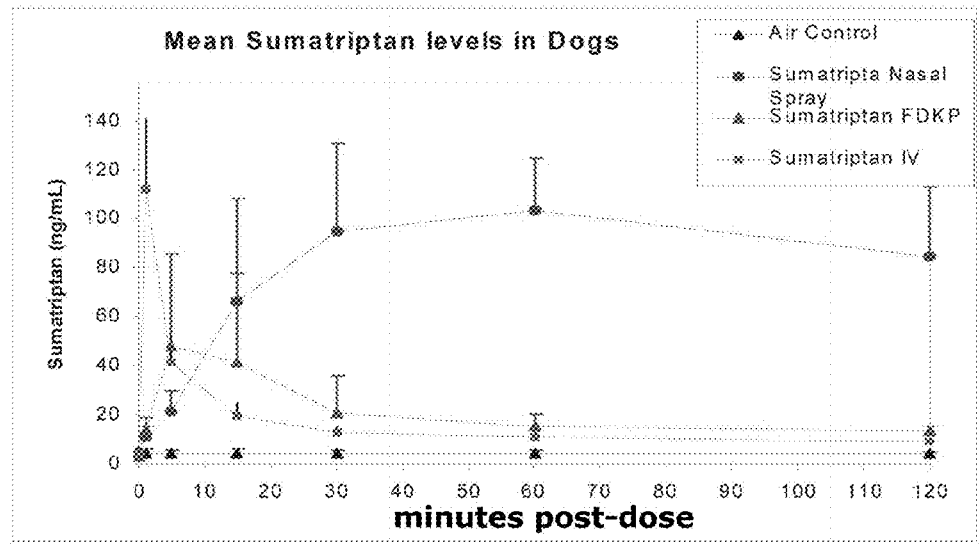
FIG. 24 depicts a graph showing the mean sumatriptan levels in blood in dogs following sumatriptan administered as a nasal spray, sumatriptan administered intravenously and sumatriptan-Na$_2$FDKP by insufflation compared to control dogs exposed to air insufflation.

The pharmacokinetic profiles of sumatriptan administered as sumatriptan-Na₂FDKP powder, nasal spray, or intravenous injection (FIG. 24) were consistent with the previous PK study in rats. FIG. 24 depicts the pharmacokinetic profile of sumatriptan FDKP salt powder (38% sumatriptan) administered by pulmonary insufflation, sumatriptan administered by nasal instillation, and intravenous injection in female dogs wherein the data are plotted as ±SD. The data show that the time to maximum mean peak circulating sumatriptan concentrations ($T_{max}$) was 5 minutes for the sumatriptan-FDKP salt powder and 60 minutes for nasal instillation. Even though $C_{max}$ and bioavailability were much lower for the sumatriptan-Na₂FDKP powder, animals insufflated with sumatriptan-Na₂FDKP exhibited a similar but faster pharmacodynamic response than those receiving the nasal spray.

FIG. 25 shows results from these experiments. The data indicate that reduction in vessel diameter from the end of capsaicin to the end of experiment was largest in the group treated with the sumatriptan-Na₂FDKP powder. The variability in initial vasodilation between groups complicates the analysis, but Group 2 (nasal spray) and group 3 (sumatriptan-Na₂FDKP powder) responded comparably to capsaicin. The group treated with sumatriptan-Na₂FDKP powder experienced a larger net constriction in blood vessels and, moreover, the effect had a faster onset of action.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A pharmaceutical composition comprising bis-3,6-[(N-fumaryl-4-aminobutyl)]-2,5-diketopiperazine or a salt thereof, 1-50 mg of sumatriptan or rizatriptan, and an aliphatic amino acid selected from the group consisting of alanine, glycine, leucine, isoleucine, norleucine, and serine, wherein said aliphatic amino acid is about 0.5% to about 30% by weight of the composition.

2. The pharmaceutical composition of claim 1, comprising bis -3,6[(N-fumaryl-4-aminobutyl)]-2,5-diketopiperazine and sumatriptan in a dry powder form.

3. The pharmaceutical composition of claim 2, wherein the composition is inhalable.

4. The pharmaceutical composition of claim 3, wherein the composition further comprises an excipient.

5. The pharmaceutical composition of claim 2, wherein the dry powder comprises microparticles, wherein from about 35% to about 75% of said microparticles have an aerodynamic diameter of less than 5.8 µm.

6. The pharmaceutical composition of claim 1, wherein the composition further comprises L-leucine.

7. The pharmaceutical composition of claim 1, wherein the aliphatic amino acid is alanine.

8. The pharmaceutical composition of claim 1, wherein the aliphatic amino acid is glycine.

9. The pharmaceutical composition of claim 1, wherein the aliphatic amino acid is isoleucine.

10. The pharmaceutical composition of claim 1, wherein the aliphatic amino acid is norleucine.

11. The pharmaceutical composition of claim 1, wherein the aliphatic amino acid is serine.

12. The pharmaceutical composition of claim 1, comprising bis -3,6[(N-fumaryl-4-aminobutyl)]-2,5-diketopiperazine and rizatriptan in a dry powder form.

13. A method of treating a migraine comprising: providing a patient with migraine symptoms an inhaler comprising the pharmaceutical composition of claim 1 in a dry powder form comprising bis-3,6[(N-fumaryl-4-aminobutyl)]-2,5-diketopiperazine, the aliphatic amino acid and 1-50 mg of sumatriptan or rizatriptan; wherein the aliphatic amino acid is L-leucine and wherein a therapeutically effective amount of said dry powder composition is administered to said patient by oral inhalation.

* * * * *

UNITED STATES PATENT AND TRADEMARK OFFICE
CERTIFICATE OF CORRECTION

Page 1 of 2

PATENT NO. : 8,785,396 B2
APPLICATION NO. : 13/293017
DATED : July 22, 2014
INVENTOR(S) : Leone-Bay et al.

It is certified that error appears in the above-identified patent and that said Letters Patent is hereby corrected as shown below:

In the specification

Column 3, lines 57-59, the formula "bis[3,6-(N-fumaryl-4-aminobutyl)]-2,5-d iketopiperazine or bis[3,6-(N-fumaryl-4-aminobutyl)]-2,5-diketopiperazine" should read --3,6-bis(N-fumaryl-4-aminobutyl)-2,5-diketopiperazine or 3,6-bis(N-fumaryl-4-aminobutyl)-2,5-diketopiperazine--

Column 8, lines 37-38, the formula "3,6-di(fumaryl-4-aminobutyl)-2,5-diketopiperazine" should read --3,6-di(N-fumaryl-4-aminobutyl)-2,5-diketopiperazine--

Column 8, lines 45-49, the formula "3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine" should read --3,6-di(N-succinyl-4-aminobutyl)-2,5-diketopiperazine, 3,6-di(N-maleyl-4-aminobutyl)-2,5-diketopiperazine, 3,6-di(N-glutaryl-4-aminobutyl)-2,5-diketopiperazine, 3,6-di(N-malonyl-4-aminobutyl)-2,5-diketopiperazine, 3,6-di(N-oxalyl-4-aminobutyl)-2,5-diketopiperazine, and 3,6-di(N-fumaryl-4-aminobutyl)-2,5-diketopiperazine--

In the claims

Column 44, lines 12-13, the formula "bis-3,6-[(N-fumaryl-4-aminobutyl)]-2,5-diketopiperazine" should read --3,6-bis(N-fumaryl-4-aminobutyl)-2,5-diketopiperazine--

Column 44, line 20, the formula "bis -3,6[(N-fumaryl-4-aminobutyl)]-2,5-diketopiperazine" should read --3,6-bis(N-fumaryl-4-aminobutyl)-2,5-diketopiperazine--

Column 44, lines 43-44, the formula "bis -3,6[(N-fumaryl-4-aminobutyl)]-2,5-diketopiperazine" should read --3,6-bis(N-fumaryl-4-aminobutyl)-2,5-diketopiperazine--

Signed and Sealed this
Nineteenth Day of April, 2016

Michelle K. Lee
*Director of the United States Patent and Trademark Office*

Column 44, lines 49-50, the formula "bis -3,6[(N-fumaryl-4-aminobutyl)]-2,5-diketopiperazine" should read --3,6-bis(N-fumaryl-4-aminobutyl)-2,5-diketopiperazine--